United States Patent
Brown et al.

(10) Patent No.: US 12,240,825 B2
(45) Date of Patent: Mar. 4, 2025

(54) OXEXIN 1 RECEPTOR ANTAGONISTS

(71) Applicant: Heptares Therapeutics Limited, Cambridge (GB)

(72) Inventors: Giles Albert Brown, Cambridge (GB); Miles Stuart Congreve, Cambridge (GB); John Andrew Christopher, Cambridge (GB); Nigel Alan Swain, Cambridge (GB); Sarah Joanne Bucknell, Cambridge (GB); Anne Mary Stephenson, Cambridge (GB); Benjamin Gerald Tehan, Cambridge (GB); Geraint Jones, Nottingham (GB); Mark Mills, Nottingham (GB); Anil Patel, Nottingham (GB); Andrew William Phillips, Nottingham (GB)

(73) Assignee: NXERA PHARMA UK LIMITED, Cambridge (GB)

( * ) Notice: Subject to any disclaimer, the term of this patent is extended or adjusted under 35 U.S.C. 154(b) by 716 days.

(21) Appl. No.: 17/426,301

(22) PCT Filed: Jan. 28, 2020

(86) PCT No.: PCT/GB2020/050182
§ 371 (c)(1),
(2) Date: Jul. 28, 2021

(87) PCT Pub. No.: WO2020/157474
PCT Pub. Date: Aug. 6, 2020

(65) Prior Publication Data
US 2022/0098165 A1    Mar. 31, 2022

(30) Foreign Application Priority Data
Jan. 28, 2019  (GB) .................................. 1901142

(51) Int. Cl.
*C07D 401/04* (2006.01)
*C07D 401/14* (2006.01)

(52) U.S. Cl.
CPC ......... *C07D 401/04* (2013.01); *C07D 401/14* (2013.01)

(58) Field of Classification Search
CPC ..... C07D 401/04; C07D 401/14; A61P 25/22; A61P 25/24; A61P 25/30; A61P 29/00; A61P 35/00
USPC ....................................................... 514/333
See application file for complete search history.

(56) References Cited

FOREIGN PATENT DOCUMENTS

| WO | 2009/003997 A1 | 1/2009 |
|---|---|---|
| WO | 2010/060470 A1 | 6/2010 |
| WO | 2010/060471 A1 | 6/2010 |
| WO | 2013/068935 A1 | 5/2013 |
| WO | 2016/101118 A1 | 6/2016 |
| WO | 2017/039331 A1 | 3/2017 |
| WO | 2017/129829 A1 | 8/2017 |

OTHER PUBLICATIONS

Merlo Pich et al., Published Feb. 13, 2014, Frontiers in Neuroscience, vol. 8, pp. 1-6 (Year: 2014).*
Wang et al., Published Jun. 28, 2018, Frontiers in Molecular Neuroscience, vol. 11, pp. 1-16 (Year: 2018).*
CDC, Picture of America Prevention, https://www.cdc.gov/pictureofamerica/pdfs/picture_of_america_prevention.pdf, accessed Dec. 8, 2023, first published Jul. 2, 2017 (Year: 2017).*
CDC, Picture of America Prevention, https://www.cdc.gov/pictureofamerica/pdfs/picture_of_america_prevention.pdf, accessed Dec. 8, 2023, first published Jul. 2, 2017, Wayback Machine (Year: 2017).*
Lee et al., Published Jun. 26, 2009, Archives of Pharmacal Research, vol. 32, pp. 803-812 (Year: 2009).*
International Search Report and Written Opinion for Application No. PCT/GB2020/050182, dated Mar. 17, 2020, 11 pages.

* cited by examiner

*Primary Examiner* — Yih-Horng Shiao
*Assistant Examiner* — Jaret J Crews
(74) *Attorney, Agent, or Firm* — Barnes & Thornburg LLP

(57) ABSTRACT

The disclosures herein relate to novel compounds of formula (1) and salts thereof, wherein V; W; X; Y; Z; $R_1$; $R_2$; $R_3$; $R_4$ and $R_5$ are defined herein, and their use in treating, preventing, ameliorating, controlling or reducing the risk of neurological or psychiatric disorders associated with orexin receptors.

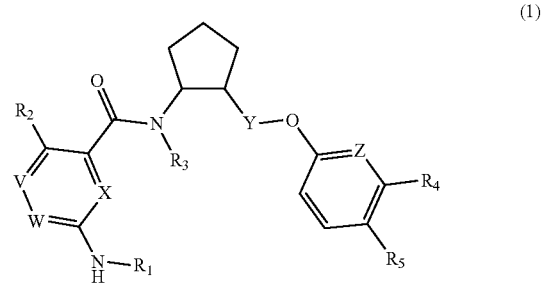

(1)

20 Claims, 1 Drawing Sheet

Preparation of substituted (1S,2S)-2-(phenoxymethyl)cyclopentan-1-amine and (1S,2S)-2-((pyridin-2-yloxy)methyl)cyclopentan-1-amine intermediates
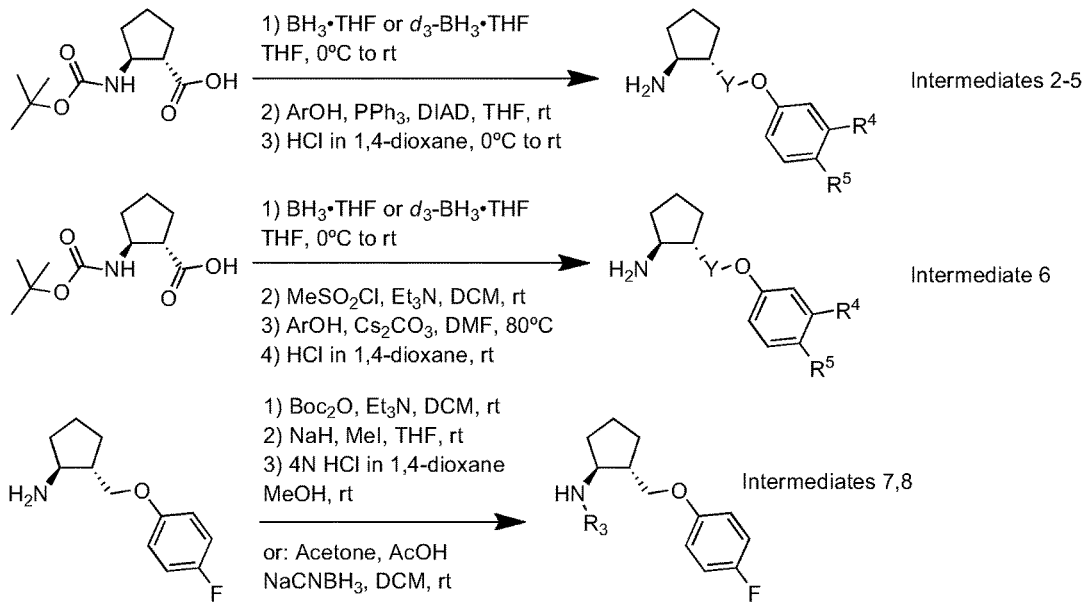
Preparation of examples by amide coupling
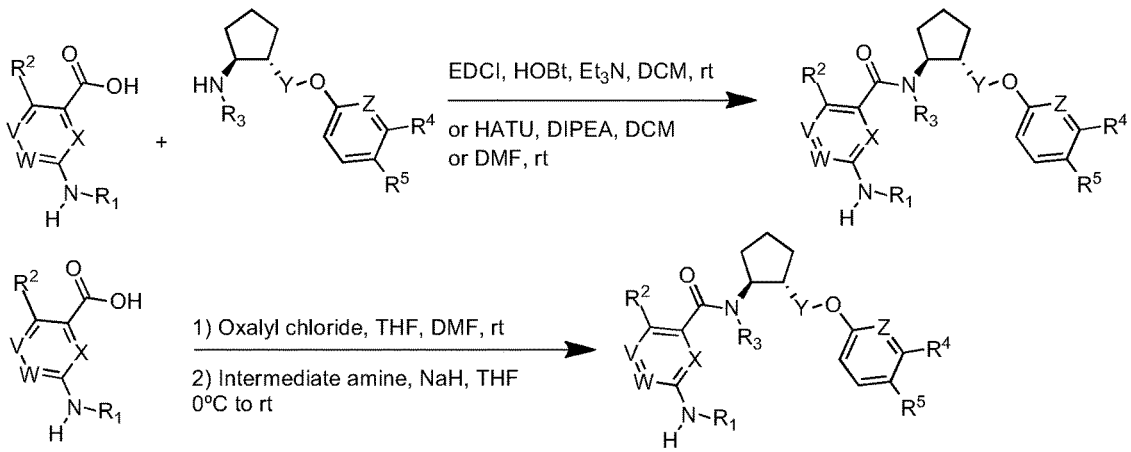
Preparation of examples by Stille coupling
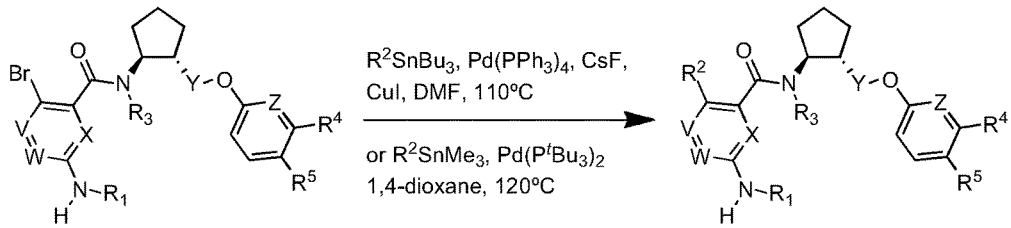
Preparation of examples by S$_N$Ar reaction
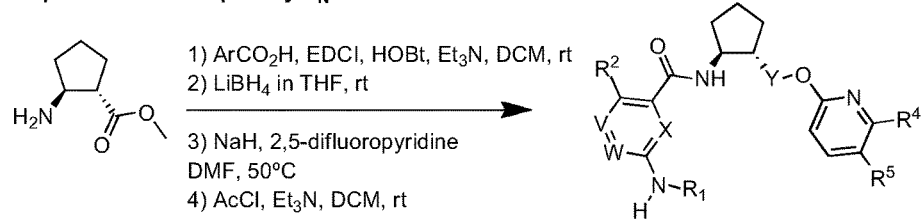

OXEXIN 1 RECEPTOR ANTAGONISTS

CROSS-REFERENCE TO RELATED APPLICATIONS

This application is a 35 U.S.C. § 371 national stage filing of International Application No. PCT/GB2020/050182, filed on Jan. 28, 2020, which claims priority to United Kingdom Application No. 1901142.8, filed on Jan. 28, 2019, the entire contents of each of which are incorporated herein by reference.

This application relates to novel compounds and their use as orexin receptor antagonists. Compounds described herein may be useful in the treatment or prevention of diseases in which orexin receptors are involved. The application is also directed to pharmaceutical compositions comprising these compounds and the manufacture and use of these compounds and compositions in the prevention or treatment of such diseases in which orexin receptors are involved.

BACKGROUND OF THE INVENTION

Neuroanatomical, immunohistochemical and pharmacological evidence suggests that the orexins play important roles in the regulation of a wide variety of physiological functions and complex behaviours. Orexinergic (aka hypocretinergic) neurones are located in the lateral hypothalamus and perifornical area of the mammalian mid-brain and from here they project widely throughout the central nervous system and spinal cord via ascending and descending pathways (Peyron et al, *J. Neurosci.*, 1998, 18, 9996-10015). Orexinergic neurons project to forebrain structures involved in cognition and emotion, such as the cortex, amygdala, hippocampus and septum. In addition, they strongly target ascending neuronal systems involved in the control of arousal, movement, sleep wake cycles and reward processing, notably the noradrenergic locus coeruleus, serotonergic Raphe nuclei, dopaminergic ventral tegmental area and Substantia nigra, cholinergic Pedunculopontine nuclei and histaminergic Tuberomammillary bodies. Similarly, orexinergic neurons project to brain areas involved in the control of feeding in the hypothalamus such as MCH, NPY and leptin positive neurons in the arcuate nucleus (Arrigoni, E et al 2018, *Neuropharmacology* doi: https://doi.org/10.1016/j.neuropharm.2018.11.017). Orexinergic innervation of the dorsal horn of the spinal cord has been reported and evidence for the presence of orexin in peripheral tissues including plasma, sympathetic ganglia, myenteric plexus, endocrine cells of the gastrointestinal tract, adrenal gland, pancreas, placenta, testes, pituitary, kidney, adrenal gland, thyroid and lung amongst others suggest important roles in the regulation of a wide variety of physiological functions.

The orexin peptides orexin A and orexin B are produced in the hypothalamus and exert their effect through activation of the orexin receptors: orexin 1 ($OX_1R$) and orexin 2 ($OX_2R$). $OX_1R$ and $OX_2R$ share 64% amino acid identity. Orexin A and B have equal affinity for $OX_2R$ receptors whilst the affinity of orexin B is around one order of magnitude lower at the $OX_1R$ receptor (Sakurai et al, *Cell*, 1998, 92, 573-585). The orexin receptors are predominantly linked to $G_{q/11}$ G proteins with activation of the receptors leading to activation of the phospholipase C pathway triggering influx of extracellular sodium and calcium and depolarisation of neurones.

Whilst $OX_1R$ and $OX_2R$ show some overlapping distribution, they largely show distinct (but complementary) patterns of distribution within the central nervous system which suggests that each receptor subtype plays different roles in controlling physiological function. Outside of the hypothalamus in the rat brain the highest levels of $OX_1R$ are found in the locus coreleus, tenia tecta, hippocampal formation, dorsal raphe nucleus—areas which have been linked to anxiety, arousal, stress and panic disorders and reward-seeking behaviour. $OX_2R$ is found in the cerebral cortex, nucleus accumbens, subthalamic nucleus, paraventricular thalamic nuclei, anterior pretectal nucleus raphe nuclei and tuberomammillary bodies (Tsujino and Sakurai, *Pharmacol. Rev.*, 2009, 61, 162-176). Orexin receptors are also expressed in peripheral tissues, for example $OX_1R$ can be found in the kidney, testis, thyroid, ovaries, jejunum and adrenal glands (Jöhren et al, *Endocrinology*, 2001, 142, 3324-3331).

Post mortem studies of human brains and the brains of rats trained to self-administer cocaine show functional upregulation of the orexin system. In human post mortem brain 54% more immunohistochemically detected neurons producing orexin were found in the brains of heroin addicts compared to brains from neurologically normal subjects. Similar increases in orexin producing cells could be induced in wild-type mice by administration of morphine (Thannickal et al., 2018 *Sci. Transl. Med.* 10, eaao4953 2018). Furthermore, it has been shown that self-administration of cocaine by rats was accompanied by an increase in number and activity of orexin-expressing neurons within the lateral hypothalamus, an increase which persisted during protracted withdrawal from cocaine. (James M H, et al, *Biological Psychiatry*, https://doi.org/10.1016/j.biopsych.2018.07.022). Taken together these data suggest that an upregulation of orexinergic neuronal activity is associated with drug abuse.

There is substantial preclinical evidence supporting the hypothesis that $OX_1R$ receptor antagonists are efficacious in preclinical models of drug abuse (Boutrel et al, *Front. Behav. Neurosci.*, 2013, 7, 1-10). Intravenous self-administration of cocaine is attenuated in $OX_1R$ knock out mice (Hollander et al, *Front. Behav. Neurosci.*, 2012, 6, 1-9; Muschamp et al, *Proc. Natl. Acad. Sci. U.S.A.*, 2014, e1648-e1655). Intracerebroventricular administration of orexin A leads to a dose-related reinstatement of cocaine seeking and dramatically elevates intracranial self-stimulation thresholds in rodent self-administration studies (Boutrel et al, *Proc. Natl. Acad. Sci. U.S.A.*, 2005, 102, 19168-19173). Administration of a partially selective $OX_1R$ antagonist SB-334867 decreases alcohol (Lawrence et al, Br. *J. Pharmacol.*, 2006, 148, 752-759) and nicotine (Hollander et al, *Proc. Natl. Acad. Sci. U.S.A.*, 2008, 105, 19480-19485) self-administration in rats. In rats intraperitoneal administration of SB-334867 has also been demonstrated to significantly reduce opiate withdrawal symptoms (Laorden et al, *PLoS One*, 2012, 7, e36871; Azizi H, et al. *Neuroscience Letters*, 2010, 482, 255-259).

Selective $OX_1$ receptor antagonists have potential utility therefore to treat a number of Substance Related and Addictive Disorders such as Opioid Use Disorder (including but not limited to Opioid Use Disorder, Opioid Intoxication, Opioid withdrawal, Other Opioid Induced Disorder and Unspecified Opioid Related Disorder): Stimulant Related disorders (including but not limited to Stimulant Use Disorder, Stimulant Intoxication, Stimulant Withdrawal, Other Stimulant Induced Disorders and Unspecified Stimulant Related Disorder where such disorders are associated with the abuse of stimulant drugs exemplified but not limited to cocaine or related structures and, amphetamine-like substances): Caffeine Related Disorders (including but not limited to Caffeine intoxication, Caffeine withdrawal, and Unspecified Caffeine Related disorders): Tobacco Related Disorders (including but not limited to Tobacco Use Disorder, Tobacco Withdrawal, Other Tobacco Induced Disorders and Unspecified Tobacco Related Disorder where such disorders are associated with the use of Tobacco, Tobacco products or the inhalation of nicotine and related compounds): Alcohol Use Disorder, Alcohol Intoxication, Alcohol Withdrawal and Unspecified Alcohol Related Disorder: Cannabis Related Disorders (including but not limited to Cannabis Use Disorder, Cannabis Intoxication, Cannabis Withdrawal, and Unspecified Cannabis Related Disorders whether associated with the use of cannabis, cannabis extracts or synthetic cannabinoids): Hallucinogen Related Disorders (including but not limited to Phencyclidine Use Disorder, Phencyclidine intoxication, Other Hallucinogen Use Disorder, Hallucinogen Persisting Perception Disorder and Unspecified Hallucinogen Related Disorder): Inhalant Related Disorders (including but not limited to Inhalant Use Disorder, Inhalant Intoxication, Other Inhalant Induced Disorders and Unspecified Inhalant Related Disorder where such disorders are associated with the use of compounds such as volatile hydrocarbons, nicotine or nicotine derivatives): Sedative, Hypnotic or Anxiolytic Related Disorders (including but not limited to Use Disorder, Intoxication and Withdrawal). Selective $OX_1$ receptor antagonists also have potential utility to treat a number of Non-Substance Related Disorders such as Gambling Disorder, Internet Gaming Disorder or addiction to sex or internet use.

There is emerging evidence of the orexin systems involvement in anxiety, panic and fear associated learning. Orexin neurones in perifornical and lateral hypothalamic areas are highly reactive to anxiogenic stimuli and optogenetic stimulation of orexin neurons in rodents increases anxiety-like states (Heydend et al, *Physiol. Behav.*, 2013, 130, 182-190). Using two models of panic (sodium lactate infusion and $CO_2$ challenge models) blockade of $OX_1R$ with the highly selective antagonist JNJ-54717793 attenuated panic-like behaviours and cardiovascular responses in rats without altering baseline locomotor or autonomic activity and without sedation (Bonaventure et al, *Front. Pharmacol.*, 2017, 8, 1-13). In a study of 53 medication-free patients with suicidal behaviour increased orexin levels were observed in the cerebral spinal fluid versus control (Johnson et al, *Nat. Med.*, 2010, 16, 111-118) suggesting a link with orexin levels and anxiety.

Selective $OX_1$ receptor antagonists therefore have potential utility to treat Anxiety Disorders (including but not limited to Separation Anxiety Disorder, Specific Phobia, Social Anxiety Disorder (Social Phobia), Panic Disorder, Agoraphobia, Generalized Anxiety Disorder, Substance/Medication Induced Anxiety Disorder and Anxiety Disorder due to Another Medical Condition): Disruptive Mood Dysregulation Disorder, Major Depressive Disorder particularly, but not exclusively, when specified with Anxious Distress, mixed features, atypical features, peripartum onset or seasonal pattern: Persistent Depressive Disorder (Dysthymia) particularly, but not exclusively, when specified with Anxious Distress, mixed features, atypical features, peripartum onset or seasonal pattern: Premenstrual Dysphoric Disorder, Substance/Medication-Induced Depressive Disorder, Other Specified Depressive Disorder or Unspecified Depressive Disorder. Similarly, $OX_1$ receptor antagonists have potential utility to treat the symptoms of Bipolar and Related Disorders (including but not restricted to Bipolar I Disorder and Bipolar II Disorder, particularly, but not exclusively, when these are specified with Anxious Distress, Cyclothymic Disorder, Substance/Medication-induced Bipolar and Related Disorder or Bipolar and Related Disorder due to Another Medical Condition): Schizophrenia Spectrum and other disorders (including but not limited to Schizotypal Personality, Delusional Disorder, Schizophreniform Disorder, Schizophrenia, Schizoaffective Disorder, and Substance/Medication-Induced Psychotic Disorder).

It has been shown that orexin plays a role in mediating the extinction of fear in animal models of stress and trauma (Flores et al, *Trends Neurosci.*, 2015, 38, 550-559). $OX_1$ receptor antagonists therefore have potential utility to treat conditions associated with trauma and stress including but not limited to Post Traumatic Stress Disorder, Acute Stress Disorder, Adjustment Disorders particularly, but not exclusively, when specified with Anxiety or with Mixed Anxiety and Depressed Mood: Obsessive Compulsive and Related Disorders including but not limited to Obsessive Compulsive Disorder, Body Dysmorphia, Trichotillomania, Excoriation and Obsessive Compulsive and Related Disorders due to another medical condition: Feeding and Eating Disorders including but not limited to Binge Eating Disorder, Anorexia Nervosa, Bulimia Nervosa, Cachexia, Obesity and Prader Willi syndrome.

Some Sleep-Wake Disorders may also be treated with selective $OX_1$ receptor antagonists and these disorders include but are not limited to Insomnia Disorder, Rapid Eye Movement Disorder, Sleep disturbances associated with diseases, Sleep Apnoea, Narcolepsy and Circadian Rhythm Sleep-Wake Disorders. Similarly, Neurodegenerative disorders (including but not limited to Parkinson's Disease, Alzheimer's Disease, Dementia, Lewy-body Dementia, Frontotemporal Dementia, Multiple System Atrophy, Perry Syndrome, Klein-Levin Syndrome, Amyotrophic Lateral Sclerosis, Niemann-Pick disease and Multiple Sclerosis): Behavioural Symptoms of neurodegenerative and other disorders (such as Positive Symptoms, Psychosis, Agitation, Anhedonia, Apathy): Movement disorders (such as Akinesias, Dyskinesia, Drug-induced Parkinsonism, Dystonia): other CNS disorders (such as Affective Neurosis, Delirium, Sexual Dysfunction, Psychosexual Dysfunction, Rett Syndrome, Attention-Deficit Disorder, Attention-Deficit Hyperactivity Disorder, Autism (including but not limited to autism spectrum disorder, autism spectrum condition, atypical autism, classic autism, Kanner autism, pervasive developmental disorder, high-functioning autism and Asperger syndrome), Fragile X syndrome, Disruptive behaviour disorder, Severe mental retardation, Vomiting.

Pathological conditions showing reduced metabolic activity or a decrease in resting energy expenditure as a percentage of total fat-free mass may be amenable to treatment with selective $OX_1$ receptor antagonists, such conditions include, but are not limited to Diabetes, impaired glucose tolerance; Cardiovascular Disease including but not limited to Acute and Congestive Heart Failure, Hypotension, Hypertension, Angina Pectoris, Myocardial infarction.

Hypothalamic/pituitary disorders may be amenable to treatment with selective $OX_1$ receptor antagonists, including but not limited to Cushing's Syndrome/disease, Basophile adenoma, Prolactinoma, hyperprolactinemia, Hypophysis Tumour/adenoma, Hypothalamic diseases, Froehlich's syndrome, Adenohypophysis disease, Hypophysis disease, Adenohypophysis hypofunction, Adenohypophysis hyperfunction, Hypothalamic hypogonadism, Kallman's syndrome (anosmia, hyposmia), functional or psychogenic Amenorrhea, Hypopituitarism, Hypothalamic Hypothyroidism, Hypothalamic-adrenal dysfunction, Idiopathic Hyperprolactinemia, Hypothalamic Disorders of growth hormone deficiency, Idiopathic growth deficiency, Dwarfism, Gigantism, Acromegaly.

Pain disorders may be amenable to treatment with selective $OX_1$ receptor antagonists, including but not limited to Neuropathic pain, Restless Leg Syndrome, Migraine, Cluster headache, Tension-type headache, Trigeminal autonomic Cephalalgias, Hemicrania Continua, Trigeminal neuralgia, other headache disorders, pain, enhanced or exaggerated sensitivity to pain such as Hyperalgesia, Causalgia, and Allodynia, Acute pain, Burn pain, Atypical facial pain, Back pain, Complex regional pain syndrome I and II, Arthritic pain, Sports injury pain, pain related to infection e.g. HIV, Post-chemotherapy pain, Post-stroke pain, Post-operative pain, neuralgia, conditions associated with Visceral pain such as Irritable bowel syndrome, and Angina pain; Inflammatory disorders (including Inflammatory bowel disease), Renal/urinary disorders (including urinary retention, benign prostatic hypertrophy, chronic renal failure, renal disease); Respiratory disorders (such as Chronic obstructive pulmonary disease, Asthma).

Orexin-A/$OX_1$ receptor interactions have been shown to modulate activity of the androgen receptor (Valiante et al, *Biochem. Biophys. Res Comm.*, 2015, 464, 1290-1296) which regulates the onset and progression of prostate cancer, suggesting that selective $OX_1$ receptor antagonists have potential therapeutic benefit in treating some forms of cancer including, but not limited to, Prostate cancer, Liver Cancer, Colon cancer, Endometrial cancer, Pancreatic cancer and cancers associated with other organs of the body including the central nervous system and peripheral nervous system.

SUMMARY OF THE INVENTION

The invention relates to novel compounds. The invention also relates to the use of novel compounds as antagonists of orexin receptor $OX_1$. The invention further relates to the use of novel compounds in the manufacture of medicaments for use as orexin receptor $OX_1$ antagonists or for the treatment of orexin system dysfunction. The invention further relates to compounds, compositions and medicaments for the treatment of neurological or psychiatric disorders. Embodiments of the invention may be compounds of the formula (1):

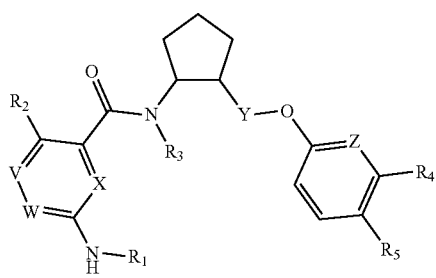

(1)

or a salt thereof, wherein
V is N, CH or CF;
W is N, CH or CF;
X is N, CH or CF;
Y is $CH_2$;
Z is N, CH or CF;
$R_1$ is selected from H, a group $C(O)R_6$ and $C_{1-6}$ alkyl optionally substituted with one or more halogens or hydroxy groups;

$R_2$ is a 5 or 6-membered heteroaryl ring containing two or three nitrogen atoms which is optionally substituted with one or more fluorine atoms;
$R_3$ is H or $C_{1-3}$ alkyl;
$R_4$ is H or a halogen;
$R_5$ is H or a halogen;
$R_6$ is optionally substituted $C_{1-6}$ alkyl, optionally substituted $C_{1-6}$ alkoxy or optionally substituted $C_{3-6}$ cycloalkyl, wherein the optional substituent is OMe or one or more fluorine atoms.

The compounds may be for use as antagonists of orexin receptor $OX_1$. The compounds may be used in the manufacture of medicaments. The compounds or medicaments may be for use in treating, preventing, ameliorating, controlling or reducing the risk of neurological or psychiatric disorders.

The compounds or medicaments may be for use in the treatment or prevention of substance related and addictive disorders (including opioid use disorder, opioid intoxication, opioid withdrawal, other opioid induced disorder, unspecified opioid related disorder, stimulant use disorder, stimulant intoxication, stimulant withdrawal, other stimulant induced disorders, unspecified stimulant related disorder, caffeine related disorders, caffeine intoxication, caffeine withdrawal, unspecified caffeine related disorders, tobacco related disorders, tobacco use disorder, tobacco withdrawal, other tobacco induced disorders, unspecified tobacco related disorder, alcohol use disorder, alcohol intoxication, alcohol withdrawal, unspecified alcohol related disorder, cannabis related disorders, cannabis use disorder, cannabis intoxication, cannabis withdrawal, unspecified cannabis related disorders, hallucinogen related disorders, phencyclidine use disorder, phencyclidine intoxication, other hallucinogen use disorder, hallucinogen persisting perception disorder, unspecified hallucinogen related disorder, inhalant related disorders, inhalant use disorder, inhalant intoxication, other inhalant induced disorders, unspecified inhalant related disorder, sedative, hypnotic or anxiolytic related disorders (including use disorder, intoxication and withdrawal), gambling disorder, internet gaming disorder, addiction to sex or internet use), anxiety disorders (including separation anxiety disorder, specific phobia, social anxiety disorder (social phobia), panic disorder, agoraphobia, generalized anxiety disorder, substance/medication induced anxiety disorder, anxiety disorder due to another medical condition), disruptive mood dysregulation disorder, major depressive disorder (including when specified with anxious distress, mixed features, atypical features, peripartum onset or seasonal pattern), persistent depressive disorder (dysthymia) (including when specified with anxious distress, mixed features, atypical features, peripartum onset or seasonal pattern), premenstrual dysphoric disorder, substance/medication-induced depressive disorder, other specified depressive disorder, unspecified depressive disorder bipolar and related disorders (including bipolar I disorder and bipolar II disorder, particularly, but not exclusively, when these are specified with anxious distress, cyclothymic disorder, substance/medication-induced bipolar and related disorder or bipolar and related disorder due to another medical condition), schizophrenia spectrum and other disorders (including schizotypal personality, delusional disorder, schizophreniform disorder, schizophrenia, schizoaffective disorder, and substance/medication-induced psychotic disorder), conditions associated with trauma and stress (including post traumatic stress disorder, acute stress disorder, adjustment disorders (including when specified with anxiety or with mixed anxiety and depressed mood), obsessive compulsive and related disorders (including obsessive compulsive disorder, body dysmorphia, trichotillomania, excoriation and obsessive-compulsive and related disorders due to another medical condition), feeding and eating disorders (including binge eating disorder, anorexia nervosa, bulimia nervosa, cachexia, obesity, Prader Willi syndrome), sleep-wake disorders, neurodegenerative disorders (including dementia), behavioural symptoms of neurodegenerative and other disorders, movement disorders, diabetes, impaired glucose tolerance, cardiovascular disease, diseases related to modulation of sympathetic outflow including hypertension, hypothalamic/pituitary disorders, neuropathic pain, restless leg syndrome, migraine, cluster headache, tension-type headache, trigeminal autonomic cephalalgias, hemicrania continua, trigeminal neuralgia, other headache disorders, hyperalgesia, pain, hyperalgesia, causalgia, and allodynia, acute pain, burn pain, atypical facial pain, back pain, complex regional pain syndrome I and II, arthritic pain, sports injury pain, pain related to infection, irritable bowel syndrome, angina pain, inflammatory disorders, renal/urinary disorders, respiratory disorders, cancer (including prostate cancer, liver cancer, colon cancer, endometrial cancer, pancreatic cancer and cancers associated with other organs of the body including the central nervous system and peripheral nervous system).

The compounds or medicaments may be for use in the treatment or prevention of substance related and addictive disorders, post traumatic stress disorder, panic disorder, major depressive disorder with anxious distress, diseases related to modulation of sympathetic outflow including hypertension, pain, headache, cancer.

The compounds may be formulated as a pharmaceutical composition comprising the compounds and a pharmaceutically acceptable excipient.

The compounds may be produced using any chemical synthesis method.

BRIEF DESCRIPTION OF THE DRAWINGS

FIG. 1 depicts synthetic schemes for compounds of the present disclosure.

DETAILED DESCRIPTION OF THE INVENTION

The invention relates to novel compounds. The invention also relates to the use of novel compounds as antagonists of orexin receptor $OX_1$. The invention further relates to the use of novel compounds in the manufacture of medicaments for use as orexin receptor $OX_1$ antagonists or for the treatment of orexin system dysfunction. The invention further relates to compounds, compositions and medicaments which are selective $OX_1$ receptor antagonists.

The invention further relates to compounds, compositions and medicaments for the treatment of Substance Related and Addictive Disorders such as Opioid Use Disorder (including but not limited to Opioid Use Disorder, Opioid Intoxication, Opioid withdrawal, Other Opioid Induced Disorder and Unspecified Opioid Related Disorder): Stimulant Related disorders (including but not limited to Stimulant Use Disorder, Stimulant Intoxication, Stimulant Withdrawal, Other Stimulant Induced Disorders and Unspecified Stimulant Related Disorder where such disorders are associated with the abuse of stimulant drugs exemplified but not limited to cocaine or related structures and, amphetamine-like substances): Caffeine Related Disorders (including but not limited to Caffeine intoxication, Caffeine withdrawal, and Unspecified Caffeine Related disorders): Tobacco Related Disorders (including but not limited to Tobacco Use Disorder, Tobacco Withdrawal, Other Tobacco Induced Disorders and Unspecified Tobacco Related Disorder where such disorders are associated with the use of Tobacco, Tobacco products or the inhalation of nicotine and related compounds): Alcohol Use Disorder, Alcohol Intoxication, Alcohol Withdrawal and Unspecified Alcohol Related Disorder: Cannabis Related Disorders (including but not limited to Cannabis Use Disorder, Cannabis Intoxication, Cannabis Withdrawal, and Unspecified Cannabis Related Disorders whether associated with the use of cannabis, cannabis extracts or synthetic cannabinoids): Hallucinogen Related Disorders (including but not limited to Phencyclidine Use Disorder, Phencyclidine intoxication, Other Hallucinogen Use Disorder, Hallucinogen Persisting Perception Disorder and Unspecified Hallucinogen Related Disorder): Inhalant Related Disorders (including but not limited to Inhalant Use Disorder, Inhalant Intoxication, Other Inhalant Induced Disorders and Unspecified Inhalant Related Disorder where such disorders are associated with the use of compounds such as volatile hydrocarbons, nicotine or nicotine derivatives): Sedative, Hypnotic or Anxiolytic Related Disorders (including but not limited to Use Disorder, Intoxication and Withdrawal). Selective $OX_1$ receptor antagonists also have potential utility to treat a number of Non-Substance Related Disorders such as Gambling Disorder, Internet Gaming Disorder or addiction to sex or internet use.

The invention further relates to compounds, compositions and medicaments for the treatment of Anxiety Disorders (including but not limited to Separation Anxiety Disorder, Specific Phobia, Social Anxiety Disorder (Social Phobia), Panic Disorder, Agoraphobia, Generalized Anxiety Disorder, Substance/Medication Induced Anxiety Disorder and Anxiety Disorder due to Another Medical Condition): Disruptive Mood Dysregulation Disorder, Major Depressive Disorder particularly, but not exclusively, when specified with Anxious Distress, mixed features, atypical features, peripartum onset or seasonal pattern: Persistent Depressive Disorder (Dysthymia) particularly, but not exclusively, when specified with Anxious Distress, mixed features, atypical features, peripartum onset or seasonal pattern: Premenstrual Dysphoric Disorder, Substance/Medication-Induced Depressive Disorder, Other Specified Depressive Disorder or Unspecified Depressive Disorder. Similarly, $OX_1$ receptor antagonists have potential utility to treat the symptoms of Bipolar and Related Disorders (including but not restricted to Bipolar I Disorder and Bipolar II Disorder, particularly, but not exclusively, when these are specified with Anxious Distress, Cyclothymic Disorder, Substance/Medication-induced Bipolar and Related Disorder or Bipolar and Related Disorder due to Another Medical Condition): Schizophrenia Spectrum and other disorders (including but not limited to Schizotypal Personality, Delusional Disorder, Schizophreniform Disorder, Schizophrenia, Schizoaffective Disorder, and Substance/Medication-Induced Psychotic Disorder).

The invention further relates to compounds, compositions and medicaments for the treatment of conditions associated with trauma and stress including but not limited to Post Traumatic Stress Disorder, Acute Stress Disorder, Adjustment Disorders particularly, but not exclusively, when specified with Anxiety or with Mixed Anxiety and Depressed Mood: Obsessive Compulsive and Related Disorders including but not limited to Obsessive Compulsive Disorder, Body Dysmorphia, Trichotillomania, Excoriation and Obsessive Compulsive and Related Disorders due to another medical condition: Feeding and Eating Disorders including but not limited to Binge Eating Disorder, Anorexia Nervosa, Bulimia Nervosa, Cachexia, Obesity and Prader Willi syndrome.

The invention further relates to compounds, compositions and medicaments for the treatment of Sleep-Wake Disorders. These disorders include but are not limited to Insomnia Disorder, Rapid Eye Movement Disorder, Sleep disturbances associated with diseases, Sleep Apnoea, Narcolepsy and Circadian Rhythm Sleep-Wake Disorders. Similarly, Neurodegenerative disorders (including but not limited to Parkinson's Disease, Alzheimer's Disease, Dementia, Lewy-body Dementia, Frontotemporal Dementia, Multiple System Atrophy, Perry Syndrome, Klein-Levin Syndrome, Amyotrophic Lateral Sclerosis, Niemann-Pick disease and Multiple Sclerosis): Behavioural Symptoms of neurodegenerative and other disorders (such as Positive Symptoms, Psychosis, Agitation, Anhedonia, Apathy): Movement disorders (such as Akinesias, Dyskinesia, Drug-induced Parkinsonism, Dystonia): other CNS disorders (such as Affective Neurosis, Delirium, Sexual Dysfunction, Psychosexual Dysfunction, Rett Syndrome, Attention-Deficit Disorder, Attention-Deficit Hyperactivity Disorder, Autism (including but not limited to autism spectrum disorder, autism spectrum condition, atypical autism, classic autism, Kanner autism, pervasive developmental disorder, high-functioning autism and Asperger syndrome), Fragile X syndrome, Disruptive behaviour disorder, Severe mental retardation, Vomiting.

The invention further relates to compounds, compositions and medicaments for the treatment of Pathological conditions showing reduced metabolic activity or a decrease in resting energy expenditure as a percentage of total fat-free mass. Such conditions include, but are not limited to Diabetes, impaired glucose tolerance; Cardiovascular Disease including but not limited to Acute and Congestive Heart Failure, Hypotension, Hypertension, Angina Pectoris, Myocardial infarction.

The invention further relates to compounds, compositions and medicaments for the treatment of Hypothalamic/pituitary disorders, including but not limited to Cushing's Syndrome/disease, Basophile adenoma, Prolactinoma, hyperprolactinemia, Hypophysis Tumour/adenoma, Hypothalamic diseases, Froehlich's syndrome, Adenohypophysis disease, Hypophysis disease, Adenohypophysis hypofunction, Adenohypophysis hyperfunction, Hypothalamic hypogonadism, Kallman's syndrome (anosmia, hyposmia), functional or psychogenic Amenorrhea, Hypopituitarism, Hypothalamic Hypothyroidism, Hypothalamic-adrenal dysfunction, Idiopathic Hyperprolactinemia, Hypothalamic Disorders of growth hormone deficiency, Idiopathic growth deficiency, Dwarfism, Gigantism, Acromegaly.

The invention further relates to compounds, compositions and medicaments for the treatment of Pain disorders, including but not limited to Neuropathic pain, Restless Leg Syndrome, Migraine, Cluster headache, Tension-type headache, Trigeminal autonomic Cephalalgias, Hemicrania Continua, Trigeminal neuralgia, other headache disorders, pain, enhanced or exaggerated sensitivity to pain such as Hyperalgesia, Causalgia, and Allodynia, Acute pain, Burn pain, Atypical facial pain, Back pain, Complex regional pain syndrome I and II, Arthritic pain, Sports injury pain, pain related to infection e.g. HIV, Post-chemotherapy pain, Post-stroke pain, Post-operative pain, neuralgia, conditions associated with Visceral pain such as Irritable bowel syndrome, and Angina pain; Inflammatory disorders (including Inflammatory bowel disease), Renal/urinary disorders (including urinary retention, benign prostatic hypertrophy, chronic renal failure, renal disease); Respiratory disorders (such as Chronic obstructive pulmonary disease, Asthma).

The invention further relates to compounds, compositions and medicaments for the treatment of androgen receptor mediated cancers, including, but not limited to, Prostate cancer, Liver Cancer, Colon cancer, Endometrial cancer, Pancreatic cancer and cancers associated with other organs of the body including the central nervous system and peripheral nervous system.

Compounds of the invention include compounds according to the formula (1):

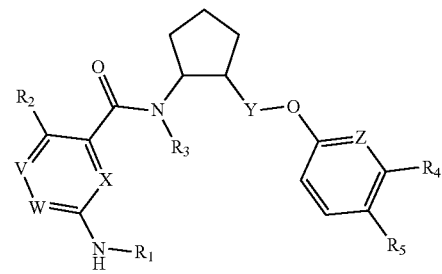

(1)

or a salt thereof, wherein
V is N, CH or CF;
W is N, CH or CF;
X is N, CH or CF;
Y is $CH_2$;
Z is N, CH or CF;
$R_1$ is selected from H, a group $C(O)R_6$ and $C_{1-6}$ alkyl optionally substituted with one or more halogens or hydroxy groups;
$R_2$ is a 5 or 6-membered heteroaryl ring containing two or three nitrogen atoms which is optionally substituted with one or more fluorine atoms;
$R_3$ is H or $C_{1-3}$ alkyl;
$R_4$ is H or a halogen;
$R_5$ is H or a halogen;
$R_6$ is optionally substituted $C_{1-6}$ alkyl, optionally substituted $C_{1-6}$ alkoxy or optionally substituted $C_{3-6}$ cycloalkyl, wherein the optional substituent is OMe or one or more fluorine atoms.

Compounds of the invention include compounds according to the formula (2):

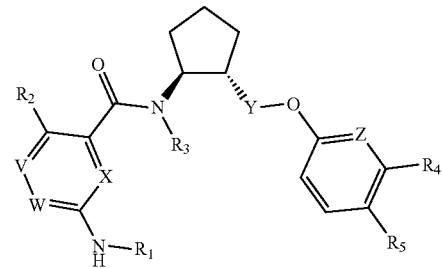

(2)

or a salt thereof, wherein
V is N, CH or CF;
W is N, CH or CF;
X is N, CH or CF;
Y is $CH_2$;
Z is N, CH or CF;

$R_1$ is selected from H, a group $C(O)R_6$ and $C_{1-6}$ alkyl optionally substituted with one or more halogens or hydroxy groups;

$R_2$ is a 5 or 6-membered heteroaryl ring containing two or three nitrogen atoms which is optionally substituted with one or more fluorine atoms;

$R_3$ is H or $C_{1-3}$ alkyl;

$R_4$ is H or a halogen;

$R_5$ is H or a halogen;

$R_6$ is optionally substituted $C_{1-6}$ alkyl, optionally substituted $C_{1-6}$ alkoxy or optionally substituted $C_{3-6}$ cycloalkyl, wherein the optional substituent is OMe or one or more fluorine atoms.

Specific embodiments include the following substituents, which can be combined in any particular combination without limitation:

V can be N. V can be CH. V can be CF. Where V is N, W and X can be CH or CF rather than N, thereby V and W or V and X are not both N.

W can be N. W can be CH. W can be CF. Where W is N, V and X can be CH or CF rather than N, thereby W and V or W and X are not both N.

X can be N. X can be CH. X can be CF. Where X is N, V and W can be CH or CF rather than N, thereby X and V or X and W are not both N.

Y can be $CH_2$. Y can be $CD_2$.

Z can be CH. Z can be CF. Z can be N.

$R_1$ can be H. $R_1$ can be a group $C(O)R_6$. $R_1$ can be $C_{1-6}$ alkyl. $R_1$ can be $C_{1-6}$ alkyl optionally substituted with one or more halogens or hydroxy groups. $R_1$ can be $CH_2CHF_2$. $R_1$ can be $CH_2CH_2OH$. $R_1$ can be $C(O)OMe$. $R_1$ can be $C(O)CH_3$. $R_1$ can be $C(O)CHF_2$. $R_1$ can be $C(O)$cyclopropyl. $R_1$ can be $C(O)CH_2OMe$.

$R_2$ can be a 5 or 6-membered heteroaryl ring containing two or three nitrogen atoms which is substituted with one or more fluorine atoms.

$R_2$ can be a 5-membered heteroaryl ring containing three nitrogen atoms.

$R_2$ can be a 6-membered heteroaryl ring containing two nitrogen atoms.

$R_2$ can be a triazole ring. $R_2$ can be a 1,2,3-triazole ring. $R_2$ can be a pyrimidine ring.

$R_2$ can be a pyrimidine ring substituted with F.

$R_2$ can be selected from the group consisting of:

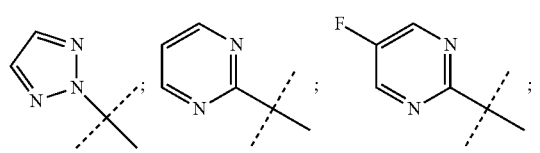

$R_2$ can be:

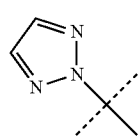

$R_2$ can be:

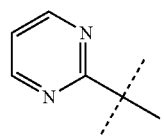

$R_2$ can be:

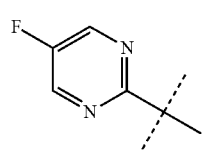

$R_3$ can be H. $R_3$ can be $C_{1-3}$ alkyl. $R_3$ can be Me. $R_3$ can be isopropyl.

$R_4$ can be H. $R_4$ can be a halogen. $R_4$ can be F.

$R_5$ can be H. $R_5$ can be a halogen. $R_5$ can be F. $R_5$ can be Cl.

The compound can be selected from the group consisting of:

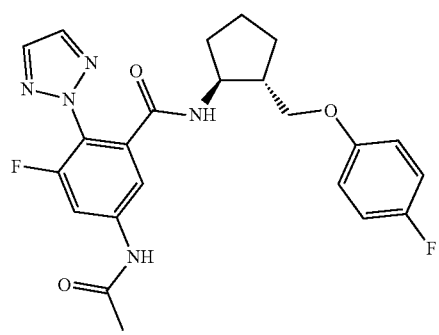

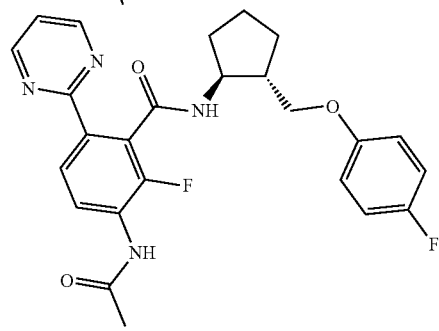

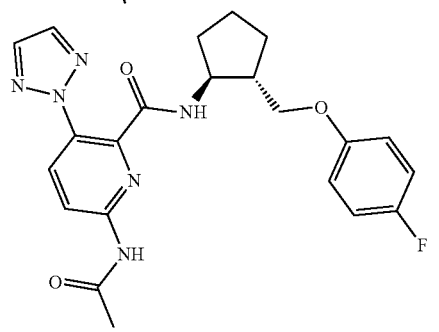

-continued
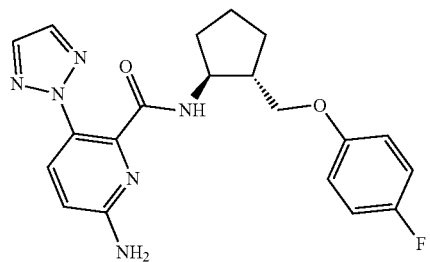
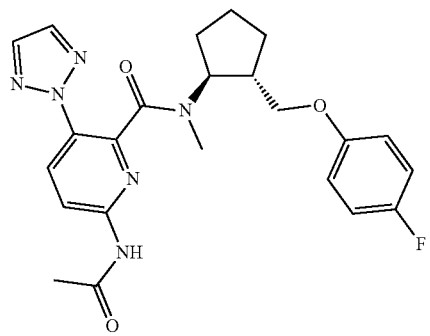
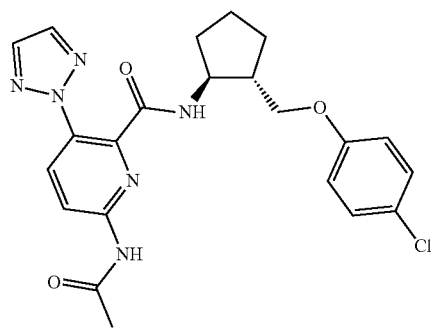
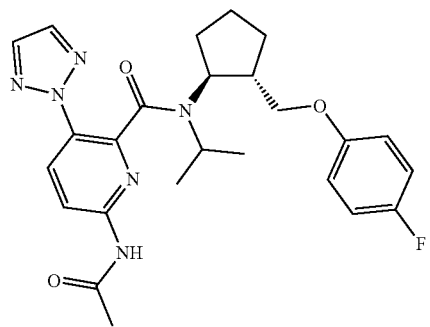
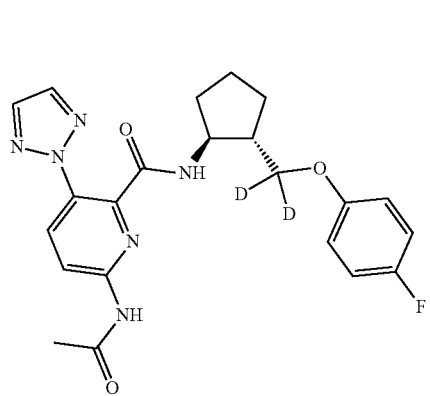
-continued
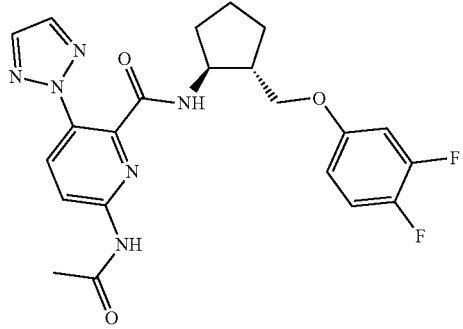
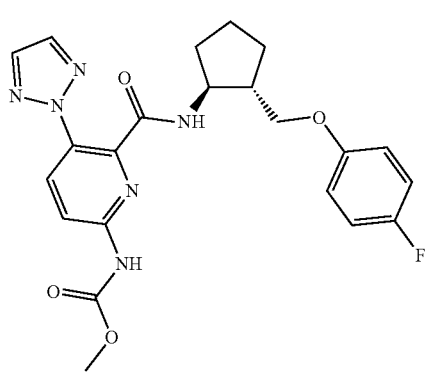
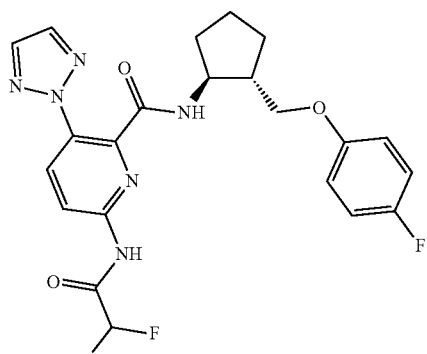
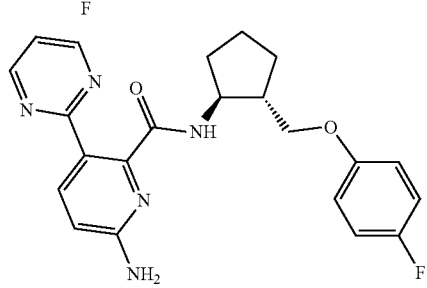
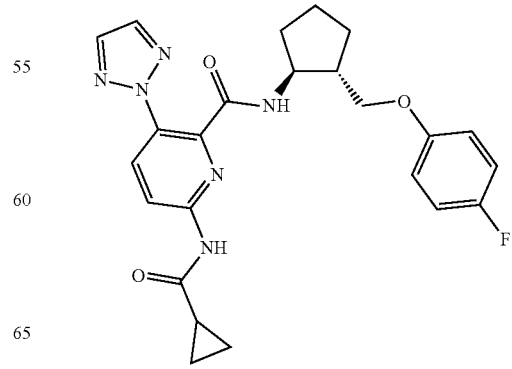

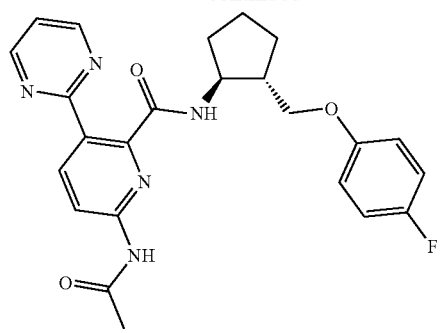
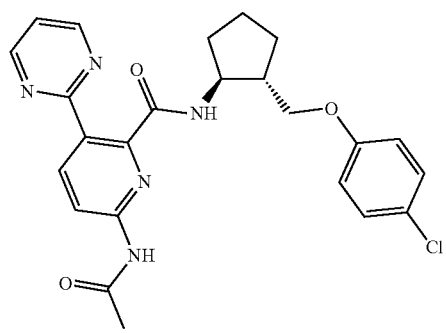
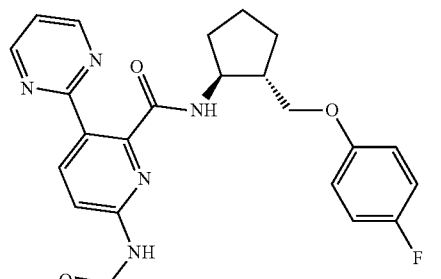
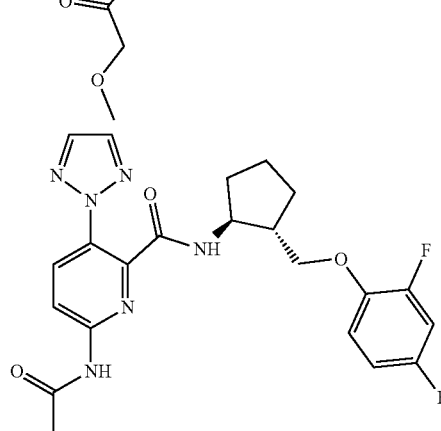
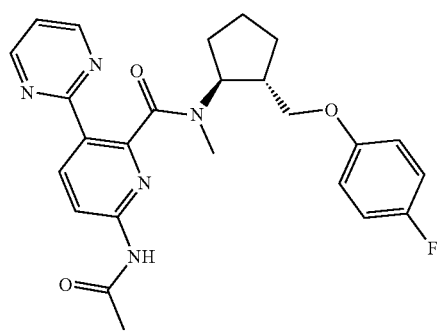
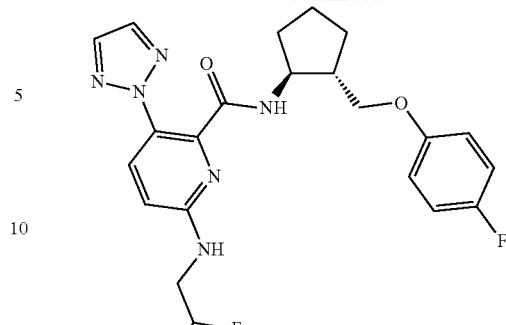
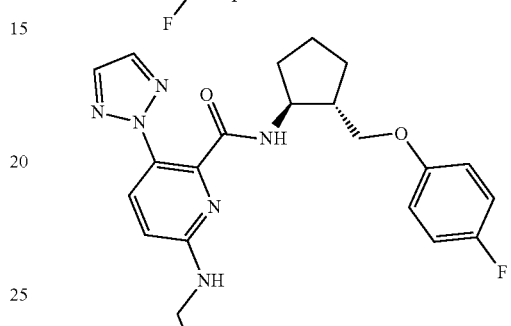
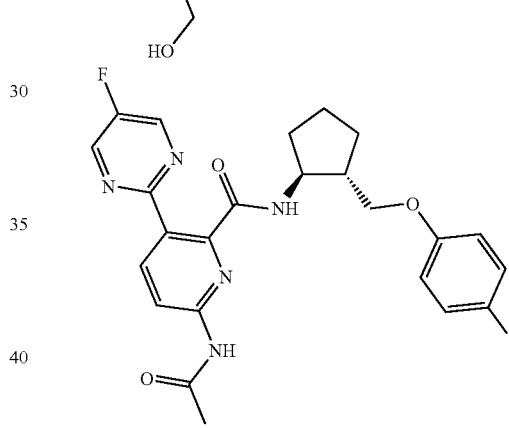
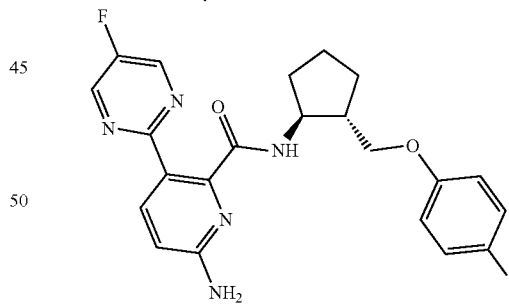
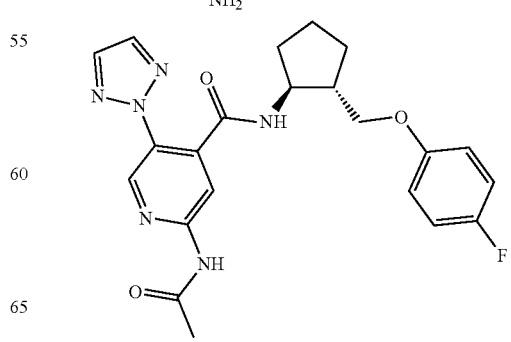

-continued

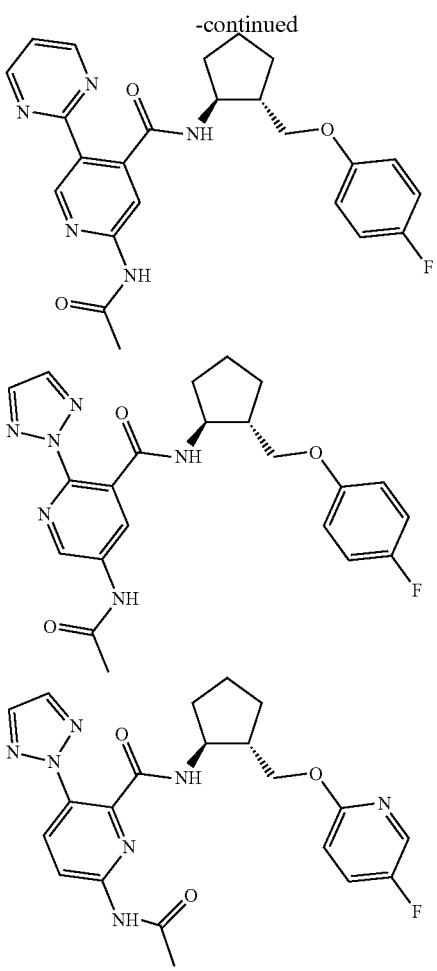

The compound can be selected from the group consisting of:
5-acetamido-3-fluoro-N-[(1S,2S)-2-[(4-fluorophenoxy) methyl]cyclopentyl]-2-(triazol-2-yl)benzamide;
3-acetamido-2-fluoro-N-[(1S,2S)-2-[(4-fluorophenoxy) methyl]cyclopentyl]-6-pyrimidin-2-yl-benzamide;
6-acetamido-N-[(1S,2S)-2-[(4-fluorophenoxy)methyl]cyclopentyl]-3-(triazol-2-yl)pyridine-2-carboxamide;
6-amino-N-[(1S,2S)-2-[(4-fluorophenoxy)methyl]cyclopentyl]-3-(triazol-2-yl)pyridine-2-carboxamide;
6-acetamido-N-[(1S,2S)-2-[(4-fluorophenoxy)methyl]cyclopentyl]-N-methyl-3-(triazol-2-yl)pyridine-2-carboxamide;
6-acetamido-N-[(1S,2S)-2-[(4-chlorophenoxy)methyl] cyclopentyl]-3-(triazol-2-yl)pyridine-2-carboxamide;
6-acetamido-N-[(1S,2S)-2-[(4-fluorophenoxy)methyl]cyclopentyl]-N-isopropyl-3-(triazol-2-yl)pyridine-2-carboxamide;
6-acetamido-N-[(1S,2S)-2-[dideuterio-(4-fluorophenoxy) methyl]cyclopentyl]-3-(triazol-2-yl)pyridine-2-carboxamide;
6-acetamido-N-[(1S,2S)-2-[(3,4-difluorophenoxy) methyl]cyclopentyl]-3-(triazol-2-yl)pyridine-2-carboxamide;
methyl N-[6-[[(1S,2S)-2-[(4-fluorophenoxy)methyl]cyclopentyl]carbamoyl]-5-(triazol-2-yl)-2-pyridyl]carbamate;
6-[(2,2-difluoroacetyl)amino]-N-[(1S,2S)-2-[(4-fluorophenoxy)methyl]cyclopentyl]-3-(triazol-2-yl)pyridine-2-carboxamide;
6-amino-N-[(1S,2S)-2-[(4-fluorophenoxy)methyl]cyclopentyl]-3-pyrimidin-2-yl-pyridine-2-carboxamide;
6-(cyclopropanecarbonylamino)-N-[(1S,2S)-2-[(4-fluorophenoxy)methyl]cyclopentyl]-3-(triazol-2-yl)pyridine-2-carboxamide;
6-acetamido-N-[(1S,2S)-2-[(4-fluorophenoxy)methyl]cyclopentyl]-3-pyrimidin-2-yl-pyridine-2-carboxamide;
6-acetamido-N-[(1S,2S)-2-[(4-chlorophenoxy)methyl] cyclopentyl]-3-pyrimidin-2-yl-pyridine-2-carboxamide;
N-[(1S,2S)-2-[(4-fluorophenoxy)methyl]cyclopentyl]-6-[(2-methoxyacetyl)amino]-3-pyrimidin-2-yl-pyridine-2-carboxamide;
6-acetamido-N-[(1S,2S)-2-[(2,4-difluorophenoxy) methyl]cyclopentyl]-3-(triazol-2-yl)pyridine-2-carboxamide;
6-acetamido-N-[(1S,2S)-2-[(4-fluorophenoxy)methyl]cyclopentyl]-N-methyl-3-pyrimidin-2-yl-pyridine-2-carboxamide;
6-(2,2-difluoroethylamino)-N-[(1S,2S)-2-[(4-fluorophenoxy)methyl]cyclopentyl]-3-(triazol-2-yl)pyridine-2-carboxamide;
N-[(1S,2S)-2-[(4-fluorophenoxy)methyl]cyclopentyl]-6-(2-hydroxyethylamino)-3-(triazol-2-yl)pyridine-2-carboxamide;
6-acetamido-N-[(1S,2S)-2-[(4-fluorophenoxy)methyl]cyclopentyl]-3-(5-fluoropyrimidin-2-yl)pyridine-2-carboxamide;
6-amino-N-[(1S,2S)-2-[(4-fluorophenoxy)methyl]cyclopentyl]-3-(5-fluoropyrimidin-2-yl)pyridine-2-carboxamide;
2-acetamido-N-[(1S,2S)-2-[(4-fluorophenoxy)methyl]cyclopentyl]-5-(triazol-2-yl)pyridine-4-carboxamide;
2-acetamido-N-[(1S,2S)-2-[(4-fluorophenoxy)methyl]cyclopentyl]-5-pyrimidin-2-yl-pyridine-4-carboxamide;
5-acetamido-N-[(1S,2S)-2-[(4-fluorophenoxy)methyl]cyclopentyl]-2-(triazol-2-yl)pyridine-3-carboxamide;
6-acetamido-N-[(1S,2S)-2-[(5-fluoro-2-pyridyl)oxymethyl]cyclopentyl]-3-(triazol-2-yl)pyridine-2-carboxamide.

Definitions

In this application, the following definitions apply, unless indicated otherwise.

The term "treatment", in relation to the uses of any of the compounds described herein, including those of the formula (1) or formula (2), is used to describe any form of intervention where a compound is administered to a subject suffering from, or at risk of suffering from, or potentially at risk of suffering from the disease or disorder in question. Thus, the term "treatment" covers both preventative (prophylactic) treatment and treatment where measurable or detectable symptoms of the disease or disorder are being displayed.

The term "effective therapeutic amount" as used herein (for example in relation to methods of treatment of a disease or condition) refers to an amount of the compound which is effective to produce a desired therapeutic effect. For example, if the condition is pain, then the effective therapeutic amount is an amount sufficient to provide a desired level of pain relief. The desired level of pain relief may be, for example, complete removal of the pain or a reduction in the severity of the pain.

To the extent that any of the compounds described have chiral centres, the present invention extends to all optical isomers of such compounds, whether in the form of racemates or resolved enantiomers. The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

Salts or pharmaceutically acceptable salts that may be mentioned include acid addition salts and base addition salts. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Examples of pharmaceutically acceptable salts include acid addition salts derived from mineral acids and organic acids, and salts derived from metals such as sodium, magnesium, or preferably, potassium and calcium.

Examples of acid addition salts include acid addition salts formed with acetic, 2,2-dichloroacetic, adipic, alginic, aryl sulfonic acids (e.g. benzenesulfonic, naphthalene-2-sulfonic, naphthalene-1,5-disulfonic and p-toluenesulfonic), ascorbic (e.g. L-ascorbic), L-aspartic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (−)-L-malic), malonic, (±)-DL-mandelic, metaphosphoric, methanesulfonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulfuric, tannic, tartaric (e.g. (+)-L-tartaric), thiocyanic, undecylenic and valeric acids.

Particular examples of salts are salts derived from mineral acids such as hydrochloric, hydrobromic, phosphoric, metaphosphoric, nitric and sulfuric acids; from organic acids, such as tartaric, acetic, citric, malic, lactic, fumaric, benzoic, glycolic, gluconic, succinic, arylsulfonic acids; and from metals such as sodium, magnesium, or preferably, potassium and calcium. Also encompassed are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates. For a more detailed discussion of solvates and the methods used to make and characterise them, see Bryn et al, Solid-State Chemistry of Drugs, Second Edition, published by SSCI, Inc of West Lafayette, IN, USA, 1999, ISBN 0-967-06710-3.

The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may take the form, for example, of tablets, dragees, powders, elixirs, syrups, liquid preparations including suspensions, sprays, inhalants, tablets, lozenges, emulsions, solutions, cachets, granules, capsules and suppositories, as well as liquid preparations for injections, including liposome preparations.

The compounds of the invention may contain one or more isotopic substitutions, and a reference to a particular element includes within its scope all isotopes of the element. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O. In an analogous manner, a reference to a particular functional group also includes within its scope isotopic variations, unless the context indicates otherwise. For example, a reference to an alkyl group such as an ethyl group or an alkoxy group such as a methoxy group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group) or a methoxy group in which all three hydrogen atoms are in the deuterium isotopic form (a trideuteromethoxy group). A group shown for example as $CH_2$ may be $CD_2$ or CHD. The isotopes may be radioactive or non-radioactive.

Therapeutic dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage may be divided and administered in portions during the day if desired.

The magnitude of an effective dose of a compound will, of course, vary with the nature of the severity of the condition to be treated and with the particular compound and its route of administration. The selection of appropriate dosages is within the ability of one of ordinary skill in this art, without undue burden. In general, the daily dose range may be from about 10 μg to about 30 mg per kg body weight of a human and non-human animal, preferably from about 50 μg to about 30 mg per kg of body weight of a human and non-human animal, for example from about 50 μg to about 10 mg per kg of body weight of a human and non-human animal, for example from about 100 μg to about 30 mg per kg of body weight of a human and non-human animal, for example from about 100 µg to about 10 mg per kg of body weight of a human and non-human animal and most preferably from about 100 µg to about 1 mg per kg of body weight of a human and non-human animal.

Pharmaceutical Formulations

While it is possible for the active compound to be administered alone, it is preferable to present it as a pharmaceutical composition (e.g. formulation).

Accordingly, in another embodiment of the invention, there is provided a pharmaceutical composition comprising at least one compound of the formula (1) as defined above together with at least one pharmaceutically acceptable excipient.

The composition may be a tablet composition.

The composition may be a capsule composition.

The pharmaceutically acceptable excipient(s) can be selected from, for example, carriers (e.g. a solid, liquid or semi-solid carrier), adjuvants, diluents (e.g. solid diluents such as fillers or bulking agents; and liquid diluents such as solvents and cosolvents), granulating agents, binders, flow aids, coating agents, release-controlling agents (e.g. release retarding or delaying polymers or waxes), binding agents, disintegrants, buffering agents, lubricants, preservatives, anti-fungal and antibacterial agents, antioxidants, buffering agents, tonicity-adjusting agents, thickening agents, flavouring agents, sweeteners, pigments, plasticizers, taste masking agents, stabilisers or any other excipients conventionally used in pharmaceutical compositions.

The term "pharmaceutically acceptable" as used herein means compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formula (1) can be formulated in accordance with known techniques, see for example, Remington's Pharmaceutical Sciences, Mack Publishing Company, Easton, PA, USA.

The pharmaceutical compositions can be in any form suitable for oral, parenteral, topical, intranasal, intrabronchial, sublingual, ophthalmic, otic, rectal, intra-vaginal, or transdermal administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

The pharmaceutical compositions typically comprise from approximately 1% (w/w) to approximately 95%, preferably % (w/w) active ingredient and from 99% (w/w) to 5% (w/w) of a pharmaceutically acceptable excipient (for example as defined above) or combination of such excipients. Preferably, the compositions comprise from approximately 20% (w/w) to approximately 90% (w/w) active ingredient and from 80% (w/w) to 10% of a pharmaceutically excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragées, powders, tablets or capsules.

Tablets and capsules may contain, for example, 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition typically contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The pharmaceutical formulations may be presented to a patient in "patient packs" containing an entire course of treatment in a single package, usually a blister pack.

The compounds of the formula (1) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect (effective amount). The precise amounts of compound administered may be determined by a supervising physician in accordance with standard procedures.

EXAMPLES

The invention will now be illustrated, but not limited, by reference to the specific embodiments described in the following examples.

Examples 1 to 26

The compounds of Examples 1 to 26 shown in Table 1 below have been prepared. Their NMR and LCMS properties and the methods used to prepare them are set out in Table 3. Starting materials and intermediates used in the synthesis of each of the Examples are listed in Table 2.

TABLE 1

Example compounds

Example 1

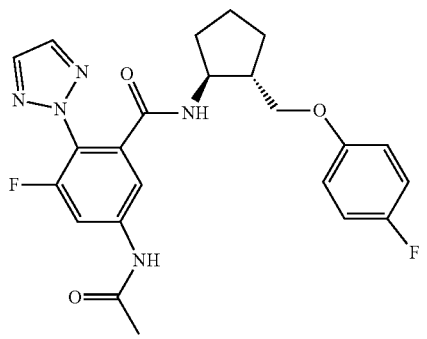 [SMILES: CC(=O)Nc1cc(F)c(-n2nccn2)c(C(=O)N[C@H]2CCC[C@@H]2COc2ccc(F)cc2)c1]

Example 2

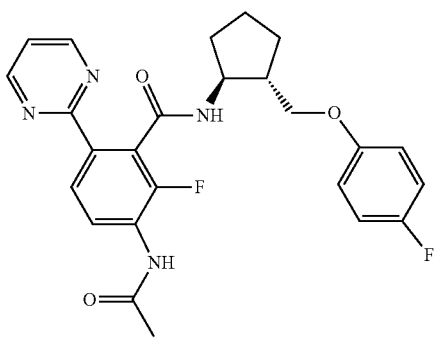 [SMILES: CC(=O)Nc1ccc(-c2ncccn2)c(C(=O)N[C@H]2CCC[C@@H]2COc2ccc(F)cc2)c1F]

Example 3

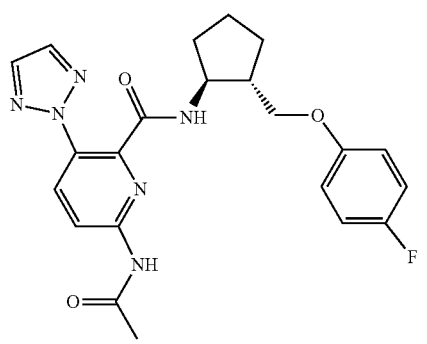 [SMILES: CC(=O)Nc1ccc(-n2nccn2)c(C(=O)N[C@H]2CCC[C@@H]2COc2ccc(F)cc2)n1]

Example 4

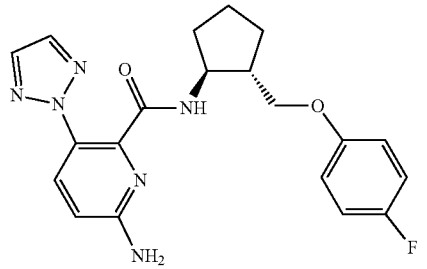 [SMILES: Nc1ccc(-n2nccn2)c(C(=O)N[C@H]2CCC[C@@H]2COc2ccc(F)cc2)n1]

TABLE 1-continued

Example compounds

Example 5

Example 6

Example 7

Example 8

TABLE 1-continued
Example compounds
Example 9
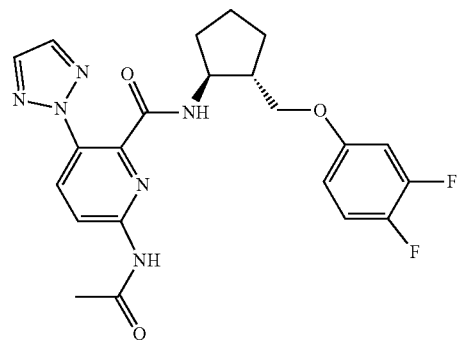 [SMILES: CC(=O)Nc1ccc(-n2nccn2)c(C(=O)N[C@H]2CCC[C@@H]2COc2ccc(F)c(F)c2)n1]
Example 10
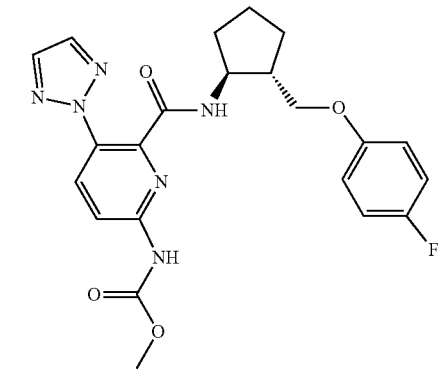 [SMILES: COC(=O)Nc1ccc(-n2nccn2)c(C(=O)N[C@H]2CCC[C@@H]2COc2ccc(F)cc2)n1]
Example 11
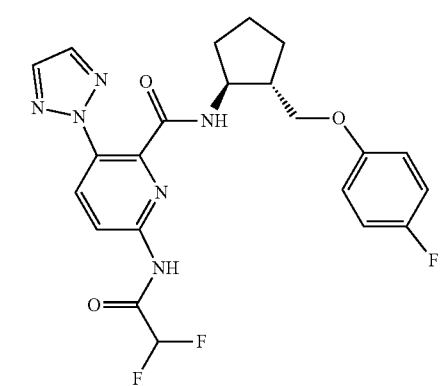 [SMILES: O=C(N[C@H]1CCC[C@@H]1COc1ccc(F)cc1)c1nc(NC(=O)C(F)F)ccc1-n1nccn1]
Example 12
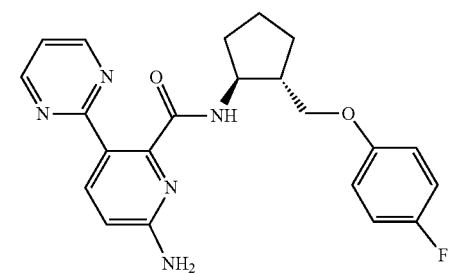 [SMILES: Nc1ccc(-c2ncccn2)c(C(=O)N[C@H]2CCC[C@@H]2COc2ccc(F)cc2)n1]
TABLE 1-continued
Example compounds
Example 13
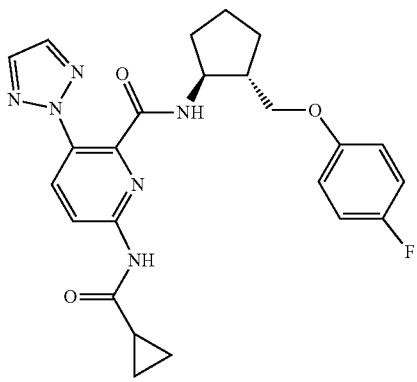 [SMILES: O=C(N[C@H]1CCC[C@@H]1COc1ccc(F)cc1)c1nc(NC(=O)C2CC2)ccc1-n1nccn1]
Example 14
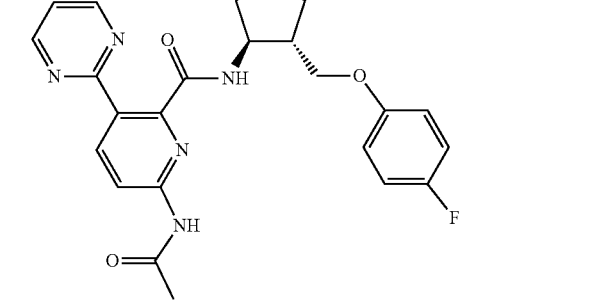
Example 15
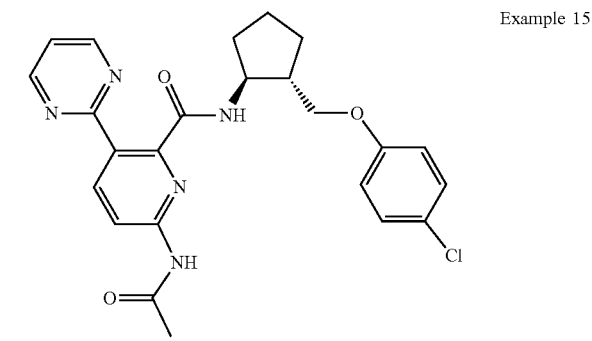
Example 16
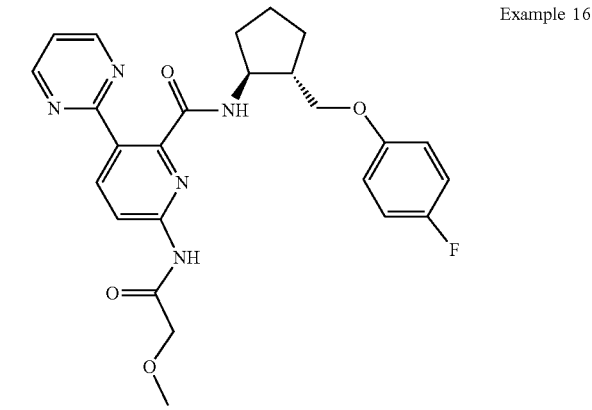

TABLE 1-continued
Example compounds
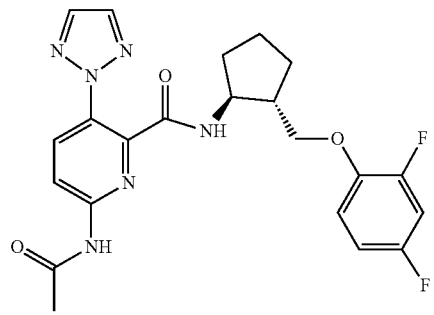 [SMILES: CC(=O)Nc1ccc(-n2nccn2)c(C(=O)N[C@H]2CCC[C@@H]2COc2ccc(F)cc2F)n1]
Example 17
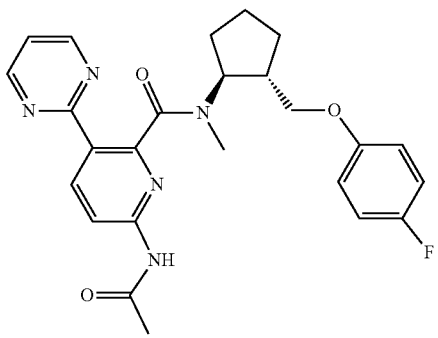 [SMILES: CC(=O)Nc1ccc(-c2ncccn2)c(C(=O)N(C)[C@H]2CCC[C@@H]2COc2ccc(F)cc2)n1]
Example 18
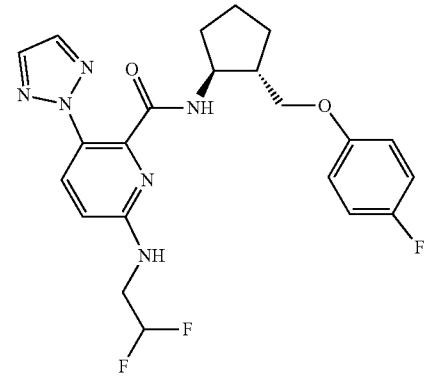 [SMILES: O=C(N[C@H]1CCC[C@@H]1COc1ccc(F)cc1)c1nc(NCC(F)F)ccc1-n1nccn1]
Example 19
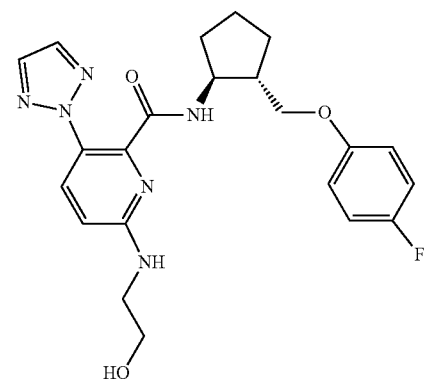 [SMILES: O=C(N[C@H]1CCC[C@@H]1COc1ccc(F)cc1)c1nc(NCCO)ccc1-n1nccn1]
Example 20
TABLE 1-continued
Example compounds
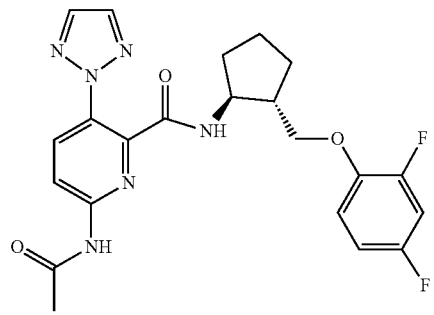 [SMILES: CC(=O)Nc1ccc(-n2nccn2)c(C(=O)N[C@H]2CCC[C@@H]2COc2ccc(F)cc2F)n1]
Example 21
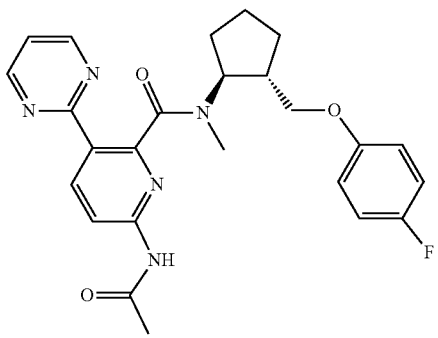 [SMILES: CC(=O)Nc1ccc(-c2ncccn2)c(C(=O)N(C)[C@H]2CCC[C@@H]2COc2ccc(F)cc2)n1]
Example 22
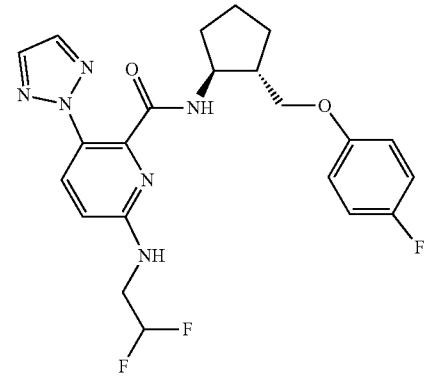 [SMILES: O=C(N[C@H]1CCC[C@@H]1COc1ccc(F)cc1)c1nc(NCC(F)F)ccc1-n1nccn1]
Example 23
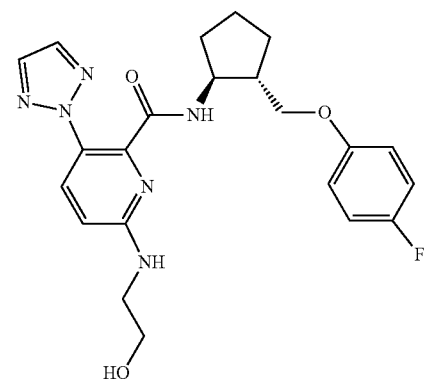 [SMILES: O=C(N[C@H]1CCC[C@@H]1COc1ccc(F)cc1)c1nc(NCCO)ccc1-n1nccn1]
Example 24

TABLE 1-continued

Example compounds

Example 25

Example 26

Preparation of the Compounds of the Invention

Compounds of the invention may be prepared by routes including those in FIG. 1. Details of many of the standard transformations such as those in the routes below and others which could be used to perform the same transformations can be found in standard reference textbooks such as "Organic Synthesis", M. B. Smith, McGraw-Hill (1994) or "Advanced Organic Chemistry", 4$^{th}$ edition, J. March, John Wiley & Sons (1992).

Compounds of the invention may be prepared by an amide coupling reaction between a substituted 2-(phenoxymethyl)cyclopentan-1-amine or 2-((pyridin-2-yloxy)methyl)cyclopentan-1-amine and a substituted benzoic, nicotinic, isonicotinic or picolinic acid. The reaction conditions will typically use a coupling agent or agents, for example EDCI and HOBt, or HATU, with a suitable base such as DIPEA or Et$_3$N, in a solvent such as DCM or DMF, typically at between room temperature and 50° C. A further example of amide coupling conditions is the use of T3P (typically as a solution in EtOAc) and a suitable base such as DIPEA, in a solvent such as DMF at rt. Alternatively, amide couplings may be performed by reacting the amine with an acid chloride in the presence of a base, for example sodium hydride or Et$_3$N, in a suitable solvent such as THF or DCM, typically at between 0° C. and room temperature. Acid chlorides can be prepared from the corresponding acid via a number of methods, for example reaction with oxalyl chloride in a solvent system such as THF and DMF, typically at rt, or reaction with phosphorous oxychloride in the presence of a base such as pyridine, typically in a solvent such as DCM at 0° C.

Certain compounds of the invention may be prepared by first reacting a substituted cyclopentan-1-amine with a substituted benzoic, nicotinic, isonicotinic or picolinic acid to form the corresponding amide, then further reacting the amide product. An example of a subsequent reaction is a palladium-catalysed carbon-carbon coupling reaction between an aryl halide, for example an aryl bromide, and a trialkylstannane, commonly known as a Stille coupling (Cordovilla et al, ACS Catal., 2015, 5, 3040-3053). The trialkylstannane may be for example a tributyl- or trimethylstannane, and the palladium catalyst may be for example Pd(PPh$_3$)$_4$ or Pd(P$^t$Bu$_3$)$_2$, and the reaction may or may not be carried out in the presence of an additive or additives such as CsF, CuCl or CuI. Typically, the Stille coupling reaction will be performed in a solvent such as DMF or 1,4-dioxane, at elevated temperature, for example between 100° C. and 130° C. A further example of subsequent reaction is the reduction of an ester, for example a methyl ester, to the corresponding primary alcohol, which is then itself further reacted to form an ether. The reduction may be performed using a reducing agent such as LiBH$_4$ in a suitable solvent, for example THF, at a suitable temperature range, for example 0° C. to rt. The ether formation may be performed under nucleophilic aromatic substitution (S$_N$Ar) conditions, wherein the alcohol is deprotonated by a suitable strong base such as NaH, then reacted with a 2-halopyridine, for example a 2-fluoropyridine, in a solvent such as DMF, at a suitable temperature range, for example rt to 50° C. Another example of a subsequent reaction is a further amide coupling between an amine and an acid or acid chloride under conditions such as those described above, or reaction with an anhydride such as acetic anhydride, in the presence or absence of DMAP, in a solvent such as DCM or THF at rt. A further example of a subsequent reaction is the alkylation of an amine group, for example by reaction with an alkyl tosylate in the presence of a base such as K$_2$CO$_3$, an additive such as KI, in DMF at 120° C., or reaction with an alkyl halide, for example a bromide, in the presence of a base such as NaH in a solvent such as DMF at rt. Furthermore, an unprotected amine may be reacted with a chloroformate, such as methyl chloroformate, in the presence of a base such as pyridine, in a solvent such as DCM at rt, to yield a carbamate group. In such cases the amine used in the subsequent reaction may have been protected during the initial amide formation step, for example with a protecting group such as a tert-butylcarbamate (commonly known as Boc protection) which can be deprotected under acidic conditions, for example TFA in DCM at rt. An alternative group such as an acetate may be used as an amine protecting group, and may be removed under basic conditions, for example by treatment with NaOMe in MeOH at rt, or by treatment with 2N aqueous NaOH in 1,4-dioxane at 100° C. The deprotection of amines in this fashion may also form compounds of the invention. Other functional groups may be deprotected to form compounds of the invention, for example a hydroxy group protected with a methyl ether can be removed, for example, using BBr$_3$ in a solvent such as DCM at rt.

Substituted 2-(phenoxymethyl)cyclopentan-1-amines or 2-((pyridin-2-yloxy)methyl)cyclopentan-1-amines may be prepared by a number of methods, using transformations that will be familiar to those with skill in the art of organic synthesis. One method of preparation of amines that are subsequently used for preparation of compounds of the invention is reduction of a carboxylic acid group present on the cyclopentane ring to the corresponding primary alcohol, followed by conversion to an ether using triphenylphosphine, an aryl alcohol, and an azodicarboxylate such as DIAD in a solvent such as THF at a suitable temperature, for example rt. Such a reaction is commonly known as a Mitsonobu coupling (Swamy et al, Chem. Rev., 2009, 109, 2551-2561). The reduction of a carboxylic acid may be performed using borane-THF complex, or the deutero borane-THF version, in a solvent such as THF at a suitable temperature range, for example between 0° C. and 30° C. In an alternative method for the formation of ethers the primary alcohol may be converted to a methane sulfonate ester using methane sulfonyl chloride and a base such as Et$_3$N, in a suitable solvent, for example DCM, at room temperature. The methane sulfonate ester can be substituted by an aryl alcohol in the presence of a suitable base, for example cesium carbonate, typically in a solvent such as DMF at an elevated temperature, for example 80° C. Typically, the amine functionality is protected during these transformations, for example as the tert-butylcarbamate (commonly known as Boc protection) which can be deprotected under acidic conditions, for example HCl in 1,4-dioxane or MeOH at a temperature between 0° C. and rt. The amine functionality, whether protected or not, may be derivatised under appropriate conditions to provide intermediates which are subsequently transformed into compounds of the invention. For example, a Boc-protected amine may be alkylated by reaction with an alkyl halide, for example methyl iodide, in the presence of a base such as sodium hydride, in a suitable solvent such as THF at rt. In an alternative approach an unprotected amine may be alkylated under reductive alkylation conditions, for example using a ketone such as acetone in the presence of an acid such as acetic acid, and a reducing agent such as sodium cyanoborohydride in a solvent such as DCM at rt.

Substituted benzoic, nicotinic, isonicotinic or picolinic acids can be prepared in a number of different ways using standard transformations which will be known to those skilled in the art. For example, the acid functionality can be prepared by hydrolysis of the corresponding ester or nitrile group under acidic or basic conditions, and in some instances hydrolysis may occur concomitantly with another functional group transformation under the reaction conditions. A 2H-1,2,3-triazol-2-yl group may be introduced by reaction of an aryl halide or heteroaryl halide functionality, for example a bromide, with 2H-1,2,3-triazole, in the presence or absence of a copper reagent such as CuI, and the presence of an amine such as a dimethylcyclohexane-1,2-diamine, in the presence of a base such as cesium carbonate in a suitable solvent such as DMF, typically at an elevated temperature such as 110° C. to 120° C. An aryl or heteroaryl group, for example pyrimidin-2-yl, may be introduced using Stille coupling conditions as detailed above, or introduced using an aryl or heteroaryl halide, for example 2-bromopyrimidine, an aryl or heteroaryl boronic acid or ester, a suitable palladium catalyst such as Pd(PPh$_3$)$_4$, a base such as K$_2$CO$_3$, in a suitable solvent system such as 1,4-dioxane, at an elevated temperature, for example 80° C. (commonly known as a Suzuki-Miyaura coupling, Miyaura et al, *Chem. Rev.*, 1995, 95, 2457-2483).

Where intermediates are commercially available they are identified by their chemical abstracts service (CAS) reference number in Table 2, where not commercially available the synthesis of the intermediates using standard transformations is detailed herein. Commercial reagents were utilized without further purification.

General Procedures

Room temperature (rt) refers to approximately 20-27° C. $^1$H NMR spectra were typically recorded at 400 or 500 MHz at ambient temperature unless otherwise specified. Chemical shift values are expressed in parts per million (ppm), i.e. (δ)-values. Standard abbreviations, or their combinations, are used for the multiplicity of the NMR signals, for example: s=singlet, br=broad, d=doublet, t=triplet, q=quartet, quin=quintet or p=pentet, h=heptet, dd=doublet of doublets, dt=doublet of triplets, m=multiplet. Coupling constants are listed as J values, measured in Hz. NMR and mass spectroscopy results were corrected to account for background peaks. Chromatography refers to column chromatography performed using silica or C18 silica and executed under positive pressure (flash chromatography) conditions.

LCMS Methods

LCMS experiments were carried out using electrospray conditions under the conditions below (Solvents: A1=0.1% HCO$_2$H in H$_2$O; A2=0.1% HCO$_2$H and 10 mM ammonium bicarbonate in H$_2$O; A3=2.5 L H$_2$O+2.5 mL 28% ammonia in H$_2$O solution; A4=0.1% HCO$_2$H in H$_2$O:MeCN (95:5); A5=0.05% ammonium acetate and 0.1% HCO$_2$H in H$_2$O; B1=0.1% HCO$_2$H in H$_2$O:MeCN (1:9); B2=MeCN; B3=2.5 L MeCN+135 mL H$_2$O+2.5 mL 28% ammonia in H$_2$O solution; B4=0.1% HCO$_2$H in MeCN; B5=2.5 L MeCN+125 mL H$_2$O+2.5 mL HCO$_2$H); B6=MeOH. LCMS data are given in the format: Mass ion, electrospray mode (positive or negative), retention time (experimental text and Table 1); Mass ion, electrospray mode (positive or negative), retention time, approximate purity (Table 2).

Method 1. Instruments: Hewlett Packard 1100 with G1315A DAD and Micromass ZQ mass detector; Column: Waters X-Bridge C18, 2.5 micron, 2.1×20 mm or Phenomenex Gemini-NX C18, 3 micron, 2.0×30 mm; Gradient [time (min)/solvent B3 in A3(%)]: 0.00/2, 0.10/2, 8.40/95, 10.00/95; Injection volume 1 μL; Instruments: Hewlett Packard 1100 with G1315A DAD, 45° C.; Flow rate 1.5 mL/min.

Method 2. Instruments: Waters Acquity UPLC with photodiode array detector and QDa mass detector; Column: C18, 1.6 micron, 2.1×50 mm; Gradient [time (min)/solvent B1 in A1(%)]:0.00/10, 0.75/10, 2.80/90, 4.50/100, 4.60/100, 4.70/10, 6.00/10; column temperature 35° C.; Flow rate 0.8 mL/min.

Method 3. Instruments: Waters 2690 HPLC with 996 Photodiode Array Detector and Acquity QDA mass detector; Column: Waters X-Bridge C18, 5 micron, 4.6×100 mm; Gradient [time (min)/solvent B2 in A2(%)]: 0.00/10, 1.00/10, 5.00/100, 7.00/100, 7.50/10, 8.00/10; Flow rate 1.2 mL/min.

Method 4. Instruments: Waters Acquity UPLC with PDA detector and QDA; Column: C18, 1.6 micron, 2.1×50 mm; Gradient [time (min)/solvent B1 in A1(%)]: 0.00/3, 0.20/3, 2.70/98, 3.00/100, 3.50/100, 3.51/3, 4.00/3; Column temperature 35° C.; Flow rate 0.8-1.0 mL/min.

Method 5. Instruments: Agilent Technologies 1260 LC with Chemstation software, Diode Array Detector, Agilent 6120 Quadrupole MS with APCI and ES Source; Column: Phenomenex Gemini-NX C18, 3 micron, 2×30 mm; Gradient [time (min)/solvent B3 in A3(%)]:0.00/5, 2.00/95, 2.50/95, 2.60/5, 3.00/5; Injection volume 0.5 μL; UV detection 190-400 nm; column temperature 40° C.; Flow rate 1.5 mL/min.

Method 6. Instruments: Waters Acquity UPLC; Column: Waters X-Select C18, 2.5 micron, 4.6×30 mm or 1.7 micron, 2.1×30 mm; Gradient [time (min)/solvent B4 in A1(%)]: 0.00/5, 0.11/5, 2.15/95, 2.56/95, 2.83/5; Injection volume 3 μL; UV detection 210-400 nm; column temperature 40° C.; Flow rate 0.77 mL/min.

Method 7. Instruments: Agilent Technologies 1290 Infinity II Series LC with 6125 Quadrupole MSD; Column: Zorbax XDB C18, 5 micron; Gradient [time (min)/solvent B2 in A4(%)]:0.00/5, 2.50/95, 4.00/95, 4.50/5, 6.00/5; Injection volume 1 μL; UV detection 210-400 nm; column temperature 25° C.; Flow rate 1.5 mL/min.

Method 8. Instruments: Agilent Technologies 1260 LC with Chemstation software, Diode Array Detector, Agilent 6120 Quadrupole MS with APCI and ES Source; Column: Phenomenex Kinetex C18, 5 micron, 2.1×50 mm; Gradient [time (min)/solvent B5 in A1(%)]:0.00/5, 2.00/95, 2.50/95, 2.60/5, 3.00/5; Injection volume 0.5 μL; UV detection 190-400 nm; column temperature 40° C.; Flow rate 1.5 mL/min.

Method 9. Instruments: Waters Alliance 2690 with 996 photodiode array detector and Micromass ZQ mass detector; Column: C18, 5 micron, 4.6×150 mm; Gradient [time (min)/solvent B6 in A5(%)]:0.00/10, 7.00/90, 9.00/100, 14.00/100, 14.10/10, 17.00/10; Flow rate 1.0 mL/min.

Abbreviations

DBU=1,8-diazabicyclo(5.4.0)undec-7-ene
DCM=dichloromethane
DIAD=diisopropyl azodicarboxylate
DIPEA=N,N-diisopropylethylamine
DMAP=4-(dimethylamino)pyridine
DMF=N,N-dimethylformamide
DMSO=dimethylsulfoxide
EDCI=N-(3-dimethylaminopropyl)-N'-ethylcarbodiimide hydrochloride
ES=electrospray
EtOAc=ethyl acetate
h=hour(s)
HOBt=1-hydroxybenzotriazole hydrate
L=litre
LC=liquid chromatography
LCMS=liquid chromatography mass spectrometry
MeCN=acetonitrile
min=minute(s)
MS=mass spectrometry
NMR=nuclear magnetic resonance
rcf=relative centrifugal force
rpm=revolutions per minute
rt=room temperature
s=second(s)
T3P=1-propanephosphonic anhydride
TBME=tert-butyl methyl ether
THF=tetrahydrofuran
Prefixes n-, s-, t- and tert- have their usual meanings: normal, secondary, iso, and tertiary.

Synthesis of Intermediates

Preparation of Substituted (1S,2S)-2-(phenoxymethyl)cyclopentan-1-amine Intermediates Typical Procedure 1, Exemplified by the Preparation of Intermediate 2, (1S,2S)-2-((4-fluorophenoxy)methyl)cyclopentan-1-amine Hydrochloride

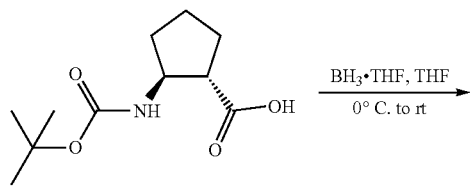

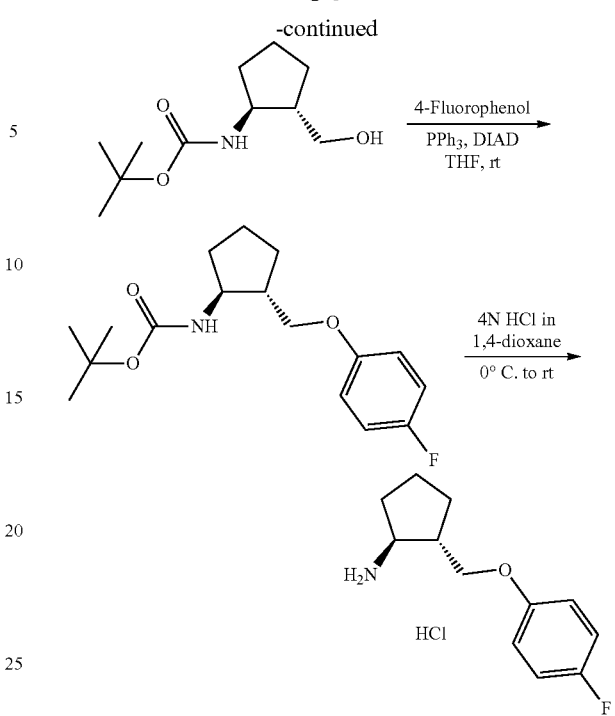

Step 1. A solution of (1S,2S)-2-(tert-butoxycarbonylamino)cyclopentane carboxylic acid (Intermediate 1, 50 g, 0.218 mol) in dry THF (500 mL) was stirred under $N_2$ and cooled to −15° C. to −20° C. All solids dissolved leaving a colourless solution, to which borane-THF complex (1M, 545 mL, 0.545 mol) was added dropwise over 1.5 h at such a rate as to maintain the temperature of the now milky solution at <0° C. Once addition was complete the reaction mixture was allowed to stir at 0° C. for 2 h; the cooling bath was removed and reaction mixture allowed to warm to rt overnight. The reaction mixture was then cooled to −15° C. to −20° C. and cautiously quenched with MeOH (0.9 L) over 30 min maintaining the vessel temperature at <0° C. The reaction mixture was then warmed to rt over 2 h and concentrated in vacuo. MeOH (400 mL) was added and the mixture concentrated in vacuo. Purification by gradient flash chromatography eluting with 20-25% EtOAc in hexane yielded tert-butyl ((1S,2S)-2-(hydroxymethyl)cyclopentyl)carbamate (23.0 g, 106.8 mmol) as a colourless, brittle solid.

LCMS (Method 2): m/z 160.1 (ES+, M−55), at 1.88 min.
$^1$H NMR: (400 MHz, DMSO-$d_6$) δ 6.79 (d, J=7.8 Hz, 1H), 4.40 (t, J=5.2 Hz, 1H), 3.51-3.35 (m, 2H), 3.21 (ddd, J=10.5, 6.8, 5.4 Hz, 1H), 1.84-1.64 (m, 4H), 1.61-1.41 (m, 2H), 1.37 (s, 9H), 1.33-1.20 (m, 1H).

A further batch of the above material (303.0 g, 1.41 mol) was prepared from (1S,2S)-2-(tert-butoxycarbonylamino) cyclopentane carboxylic acid (Intermediate 1, 400 g, 1.74 mol) and borane-THF complex (1M, 4.34 L, 4.34 mol) in THF (4.0 L) using the methods above. Purification by gradient flash chromatography eluting with 10-30% EtOAc in hexane yielded material with LCMS purity of approximately 100% that was used directly in the next step.

Step 2. Tert-butyl ((1S,2S)-2-(hydroxymethyl)cyclopentyl)carbamate (214 g, 994 mmol), triphenyl phosphine (261 g, 994 mmol) and 4-fluorophenol (112 g, 994 mmol) in dry THF (4 L) was stirred at rt under $N_2$ for 10 min until all solids had dissolved. The solution was then cooled to −10° C. to 0° C. and DIAD (196 mL, 994 mmol) was added dropwise over 30 min at such a rate as to maintain the vessel temperature between −5° C. to 0° C. Once addition was complete the reaction mixture was allowed to stir at 0-5° C. for 1 h before warming to rt and stirring for 4 h. Solvent was removed in vacuo and the resulting pale yellow crude slurry was stored in the fridge overnight. The slurry was combined with material from an analogous reaction performed on 100 g scale of tert-butyl ((1S,2S)-2-(hydroxymethyl)cyclopentyl)carbamate and purification by gradient flash chromatography eluting with 5-10% EtOAc in hexane yielded tert-butyl ((1S,2S)-2-((4-fluorophenoxy)methyl)cyclopentyl) carbamate (228 g, 737 mmol).

LCMS (Method 2): m/z 210.2 (ES+, M−99), at 2.77 min.
$^{1}$H NMR: (400 MHz, DMSO-$d_6$) δ 7.18-7.04 (m, 2H), 6.98-6.83 (m, 3H), 3.93 (dd, J=9.4, 4.8 Hz, 1H), 3.80 (dd, J=9.4, 7.5 Hz, 1H), 3.60 (p, J=7.6 Hz, 1H), 2.16-2.02 (m, 1H), 1.93-1.76 (m, 2H), 1.69-1.48 (m, 2H), 1.48-1.39 (m, 2H), 1.37 (s, 9H).

A second batch of material (177 g) with approximately 6% contamination with 4-fluorophenol was isolated from the gradient column chromatography and used separately to the 228 g batch in the subsequent step.

Step 3. Tert-butyl ((1S,2S)-2-((4-fluorophenoxy)methyl) cyclopentyl)carbamate (6.0 g, 19.4 mmol) was dissolved in 1,4-dioxane (80 mL) and cooled to 0-5° C. under $N_2$. 4M HCl in 1,4-dioxane (60 mL, 240 mmol) was added dropwise over 15 min, stirring was continued at 0-5° C. for 30 min and then at rt for 3 h. The resulting colourless slurry was concentrated in vacuo before pentane (100 mL) was added, the mixture was stirred overnight, then filtered and washed with cold pentane (10 mL). Air-drying until constant weight yielded the title compound (Batch 1, 3.2 g, 15.3 mmol). Further batches of material were prepared using the above method; batches 2 and 3 were prepared from tert-butyl ((1S,2S)-2-((4-fluorophenoxy)methyl)cyclopentyl)carbamate (60.0 g, 194 mmol and 168 g, 543 mmol respectively), 4M HCl in 1,4-dioxane (600 mL, 2.4 mol and 1.68 L, 6.7 mol respectively) in 1,4-dioxane (800 mL and 2 L respectively); batch 4 was prepared from tert-butyl ((1S,2S)-2-((4-fluorophenoxy)methyl)cyclopentyl)carbamate (177 g of 94% purity), 4M HCl in 1,4-dioxane (1.66 L, 6.64 mol) and 1,4-dioxane (2 L). In each case the batch 2, 3 and 4 reaction mixtures were seeded with isolated batch 1 material after 4M HCl in 1,4-dioxane had been added and the reaction mixtures were stirred at 0-5° C. for 30-60 min. Following seeding with batch 1 material, the reaction mixtures were then stirred at rt overnight before isolation as above. $^{1}$H NMR analysis of isolated batches confirmed that they were identical and a single final quantity of the title compound (285 g, 1.36 mol) was isolated by blending individual batches.

Data in Table 2.

Intermediate 3, (1S,2S)-2-((4-chlorophenoxy) methyl)cyclopentan-1-amine Hydrochloride

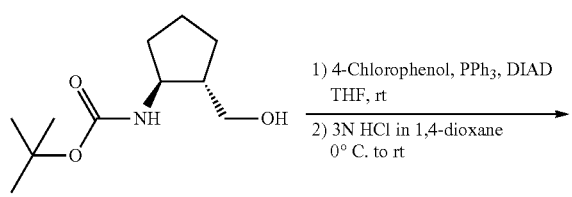

1) 4-Chlorophenol, PPh$_3$, DIAD
THF, rt
2) 3N HCl in 1,4-dioxane
0° C. to rt

-continued

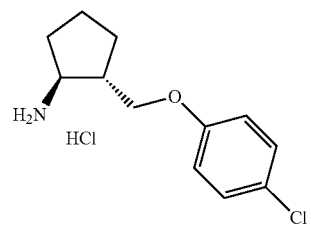

Step 1. Tert-butyl ((1S,2S)-2-(hydroxymethyl)cyclopentyl)carbamate (Intermediate 2, Step 1; 6.00 g, 27.9 mmol), 4-chlorophenol (3.94 g, 30.7 mmol) and triphenylphosphine (7.32 g, 27.9 mmol) were dissolved in THF (8.7 mL) at rt and sonicated for 10 min before the dropwise addition of DIAD (6.04 mL, 30.7 mmol). The reaction mixture was sonicated at rt for 15 min before concentration in vacuo. Purification by gradient flash chromatography eluting with 0-25% EtOAc in hexane yielded tert-butyl ((1S,2S)-2-((4-chlorophenoxy)methyl)cyclopentyl)carbamate (9.00 g) as a yellow solid which was used in the subsequent step without further purification.

LCMS (Method 3): m/z 226.2 (ES+, M−99), at 2.97 min, approximate purity 79%.

Step 2. A solution of tert-butyl ((1S,2S)-2-((4-chlorophenoxy)methyl)cyclopentyl)carbamate (9.00 g) in DCM (120 mL) was cooled to 0° C. and 3N HCl in dioxane (3N, 50 mL) was added drop wise. The reaction mixture was stirred at rt for 18 h before concentration in vacuo. Trituration with diethyl ether yielded the title compound (5.50 g, 24.4 mmol) as an off white solid.

Data in Table 2.

Intermediate 4, (1S,2S)-2-((4-fluorophenoxy) methyl-$d_2$)cyclopentan-1-amine

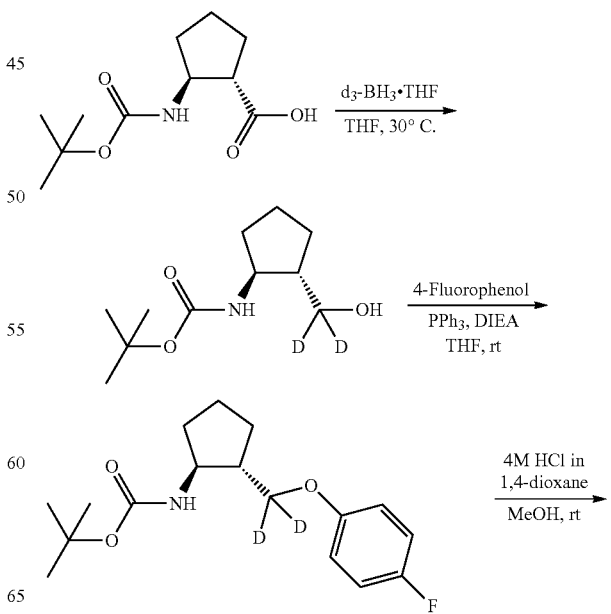

$d_3$-BH$_3$•THF
THF, 30° C.

4-Fluorophenol
PPh$_3$, DIEA
THF, rt

4M HCl in
1,4-dioxane
MeOH, rt

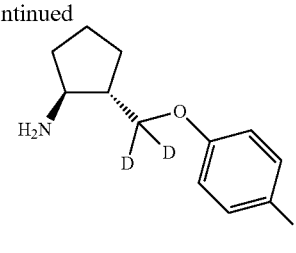

The title compound (342 mg, 1.62 mmol) was prepared in three steps from (1S,2S)-2-(tert-butoxycarbonylamino)cyclopentane carboxylic acid (Intermediate 1, 1.00 g, 4.36 mmol) and d₃-borane-THF complex (1M, 9.60 mL, 9.60 mmol) in THF (30 mL) at 30° C. for 3 h; DIAD (0.47 mL, 2.41 mmol), triphenylphosphine 632 mg, 2.41 mmol) and 4-fluorophenol (225 mg, 2.01 mmol) in THF (10 mL) at rt for 4 h; and HCl in 1,4-dioxane (4M, 4.65 mL, 18.6 mmol) in MeOH (10 mL) at rt overnight, using the methods of Intermediate 2, steps 1 to 3. After completion of step 3, the title compound was isolated as a white solid by concentration in vacuo, azeotroping with toluene, and purification by loading onto an SCX cartridge, which was washed with MeOH and eluted with NH₃ (approximately 1M in MeOH).

Data in Table 2.

Intermediate 5, (1S,2S)-2-((3,4-difluorophenoxy)methyl)cyclopentan-1-amine

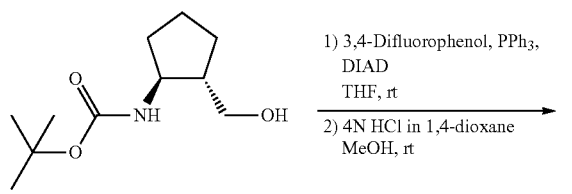

The title compound (376 mg, 1.65 mmol) was prepared in two steps from tert-butyl ((1S,2S)-2-(hydroxymethyl)cyclopentyl)carbamate (Intermediate 2, Step 1; 495 mg, 2.30 mmol), DIAD (0.49 mL, 2.51 mmol), triphenylphosphine (658 mg, 2.51 mmol) and 3,4-difluorophenol (272 mg, 2.09 mmol) in THF (10 mL) at rt for 3 h; and HCl in 1,4-dioxane (4M, 4.93 mL, 19.7 mmol) in MeOH (6 mL) at rt overnight, using the methods of Intermediate 2, steps 2 and 3. After completion of step 2, the title compound was isolated as an off-white solid by concentration in vacuo, azeotroping with toluene, and purification by loading onto an SCX cartridge, which was washed with MeOH and eluted with NH₃ (approximately 1M in MeOH).

Data in Table 2.

Typical Procedure 2, Exemplified by the Preparation of Intermediate 6, (1S,2S)-2-((2,4-difluorophenoxy)methyl)cyclopentan-1-amine

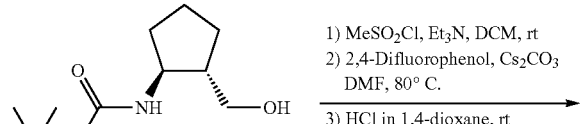

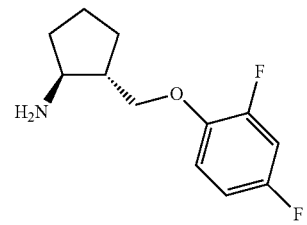

Step 1. Mesyl chloride (4.54 mL, 39.6 mmol) was added dropwise to a solution of tert-butyl ((1S,2S)-2-(hydroxymethyl)cyclopentyl)carbamate (Intermediate 2, Step 1; 7.11 g, 33.0 mmol) and triethylamine (9.21 mL, 66.1 mmol) in DCM (80 mL) at 0° C. The solution was stirred at rt for 3 h before partitioning between H₂O (300 mL) and DCM (200 mL). The aqueous phase was extracted with DCM (2×150 mL) and the combined organic phases were dried (Na₂SO₄) and concentrated in vacuo. Purification by gradient flash chromatography eluting with 0-10% EtOAc in hexane yielded ((1S,2S)-2-((tert-butoxycarbonyl)amino)cyclopentyl)methyl methanesulfonate (9.00 g, 30.7 mmol) as an off white solid.

LCMS (Method 4): m/z 194.1 (ES+, M−99), at 1.74 min.
¹H NMR: (400 MHz, DMSO-d₆) δ 6.95 (d, J=8.1 Hz, 1H), 4.19 (dd, J=9.7, 5.1 Hz, 1H), 4.07 (dd, J=9.7, 7.3 Hz, 1H), 3.53 (p, J=7.9 Hz, 1H), 3.15 (s, 3H), 2.02 (dt, J=15.2, 7.8 Hz, 1H), 1.91-1.72 (m, 2H), 1.68-1.47 (m, 2H), 1.46-1.27 (m, 2H), 1.37 (s, 9H).

Step 2. A mixture of ((1S,2S)-2-((tert-butoxycarbonyl)amino)cyclopentyl)methyl methanesulfonate (7.00 g, 23.8 mmol), 2,4-difluorophenol (6.20 g, 47.7 mmol) and Cs₂CO₃ (15.5 g, 47.7 mmol) in DMF (100 mL) was stirred at 80° C. for 6 h. After partitioning between H₂O (1 L) and EtOAc (200 mL) the aqueous layer was extracted with EtOAc (2×150 mL) and the combined organic phases were dried (Na₂SO₄) and concentrated in vacuo. Purification by gradient flash chromatography eluting with 0-8% EtOAc in hexane yielded tert-butyl ((1S,2S)-2-((2,4-difluorophenoxy)methyl)cyclopentyl)carbamate (6.00 g, 18.3 mmol) as a light yellow solid.

LCMS (Method 4): m/z 228.2 (ES+, M−99), at 2.37 min.
¹H NMR: (400 MHz, DMSO-d₆) δ 7.26 (ddd, J=11.7, 8.8, 3.1 Hz, 1H), 7.16 (td, J=9.4, 5.5 Hz, 1H), 7.05-6.88 (m, 2H), 4.02 (dd, J=9.5, 4.7 Hz, 1H), 3.88 (dd, J=9.5, 7.4 Hz, 1H), 3.60 (p, J=7.7 Hz, 1H), 2.11 (q, J=7.1 Hz, 1H), 1.96-1.79 (m, 2H), 1.70-1.48 (m, 2H), 1.48-1.38 (m, 2H), 1.36 (s, 9H).

Step 3. The title compound (300 mg, 1.32 mmol) was prepared as a clear, colourless gum from tert-butyl ((1S,2S)-2-((2,4-difluorophenoxy)methyl)cyclopentyl)carbamate (604 mg, 1.85 mmol), 4N HCl in dioxane (4.61 mL) and MeOH (15 mL) at rt for 4 h, using the methods of Intermediate 3, step 2. Upon completion of the reaction and concentration in vacuo the resulting material was azeotroped with toluene and loaded on to an SCX cartridge. The cartridge was flushed with MeOH, then a 1M solution of NH₃ in MeOH was used to elute the title compound.

Data in Table 2.

Typical Procedure 3, Exemplified by the Preparation of Intermediate 7, (1S,2S)-2-((4-fluorophenoxy)methyl)-N-methylcyclopentan-1-amine Hydrochloride

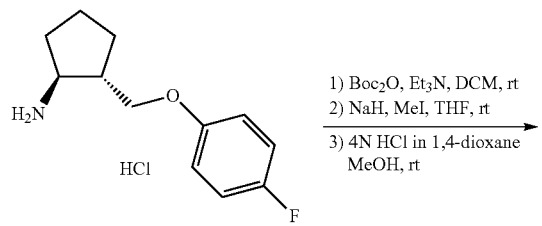

Step 1. Et₃N (0.17 mL, 1.22 mmol) was added to a suspension of (1S,2S)-2-((4-fluorophenoxy)methyl)cyclopentan-1-amine hydrochloride (Intermediate 2, 120.0 mg, 0.49 mmol) and di-tert-butyl dicarbonate (117 mg, 0.54 mmol) in DCM (3 mL) under N₂. The reaction was stirred at rt for 3 h before the addition of DCM (5 mL). The phases were separated and the organic phase was washed with saturated aqueous sodium bicarbonate (5 mL) and concentrated in vacuo. Purification by gradient flash column chromatography eluting with 0-10% EtOAc in iso-hexane yielded tert-butyl ((1S,2S)-2-((4-fluorophenoxy)methyl)cyclopentyl)carbamate (144 mg, 0.47 mmol) as a white solid.

¹H NMR: (400 MHz, DMSO-d₆) δ 7.09 (t, J=8.8 Hz, 2H), 6.95-6.86 (m, 3H), 3.93 (dd, J=9.4, 4.8 Hz, 1H), 3.80 (dd, J=9.4, 7.5 Hz, 1H), 3.60 (p, J=7.7 Hz, 1H), 2.13-2.07 (m, 1H), 1.92-1.77 (m, 2H), 1.68-1.48 (m, 2H), 1.47-1.38 (m, 2H), 1.37 (s, 9H).

Step 2. NaH (60% dispersion in mineral oil, 20.5 mg, 0.51 mmol) was added to a solution of tert-butyl ((1S,2S)-2-((4-fluorophenoxy)methyl)cyclopentyl)carbamate (144 mg, 0.47 mmol) in THF (2 mL) under N₂. After stirring for 5 min iodomethane (0.04 mL, 0.70 mmol) was added and the reaction stirred for 1 d at rt, before further iodomethane (0.04 mL, 0.70 mmol) was added and the reaction stirred overnight. The reaction mixture was partitioned between EtOAc (10 mL) and H₂O (10 mL) and the aqueous phase was extracted with EtOAc (2×15 mL). The combined organic phases were washed with H₂O (40 mL) and saturated brine (2×40 mL) and concentrated in vacuo. Purification by flash column chromatography eluting with 0-20% EtOAc in iso-hexane yielded tert-butyl ((1S,2S)-2-((4-fluorophenoxy)methyl)cyclopentyl)(methyl)carbamate (144 mg, 0.45 mmol) as a colourless gum.

LCMS (Method 5): m/z 346.2 (ES+, M+Na), at 1.89 min.

¹H NMR: (400 MHz, DMSO-d₆) δ 7.10 (t, J=8.6 Hz, 2H), 6.89 (dd, J=9.1, 4.4 Hz, 2H), 4.23 (s, 1H), 3.85 (d, J=5.6 Hz, 2H), 2.68 (s, 3H), 2.31-2.20 (m, 1H), 1.84 (br. s, 1H), 1.78-1.58 (m, 4H), 1.51-1.39 (m, 1H), 1.31 (s, 9H).

Step 3. A solution of tert-butyl ((1S,2S)-2-((4-fluorophenoxy)methyl)cyclopentyl)(methyl)carbamate (144 mg, 0.45 mmol) and hydrogen chloride (4M in 1,4-dioxane, 1.11 mL, 4.45 mmol) in MeOH (3 mL) was stirred at rt overnight. The solution was concentrated in vacuo and azeotroped with toluene to yield the title compound (100 mg, 0.39 mmol) as a white solid.

Data in Table 2.

Typical Procedure 4, Exemplified by the Preparation of Intermediate 8, (1S,2S)-2-((4-fluorophenoxy)methyl)-N-isopropylcyclopentane-1-amine

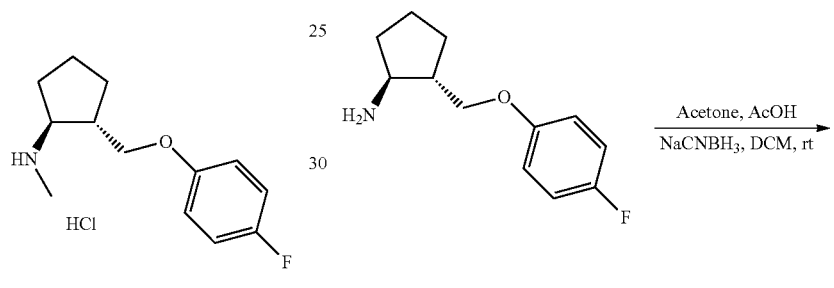

(1S,2S)-2-((4-Fluorophenoxy)methyl)cyclopentan-1-amine (Intermediate 2, free base, 0.45 g, 2.15 mmol) was dissolved in DCM (5 mL) and acetone (5 mL). Glacial AcOH (0.01 g, 0.22 mmol) was added and the reaction mixture was stirred at rt for 4 h. Sodium cyanoborohydride (0.40 g, 0.65 mmol) was added and the reaction mixture was stirred at rt for 4 h before concentration in vacuo. The residue was partitioned between H₂O (150 mL) and EtOAc (50 mL) and the aqueous phase was extracted with EtOAc (2×50 mL). The combined organic phases were dried (Na₂SO₄) and concentrated in vacuo to yield the title compound (0.45 g, 1.79 mmol) as a yellow sticky semi-solid that was used without further purification in the synthesis of Example 7.

Data in Table 2.

Preparation of Substituted Benzoic, Nicotinic, Isonicotinic, and Picolinic Acid Intermediates Intermediate 10, 6-acetamido-3-(2H-1,2,3-triazol-2-yl)picolinic Acid

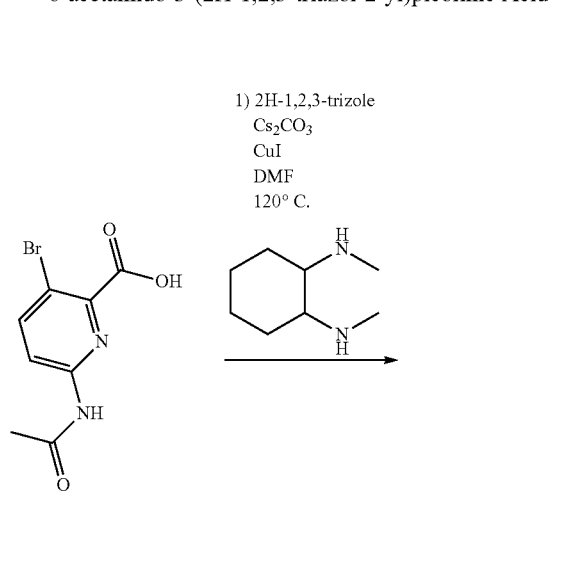

2H-1,2,3-Triazole (1.99 g, 29.0 mmol), Cs$_2$CO$_3$ (13.2 g, 40.5 mmol) and N$^1$,N$^2$-dimethylcyclohexane-1,2-diamine (0.27 g, 1.93 mmol) were added to a solution of 6-acetamido-3-bromopicolinic acid (Intermediate 9, 5.00 g, 19.3 mmol) in DMF (60 mL) and the mixture stirred under N$_2$ for 20 min at rt. CuI (0.37 g, 1.93 mmol) was added and the reaction mixture was stirred at 120° C. for 16 h. After cooling to rt the mixture was diluted with 1N NaOH (80 mL) and EtOAc (100 mL) and the phases were separated. The aqueous phase was washed with EtOAc (2×75 mL), acidified with 12N HCl (70 mL) and extracted with EtOAc (5×100 mL). The combined organic phases were dried (Na$_2$SO$_4$), concentrated in vacuo and triturated with MeCN (30 mL) to yield the title compound (2.40 g, 9.75 mmol) as a light brown solid.
Data in Table 2.

Intermediate 11, 6-amino-3-(2H-1,2,3-triazol-2-yl)picolinic Acid

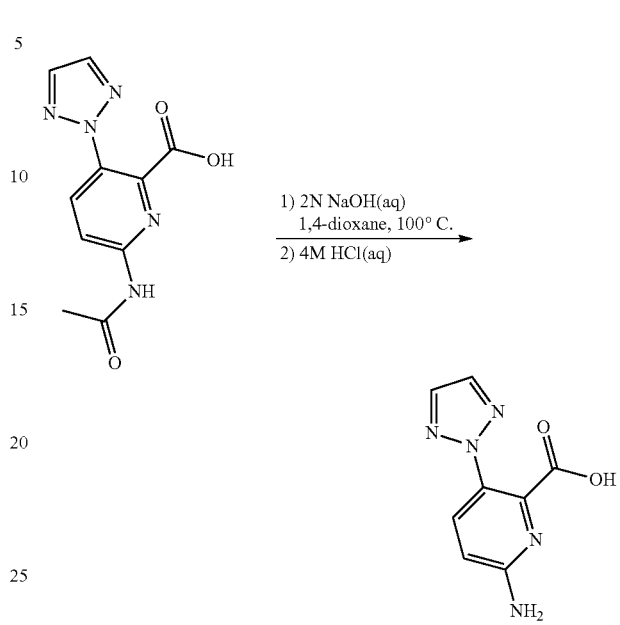

2N aqueous NaOH (5 mL) was added to a solution of 6-acetamido-3-(2H-1,2,3-triazol-2-yl)picolinic acid (Intermediate 10, 0.50 g, 2.02 mmol) in 1,4-dioxane (5 mL) and the reaction mixture was heated at 100° C. for 3 h. After cooling to rt the mixture was acidified to approximately pH 2 with 4N aqueous HCl. The resulting precipitate was isolated by filtration and dried in vacuo to yield the title compound (0.15 g, 0.73 mmol) as a light brown solid.
Data in Table 2.

Intermediate 12, 6-((methoxycarbonyl)amino)-3-(2H-1,2,3-triazol-2-yl)picolinic Acid

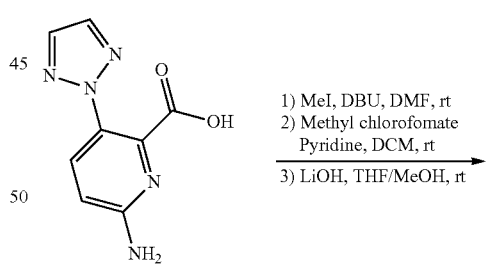

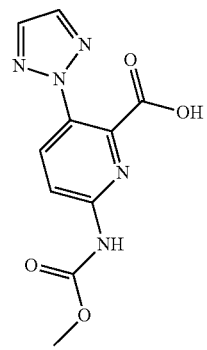

Step 1. DBU (21.8 mL, 146 mmol) was added to a solution of 6-amino-3-(2H-1,2,3-triazol-2-yl)picolinic acid (Intermediate 11, 10.0 g, 48.8 mmol) in DMF (70 mL) under $N_2$ at 0° C. After stirring at 0° C. for 30 min methyl iodide (11.6 mL, 195 mmol) was added and the reaction mixture was stirred at rt for 32 h. After filtration through celite the residue was washed with MeOH (250 mL) and the filtrate was concentrated in vacuo then partitioned between $H_2O$ (500 mL) and EtOAc (250 mL). The aqueous phase was extracted with EtOAc (2×150 mL) and the combined organic phases were dried ($Na_2SO_4$) and concentrated in vacuo to yield methyl 6-amino-3-(2H-1,2,3-triazol-2-yl)picolinate (3.20 g, 14.6 mmol) as a yellow sticky semi-solid.

LCMS (Method 4): m/z not observed (ES+), at 1.10 min.

$^1$H NMR: (400 MHz, DMSO-$d_6$) δ 8.01 (s, 2H), 7.84 (d, J=8.9 Hz, 1H), 6.75 (br. s, 2H), 6.70 (d, J=9.0 Hz, 1H), 3.64 (s, 3H).

Step 2. A solution of methyl 6-amino-3-(2H-1,2,3-triazol-2-yl)picolinate (3.20 g, 14.6 mmol) and pyridine (2.34 mL, 29.2 mmol) in DCM (30 mL) was stirred at rt for 20 min. Methyl chloroformate (1.69 mL, 21.9 mmol) was then added dropwise at 0° C. and the reaction was stirred at rt for 3 h. 15% aqueous citric acid solution (180 mL) and DCM (100 mL) were added and the phases were separated. The aqueous phase was extracted with DCM (2×150 mL), the combined organic phases were dried ($Na_2SO_4$), concentrated in vacuo, and purified by gradient flash column chromatography eluting with 0-80% EtOAc in hexane to yield methyl 6-((methoxycarbonyl)amino)-3-(2H-1,2,3-triazol-2-yl)picolinate (3.05 g, 11.0 mmol) as a white solid.

LCMS (Method 4): m/z 278.1 (ES+), at 1.44 min.

$^1$H NMR: (400 MHz, DMSO-$d_6$) δ 10.84 (s, 1H), 8.38 (d, J=9.1 Hz, 1H), 8.19 (d, J=9.1 Hz, 1H), 8.15 (s, 2H), 3.74 (s, 3H), 3.71 (s, 3H).

Step 3. LiOH monohydrate (4.62 g, 110 mmol) was added to a solution of methyl 6-((methoxycarbonyl)amino)-3-(2H-1,2,3-triazol-2-yl)picolinate (3.05 g, 11.0 mmol) in THF/MeOH (1:1, 60 mL) and the reaction was stirred at rt for 3 h. After concentration in vacuo the residue was acidified to approximately pH 2 with 1N aqueous HCl (80 mL) and extracted with EtOAc (120 mL). The aqueous phase was extracted with EtOAc (2×100 mL) and the combined organic phases were dried ($Na_2SO_4$) and concentrated in vacuo then triturated with n-pentane (50 mL) to yield the title compound (2.10 g, 7.98 mmol) as an off white solid.

Data in Table 2.

Intermediate 14, 5-acetamido-3-fluoro-2-(2H-1,2,3-triazol-2-yl)benzoic Acid

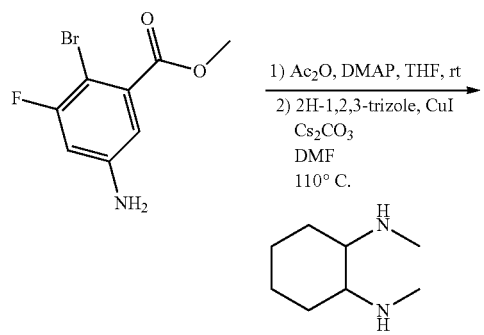

Step 1. Acetic anhydride (12.4 g, 121 mmol) and DMAP (2.47 g, 20.2 mmol) were added to a solution of methyl 5-amino-2-bromo-3-fluorobenzoate (Intermediate 13, 10.0 g, 40.5 mmol) in THF (100 mL) and the mixture was stirred at rt for 2 h. Saturated aqueous $NaHCO_3$ solution (100 mL) and EtOAc (70 mL) were added and the phases were separated. The aqueous phase was extracted with EtOAc (2×100 mL), the combined organic phases were dried ($Na_2SO_4$) and concentrated in vacuo. The residue was triturated with DCM:MeOH (8:1, 45 mL) to yield methyl 5-acetamido-2-bromo-3-fluorobenzoate (6.50 g, 22.4 mmol) as a light yellow solid.

LCMS (Method 2): m/z 292.0 (ES+), at 2.05 min.

$^1$H NMR: (400 MHz, DMSO-$d_6$) δ 10.45 (s, 1H), 7.86 (dd, J=11.0, 2.4 Hz, 1H), 7.78 (dd, J=2.5, 1.3 Hz, 1H), 3.88 (s, 3H), 2.07 (s, 3H).

Step 2. 2H-1,2,3-Triazole (1.97 g, 286 mmol), $Cs_2CO_3$ (12.4 g, 381 mmol) and $N^1,N^2$-dimethylcyclohexane-1,2-diamine (0.27 g, 1.90 mmol) were added to a solution of methyl 5-acetamido-2-bromo-3-fluorobenzoate (5.50 g, 190 mmol) in DMF (60 mL). After stirring at rt under $N_2$ for 20 min CuI (0.36 g, 1.90 mmol) was added at rt and the reaction mixture was heated at 110° C. for 16 h. After cooling to rt the reaction mixture was filtered through celite and washed with EtOAc (500 mL). The filtrate was acidified to approximately pH 5 with AcOH (100 mL) and concentrated in vacuo. Purification by reverse phase gradient flash column chromatography on C18 silica eluting with 2% MeCN in $H_2O$ yielded the title compound (0.50 g, 1.89 mmol) as a light brown solid.

Data in Table 2.

Intermediate 16, 3-acetamido-2-fluoro-6-(pyrimidin-2-yl)benzoic Acid

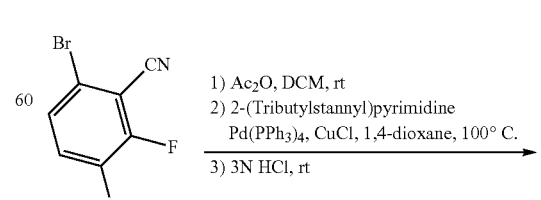

-continued

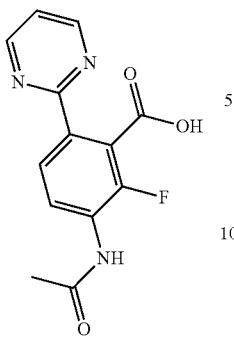

Step 1. 3-amino-6-bromo-2-fluorobenzonitrile (Intermediate 15, 6.5 g, 30.2 mmol) was dissolved in DCM (150 mL) and acetic anhydride (8.5 mL, 90 mmol) added. After stirring at rt for approximately 3 d aqueous NaHCO$_3$ solution (150 mL) was added and the phases were separated. The aqueous phase was extracted with DCM (4×50 mL) and the combined organic phases were washed with aqueous NaHCO$_3$ (100 mL) and brine (50 mL), dried (MgSO$_4$), then concentrated in vacuo to yield N-(4-bromo-3-cyano-2-fluorophenyl)acetamide (6.78 g, 23.0 mmol) as an orange solid.

$^1$H NMR: (500 MHz, DMSO-d$_6$) δ 10.14 (s, 1H), 8.21 (t, J=8.6 Hz, 1H), 7.67 (dd, J=8.9, 1.3 Hz, 1H), 2.12 (s, 3H).

Step 2. 2-(Tributylstannyl)pyrimidine (6.0 mL, 18.9 mmol) and CuCl (1.85 g, 18.7 mmol) were added to a solution of N-(4-bromo-3-cyano-2-fluorophenyl)acetamide (4.00 g, 15.6 mmol) in 1,4-dioxane (120 mL). The resulting suspension was degassed for 20 min before the addition of tetrakis(triphenylphosphine)palladium(0) (700 mg, 0.61 mmol) and the reaction mixture was then heated at 100° C. for 16 h before cooling to rt and the addition of H$_2$O (100 mL), 1M aqueous HCl (100 mL) and TBME (100 mL). The phases were separated, and the aqueous phase extracted with TBME (6×50 mL); brine (100 mL) was added to aid phase separation. The combined organic phases were dried (MgSO$_4$) and concentrated in vacuo. Purification by gradient flash column chromatography eluting with 0-100% EtOAc in iso-hexane yielded N-(3-cyano-2-fluoro-4-(pyrimidin-2-yl)phenyl)acetamide (940 mg) as a yellow solid with approximately 80% purity as assessed by $^1$H NMR. The aqueous phase was re-extracted with EtOAc (8×50 mL), the combined organic phases were dried (MgSO$_4$), concentrated in vacuo, and purified by gradient flash column chromatography eluting with 0-100% EtOAc in iso-hexane) to yield a further portion of N-(3-cyano-2-fluoro-4-(pyrimidin-2-yl)phenyl)acetamide (900 mg) as a yellow solid with approximately 96% purity as assessed by LCMS. The two portions were combined and used in the next step without further purification.

$^1$H NMR: (500 MHz, DMSO-d$_6$) δ 10.24 (s, 1H), 9.00 (d, J=4.9 Hz, 2H), 8.48 (t, J=8.4 Hz, 1H), 8.20 (dd, J=8.8, 1.2 Hz, 1H), 7.58 (t, J=4.9 Hz, 1H), 2.17 (d, J=4.8 Hz, 3H).

Step 3. N-(3-Cyano-2-fluoro-4-(pyrimidin-2-yl)phenyl)acetamide (1.58 g, 6.17 mmol) was dissolved in 3N HCl (50 mL) and stirred at rt for 3 h. H$_2$O (100 mL) and EtOAc (40 mL) were added and the phases were separated. The aqueous phase was extracted with EtOAc (5×40 mL) and the combined organic phases were dried (MgSO$_4$) and concentrated in vacuo. Purification by gradient flash column chromatography eluting with 0-10% (1% AcOH in MeOH) in DCM yielded the title compound (200 mg, 0.65 mmol) as an orange solid.

Data in Table 2.

Intermediate 18,
2-acetamido-5-(2H-1,2,3-triazol-2-yl)isonicotinic Acid

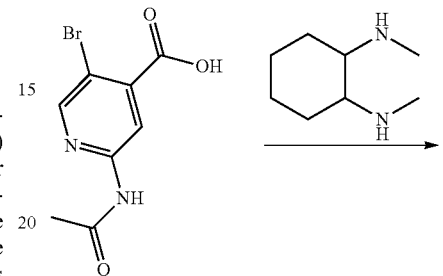

The title compound was prepared from 2-acetamido-5-bromoisonicotinic acid (Intermediate 17, 5.00 g, 19.4 mmol), 2H-1,2,3-triazole (2.00 g, 29.1 mmol), Cs$_2$CO$_3$ (14.8 g, 38.7 mmol), N$^1$,N$^2$-dimethylcyclohexane-1,2-diamine (0.55 g, 3.87 mmol) and CuI (0.74 g, 3.87 mmol) in DMF (50 mL) at 120° C. for 16 h using the methods of Intermediate 14, Step 2. Purification by gradient reverse phase flash column chromatography eluting with 0-35% MeCN in H$_2$O yielded the title compound (1.78 g, 7.20 mmol) as a white solid.

Data in Table 2.

Intermediate 20,
2-acetamido-5-(pyrimidin-2-yl)isonicotinic Acid

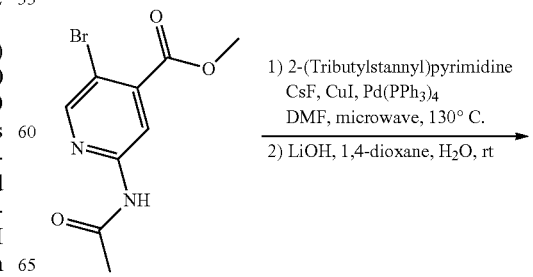

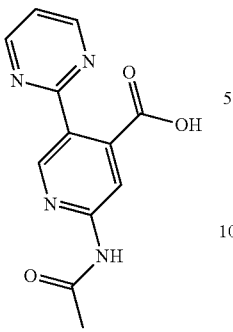

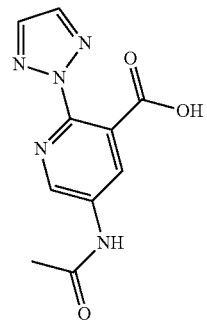

Step 1. A mixture of methyl 2-acetamido-5-bromoisonicotinate (Intermediate 19, 3.0 g, 11.0 mmol), 2-(tributylstannyl)pyrimidine (4.88 g, 13.2 mmol), CsF (3.32 g, 22.0 mmol) and CuI (209 mg, 1.10 mmol) was suspended in DMF (30.0 mL) and degassed with $N_2$ at rt for 20 min. Tetrakis(triphenylphosphine)palladium(0) (636 mg, 0.55 mmol) was added and the mixture was heated at 130° C. for 1 h in a microwave reactor. The reaction mixture was filtered through celite and the residue washed with EtOAc (100 mL). $H_2O$ (300 mL) and EtOAc (200 mL) were added to the filtrate and the phases were separated. The aqueous phase was extracted with EtOAc (2×100 mL) and the combined organic phases were dried ($Na_2SO_4$) and concentrated in vacuo. Purification by gradient flash column chromatography eluting with 0-50% EtOAc in hexane yielded methyl 2-acetamido-5-(pyrimidin-2-yl)isonicotinate (1.70 g, 6.25 mmol) as a yellow solid.

LCMS (Method 4): m/z 273.1 (ES+), at 1.24 min.

$^1$H NMR: (400 MHz, DMSO-$d_6$) δ 11.02 (s, 1H), 9.08 (d, J=0.7 Hz, 1H), 8.90 (d, J=4.9 Hz, 2H), 8.25 (s, 1H), 7.49 (t, J=4.9 Hz, 1H), 3.75 (s, 3H), 2.15 (s, 3H).

Step 2. LiOH monohydrate (0.24 g, 5.72 mmol) was added to a solution of methyl 2-acetamido-5-(pyrimidin-2-yl)isonicotinate (1.50 g, 6.00 mmol) in 1,4-dioxane (30 mL) and $H_2O$ (15 mL) and the reaction mixture was stirred at rt for 2 h. After concentration in vacuo purification by reverse phase gradient flash column chromatography on C18 silica eluting with 0-5% MeCN in $H_2O$ yielded the title compound (1.00 g, 3.87 mmol) as a white solid.

Data in Table 2.

Intermediate 22,
5-acetamido-2-(2H-1,2,3-triazol-2-yl)nicotinic Acid

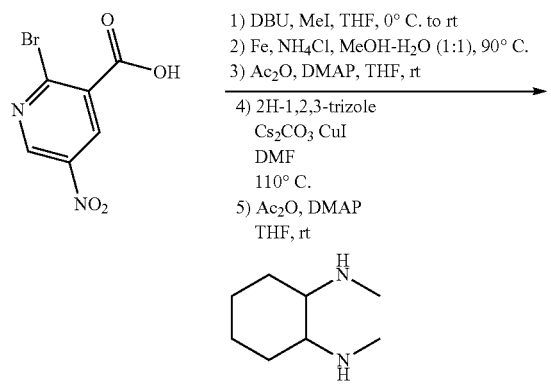

Step 1. DBU (3.36 mL, 24.3 mmol) was added dropwise to a solution of 2-bromo-5-nitronicotinic acid (Intermediate 21, 3.00 g, 12.2 mmol) in THF (50 mL) at 0° C. After stirring at 0° C. for 30 min methyl iodide (2.27 mL, 36.5 mmol) was added dropwise at 0° C. and the reaction mixture was then stirred at rt for 16 h. $H_2O$ (500 mL) and EtOAc (200 mL) were added, the phases were separated, and the aqueous phase was extracted with EtOAc (2×200 mL). The combined organic phases were dried ($Na_2SO_4$), concentrated in vacuo and purified by gradient flash column chromatography eluting with 0-20% EtOAc in hexane to yield methyl 2-bromo-5-nitronicotinate (2.30 g, 8.85 mmol) as a yellow sticky semi-solid.

LCMS (Method 4): m/z not observed (ES+), at 2.02 min.

$^1$H NMR: (400 MHz, DMSO-$d_6$) δ 9.33 (d, J=2.8 Hz, 1H), 8.86 (d, J=2.7 Hz, 1H), 3.94 (s, 3H).

Step 2. Fe powder (2.47 g, 44.2 mmol) and $NH_4Cl$ (4.26 g, 79.6 mmol) were added to a solution of methyl 2-bromo-5-nitronicotinate (2.30 g, 8.85 mmol) in MeOH:$H_2O$ (1:1, 50 mL) and the mixture was stirred at 90° C. for 3 h. After filtration through celite the residue was washed with MeOH (200 mL) and the combined filtrates were concentrated in vacuo and partitioned between $H_2O$ (250 mL) and EtOAc (100 mL). The aqueous phase was extracted with EtOAc (2×100 mL) and the combined organic phases were dried ($Na_2SO_4$) and concentrated in vacuo. Purification by reverse phase gradient flash column chromatography on C18 silica, eluting with 0-35% MeCN in $H_2O$ yielded methyl 5-amino-2-bromonicotinate (1.50 g, 6.52 mmol) as a yellow sticky semi-solid.

LCMS (Method 4): m/z 233.0 (ES+), at 1.11 min.

$^1$H NMR: (400 MHz, DMSO-$d_6$) δ 7.83 (d, J=3.0 Hz, 1H), 7.29 (d, J=3.0 Hz, 1H), 5.82 (br. s, 2H), 3.83 (d, J=3.1 Hz, 3H).

Step 3. Acetic anhydride (1.23 mL, 13.1 mmol) and DMAP (0.39 g, 3.26 mmol) were added to a solution of methyl 5-amino-2-bromonicotinate (1.50 g, 8.85 mmol) in THF (20 mL). After stirring at rt for 2 h saturated aqueous $NaHCO_3$ solution (250 mL) and EtOAc (100 mL) were added and the phases were separated. The aqueous phase was extracted with EtOAc (2×100 mL), the combined organic phases were dried ($Na_2SO_4$) and concentrated in vacuo. Purification by gradient flash column chromatography eluting with 0-65% EtOAc in hexane yielded methyl 5-acetamido-2-bromonicotinate (1.00 g, 3.68 mmol) as an off white solid.

LCMS (Method 4): m/z 274.7 (ES+), at 1.62 min.

$^1$H NMR: (400 MHz, DMSO-$d_6$+$D_2O$) δ 8.62 (d, J=2.8 Hz, 1H), 8.43 (d, J=2.7 Hz, 1H), 3.86 (s, 3H), 2.07 (s, 3H).

Step 4. 2H-1,2,3-Triazole (0.38 g, 5.53 mmol), $Cs_2CO_3$ (2.40 g, 7.38 mmol) and $N^1,N^2$-dimethylcyclohexane-1,2-diamine (52 mg, 0.37 mmol) were added to a solution of methyl 5-acetamido-2-bromonicotinate (1.00 g, 3.68 mmol) in DMF (20 mL). After degassing with N₂ for 20 min CuI (70 mg, 0.37 mmol) was added and the reaction was heated at 110° C. for 16 h, then cooled to rt and filtered through celite. The residue was washed with EtOAc (500 mL) and the filtrate was acidified to approximately pH 1 with aqueous HCl (1N, 50 mL) then concentrated in vacuo. Purification by reverse phase flash column chromatography on C18 silica eluting with 1% MeCN in H₂O yielded 5-amino-2-(2H-1,2,3-triazol-2-yl)nicotinic acid (0.10 g, 0.49 mmol) as a light brown solid.

LCMS (Method 8): m/z 206.1 (ES+), at 0.17 min.

¹H NMR: (400 MHz, DMSO-d₆) δ 7.95 (s, 2H), 7.94 (s, 1H), 7.36 (d, J=2.8 Hz, 1H), 6.04 (s, 2H).

Step 5. Acetic anhydride (0.18 mL, 1.95 mmol) and DMAP (59 mg, 0.49 mmol) were added to a solution of 5-amino-2-(2H-1,2,3-triazol-2-yl)nicotinic acid (0.2 g, 0.98 mmol) in THF (5 mL) at rt and the reaction mixture was stirred at rt for 16 h. After concentration in vacuo purification by reverse phase flash column chromatography on C18 silica eluting with 100% H₂O yielded the title compound (60 mg, 0.24 mmol) as a white solid.

Data in Table 2.

Intermediate 24, 6-((tert-butoxycarbonyl)amino)-3-(pyrimidin-2-yl)picolinic Acid

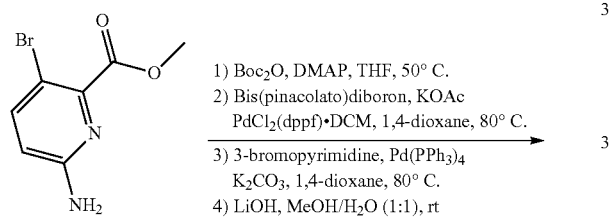

Step 1. A mixture of methyl 6-amino-3-bromopicolinate (Intermediate 23, 1.0 g, 4.33 mmol), di-tert-butyl dicarbonate (2.51 mL, 10.8 mmol) and DMAP (529 mg, 4.33 mmol) in THF (20 mL) was stirred at 50° C. for 2 h, then cooled to rt and concentrated in vacuo. Purification by gradient flash column chromatography eluting with 0-30% EtOAc in isohexane yielded methyl 6-[bis(tert-butoxycarbonyl)amino]-3-bromopyridine-2-carboxylate (1.43 g, 2.98 mmol) as a colourless oil.

LCMS (Method 6): m/z 275 (ES+, M−156), at 2.07 min.

¹H NMR: (500 MHz, DMSO-d₆) δ 8.31 (d, J=8.6 Hz, 1H), 7.59 (d, J=8.6 Hz, 1H), 3.90 (s, 3H), 1.40 (s, 18H).

Step 2. A mixture of methyl 6-[bis(tert-butoxycarbonyl)amino]-3-bromopyridine-2-carboxylate (1.40 g, 3.25 mmol), bis(pinacolato)diboron (1.15 g, 4.54 mmol), KOAc (0.96 g, 9.74 mmol) and [1,1′-bis(diphenylphosphino)ferrocene]dichloropalladium(II), complex with dichloromethane (133 mg, 0.16 mmol) in 1,4-dioxane (20 mL) was stirred at 80° C. for 16 h. After cooling to rt H₂O (50 mL) and EtOAc (50 mL) were added and the phases were separated. The organic phase was dried (MgSO₄) and concentrated in vacuo to yield crude {6-[bis(tert-butoxycarbonyl)amino]-2-(methoxycarbonyl)pyridin-3-yl}boronic acid (1.22 g, 2.16 mmol) as a dark brown oil that was used directly in the next step without further purification.

LCMS (Method 6): m/z 241 (ES+, M−155), at 1.19 min.

Step 3. A mixture of 2-bromopyrimidine (0.49 g, 3.08 mmol), {6-[bis(tert-butoxycarbonyl)amino]-2-(methoxycarbonyl)pyridin-3-yl}boronic acid (1.22 g, 3.08 mmol), K₂CO₃ (0.85 g, 6.16 mmol) and tetrakis(triphenylphosphine)palladium(0) (178 mg, 0.15 mmol) in 1,4-dioxane (20 mL) and H₂O (4 mL) was stirred at 80° C. for 3 h. After cooling to rt H₂O and EtOAc were added (100 mL each) and the phases were separated. The organic phase was dried (MgSO₄) and concentrated in vacuo. Purification by gradient flash column chromatography eluting with 0-100% EtOAc in isohexane) yielded methyl 6-[bis(tert-butoxycarbonyl)amino]-3-(pyrimidin-2-yl)pyridine-2-carboxylate (260 mg, 0.54 mmol) as a white solid.

LCMS (Method 6): m/z 453 (ES+, M+23), at 1.56 min.

¹H NMR: (500 MHz, DMSO-d₆) δ 8.95 (d, J=4.9 Hz, 2H), 8.67 (d, J=8.5 Hz, 1H), 7.74 (d, J=8.5 Hz, 1H), 7.55 (t, J=4.9 Hz, 1H), 3.77 (s, 3H), 1.43 (s, 18H).

Step 4. LiOH (29 mg, 1.21 mmol) was added to a solution of methyl 6-[bis(tert-butoxycarbonyl)amino]-3-(pyrimidin-2-yl)pyridine-2-carboxylate (260 mg, 0.60 mmol) in MeOH/H₂O (1:1, 10 mL). After stirring at rt for approximately 16 h aqueous 2M HCl (5 mL) and EtOAc (20 mL) were added and the phases were separated. The organic phase was dried (MgSO₄) and concentrated in vacuo to yield the title compound (90 mg, 0.27 mmol) as a white solid.

Data in Table 2.

Synthesis of Further Intermediates

Intermediate 26, 6-acetamido-3-bromo-N-((1S,2S)-2-((4-fluorophenoxy)methyl)cyclopentyl)picolinamide

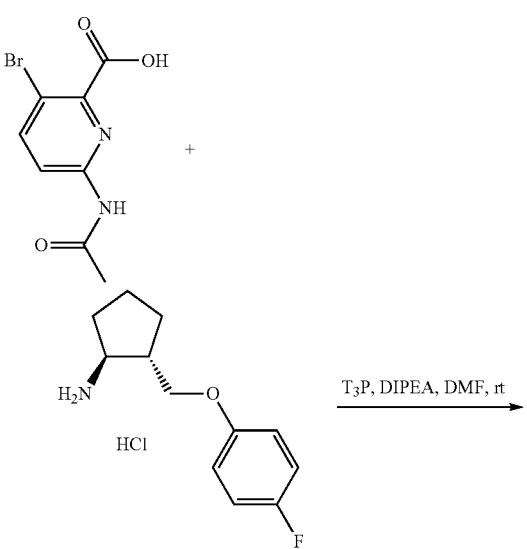

51

-continued

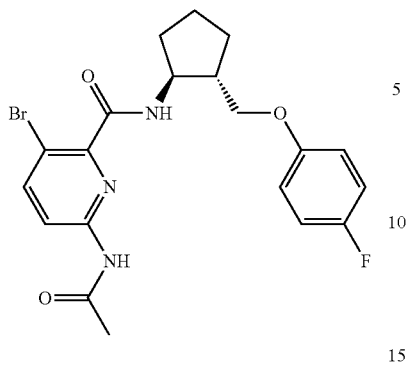

6-Acetamido-3-bromopicolinic acid (Intermediate 9, 248 mg, 0.96 mmol), DIPEA (431 mg, 3.35 mmol) and T$_3$P (912 mg, 1.434 mmol) were added to a solution of (1S,2S)-2-((4-fluorophenoxy)methyl)cyclopentan-1-amine (Intermediate 2 free base, 200 mg, 0.96 mmol) in THF (3 mL). After stirring at rt for 16 h the reaction mixture was partitioned between EtOAc (30 mL) and H$_2$O (25 mL). The organic phase was washed with brine (15 mL), dried (Na$_2$SO$_4$) and concentrated in vacuo. Purification by gradient flash column chromatography eluting with 0-30% EtOAc in petroleum ether yielded the title compound (150 mg, 0.07 mmol) as an off-white solid.

Data in Table 2.

SYNTHESIS OF EXAMPLES

Procedure 1:

Example 10, Methyl N-[6-[[(1S,2S)-2-[(4-fluorophenoxy)methyl]cyclopentyl]carbamoyl]-5-(triazol-2-yl)-2-pyridyl]carbamate

52

-continued

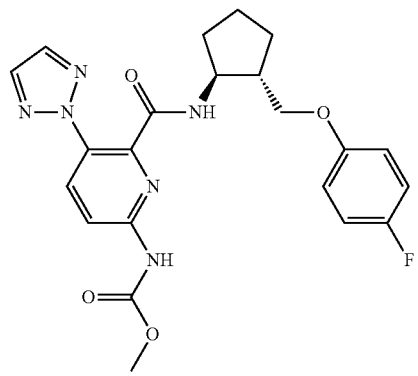

A solution of 6-((methoxycarbonyl)amino)-3-(2H-1,2,3-triazol-2-yl)picolinic acid (Intermediate 12, 1.81 g, 6.88 mmol) and (1S,2S)-2-((4-fluorophenoxy)methyl)cyclopentan-1-amine hydrochloride (Intermediate 2, 1.68 g, 6.88 mmol) in DMF (15 mL) was stirred at rt for 20 min before the addition of HATU (3.92 g, 10.30 mmol) and stirring at rt for 15 min. DIPEA (2.94 mL, 16.8 mmol) was added drop wise and the reaction mixture stirred at rt for 4 h before the addition of cold H$_2$O (120 mL) and EtOAc (80 mL). The phases were separated, and the aqueous phase was extracted with EtOAc (2×80 mL). The combined organic phases were dried (Na$_2$SO$_4$) and concentrated in vacuo. Purification by reverse phase gradient flash column chromatography on C18 silica, eluting with 0-60% MeCN in H$_2$O yielded the title compound (2.87 g, 6.32 mmol) as a white solid.

Data in Table 3.

Example 12, 6-amino-N-[(1S,2S)-2-[(4-fluorophenoxy)methyl]cyclopentyl]-3-pyrimidin-2-yl-pyridine-2-carboxamide

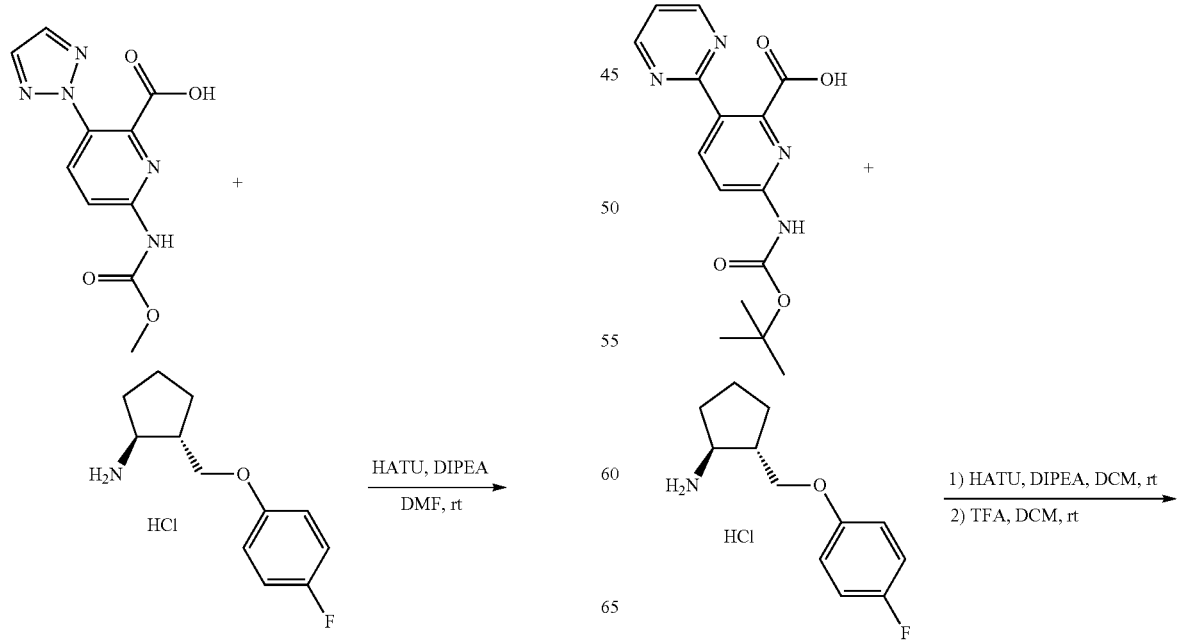

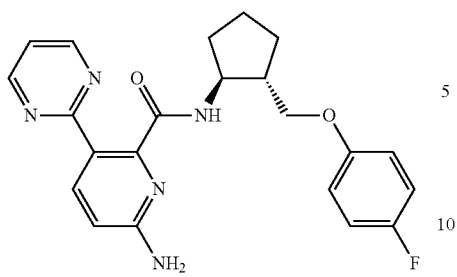

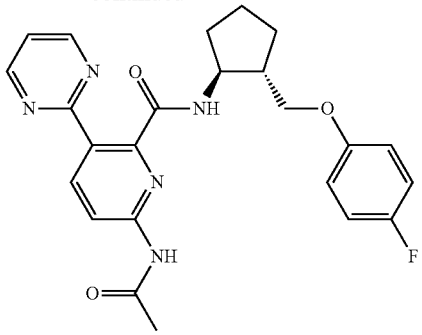

(1S,2S)-2-((4-Fluorophenoxy)methyl)cyclopentan-1-amine hydrochloride (Intermediate 2, 70 mg, 0.29 mmol), DIPEA (0.15 mL, 0.85 mmol) and HATU (130 mg, 0.34 mmol) were added to a solution of 6-((tert-butoxycarbonyl)amino)-3-(pyrimidin-2-yl)picolinic acid (Intermediate 24, 90 mg, 0.29 mmol) in DCM (10 mL). After stirring at rt overnight DCM (50 mL) and H$_2$O (50 mL) were added and the phases were separated. The organic phase was dried (MgSO$_4$) and concentrated in vacuo. DCM (5 mL) and TFA (5 mL) were added and the mixture was stirred at rt for 1 h before concentration in vacuo. Purification by gradient flash column chromatography eluting with 0-10% MeOH in DCM yielded the title compound (82 mg, 0.19 mmol) as a white solid.

Data in Table 3.

Example 14, 6-acetamido-N-[(1S,2S)-2-[(4-fluorophenoxy)methyl]cyclopentyl]-3-pyrimidin-2-yl-pyridine-2-carboxamide

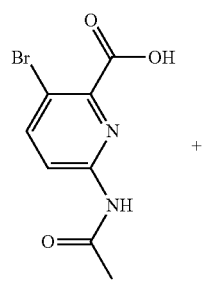

+

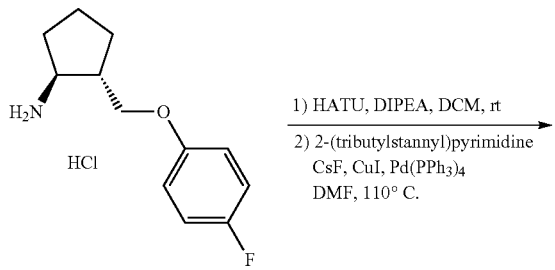

1) HATU, DIPEA, DCM, rt
2) 2-(tributylstannyl)pyrimidine
   CsF, CuI, Pd(PPh$_3$)$_4$
   DMF, 110° C.

Step 1. A solution of (1S,2S)-2-((4-Fluorophenoxy)methyl)cyclopentan-1-amine hydrochloride (Intermediate 2, 0.50 g, 2.49 mmol) and 6-acetamido-3-bromopicolinic acid (Intermediate 9, 0.63 g, 2.04 mmol) in DMF (10 mL) was stirred at rt for 10 min before the addition of HATU (1.16 g, 3.06 mmol). After stirring for 10 min at rt DIPEA (0.70 mL, 4.08 mmol) was added and the reaction mixture was stirred at rt for 16 h before dilution with H$_2$O (50 mL). The resulting precipitate was isolated by filtration and triturated with DCM:MeOH (9:1, 50 mL) to yield 6-acetamido-3-bromo-N-((1S,2S)-2-((4-fluorophenoxy)methyl)cyclopentyl)picolinamide (0.65 g, 1.44 mmol) as an off white solid.

LCMS (Method 2): m/z 474.0 (ES+, M+Na), at 2.45 min.
$^1$H NMR: (400 MHz, DMSO-d$_6$) δ 10.83 (s, 1H), 8.67 (d, J=7.8 Hz, 1H), 8.06 (s, 2H), 7.17-7.03 (m, 2H), 6.99-6.89 (m, 2H), 4.14-4.01 (m, 2H), 3.89 (dd, J=9.4, 7.6 Hz, 1H), 2.24 (pd, J=7.8, 4.4 Hz, 1H), 2.08 (s, 3H), 2.06-1.85 (m, 2H), 1.78-1.42 (m, 4H).

Step 2. A mixture of 2-(tributylstannyl)pyrimidine (0.49 g, 1.33 mmol), CsF (0.41 g, 2.67 mmol), CuI (25 mg, 0.13 mmol) and 6-acetamido-3-bromo-N-((1S,2S)-2-((4-fluorophenoxy)methyl)cyclopentyl)picolinamide (0.60 g, 1.33 mmol) in DMF (12 mL) was degassed with N$_2$ for 20 min. Tetrakis(triphenylphosphine)palladium(0) (0.15 g, 0.13 mmol) was added and the reaction mixture was heated at 110° C. for 6 h. After cooling to rt H$_2$O (300 mL) and EtOAc (100 mL) were added and the phases were separated. The aqueous phase was extracted with EtOAc (2×70 mL) and the combined organic phases were dried (Na$_2$SO$_4$) and concentrated in vacuo. Purification by gradient flash column chromatography eluting with 0-90% EtOAc in hexane yielded material that was purified further by preparative HPLC (Waters XBridge 5 μm C18 column, 250×30 mm, eluting with 20 to 98% MeCN/Solvent A over 22 min at 28 mL/min [where solvent A is 0.1% HCO$_2$H in H$_2$O]; followed by Waters Sunfire 5 μm silica column, 150×19.2 mm, eluting isocratically with heptane:iPrOH (78:22) at 22 mL/min), and trituration with diethyl ether to yield the title compound (8 mg, 0.02 mmol) as a white solid.

Data in Table 3.

Example 15, 6-acetamido-N-[(1S,2S)-2-[(4-chloro-phenoxy)methyl]cyclopentyl]-3-pyrimidin-2-yl-pyridine-2-carboxamide Example 18, 6-acetamido-N-[(1S,2S)-2-[(4-fluoro-phenoxy)methyl]cyclopentyl]-N-methyl-3-pyrimidin-2-yl-pyridine-2-carboxamide

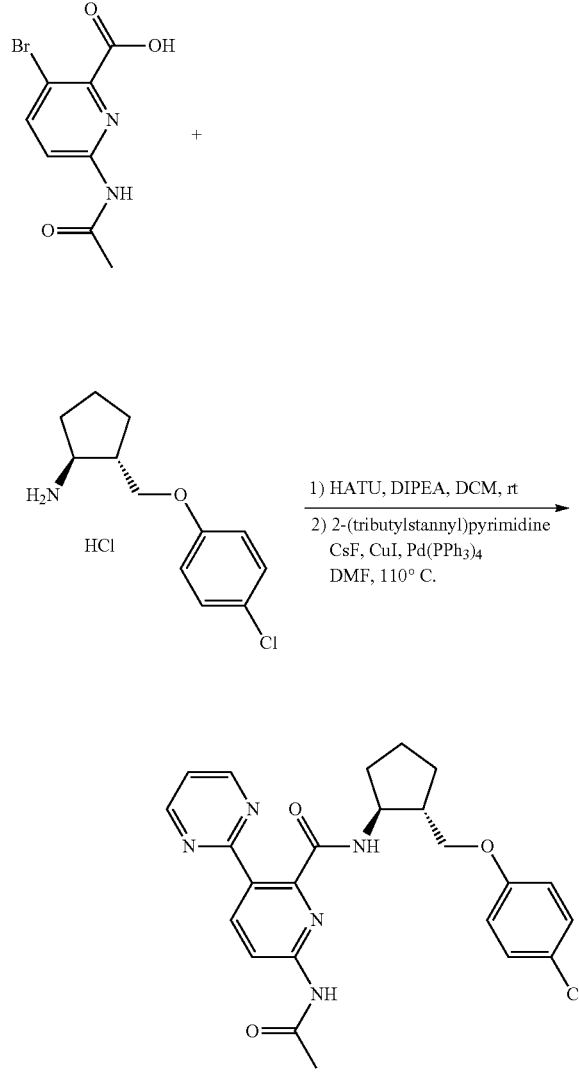

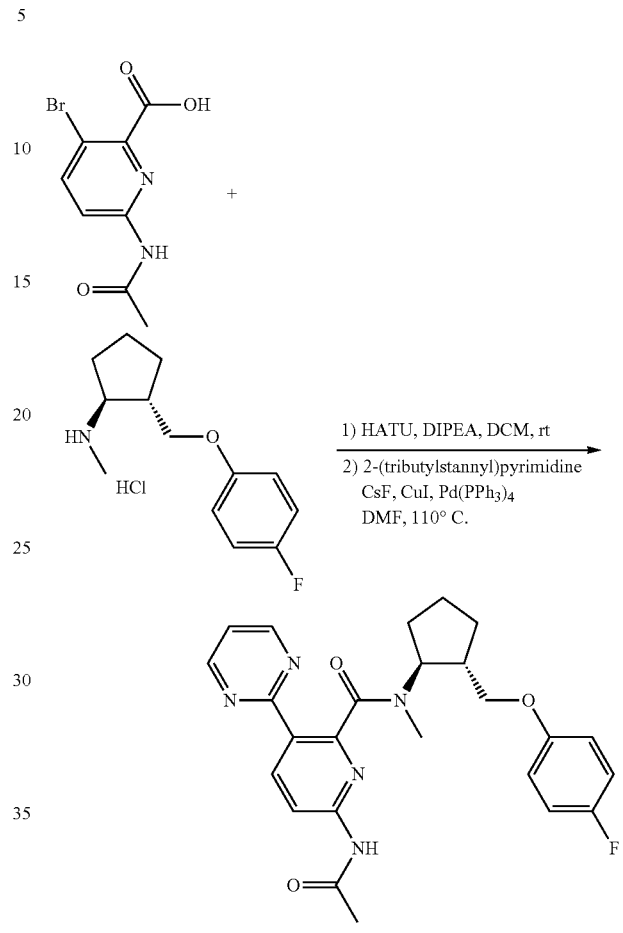

The title compound (11 mg, 0.02 mmol) was prepared in two steps from (1S,2S)-2-((4-chlorophenoxy)methyl)cyclo-pentan-1-amine hydrochloride (Intermediate 3, 0.25 g, 0.96 mmol), 6-acetamido-3-bromopicolinic acid (Intermediate 9, 0.29 g, 0.96 mmol), HATU (0.73 g, 1.92 mmol) and DIPEA (0.33 mL, 1.92 mmol) in DMF (5 mL) at rt for 16 h; and 2-(tributylstannyl)pyrimidine (0.59 g, 1.61 mmol), CsF (0.33 g, 2.15 mmol), CuI (20 mg, 0.11 mmol) and tetrakis (triphenylphosphine)palladium(0) (0.12 g, 0.11 mmol) in DMF (7 mL) at 110° C. for 6 h, using the methods of Example 14. After completion of step 2, purification by gradient flash column chromatography eluting with 0-100% EtOAc in hexane yielded material that was purified further by preparative HPLC (Waters Xbridge 5 μm C18 column, 250×30 mm, eluting with 25 to 98% MeCN/Solvent A over 26 min at 28 mL/min [where solvent A is 5 mM NH$_4$HCO$_3$+ 0.05% NH$_3$ in H$_2$O]) yielded the title compound.

Data in Table 3.

The title compound (70 mg, 0.15 mmol) was prepared in two steps from (1S,2S)-2-((4-fluorophenoxy)methyl)-N-methylcyclopentan-1-amine hydrochloride (Intermediate 7, 0.59 g, 2.27 mmol), 6-acetamido-3-bromopicolinic acid (Intermediate 9, 0.88 g, 3.30 mmol), HATU (1.29 g, 3.41 mmol) and DIPEA (1.70 mL, 6.82 mmol) in DMF (5 mL) at rt for 16 h; and 2-(tributylstannyl)pyrimidine (0.28 g, 0.77 mmol), CsF (0.19 g, 1.20 mmol), CuI (12 mg, 0.06 mmol) and tetrakis(triphenylphosphine)palladium(0) (0.15 g, 0.13 mmol) in DMF (3 mL) at 110° C. for 1 h in a microwave reactor, using the methods of Example 14. After completion of step 2, purification by reverse phase gradient flash column chromatography on C18 silica eluting with 0-75% MeCN in H$_2$O yielded material that was purified further by preparative HPLC (Agilent Zorbax 5 μm C18 column, 250×10 mm, eluting with 5 to 98% MeCN/Solvent A over 19 min at 12 mL/min [where solvent A is 5 mM NH$_4$HCO$_3$ in H$_2$O]) yielded the title compound.

Data in Table 3.

Procedure 2:

Example 8, 6-acetamido-N-[(1S,2S)-2-[dideuterio-(4-fluorophenoxy)methyl]cyclopentyl]-3-(triazol-2-yl)pyridine-2-carboxamide Procedure 3:

Example 7, 6-acetamido-N-[(1S,2S)-2-[(4-fluorophenoxy)methyl]cyclopentyl]-N-isopropyl-3-(triazol-2-yl)pyridine-2-carboxamide

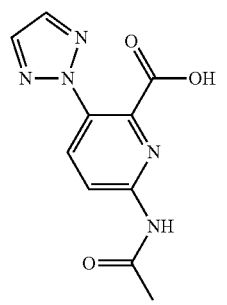

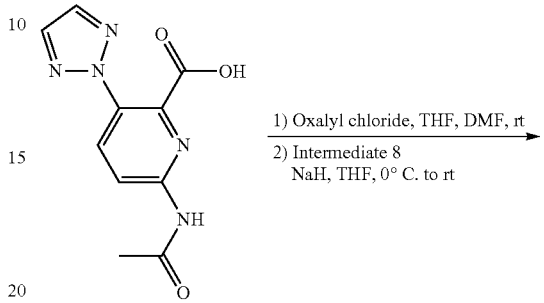

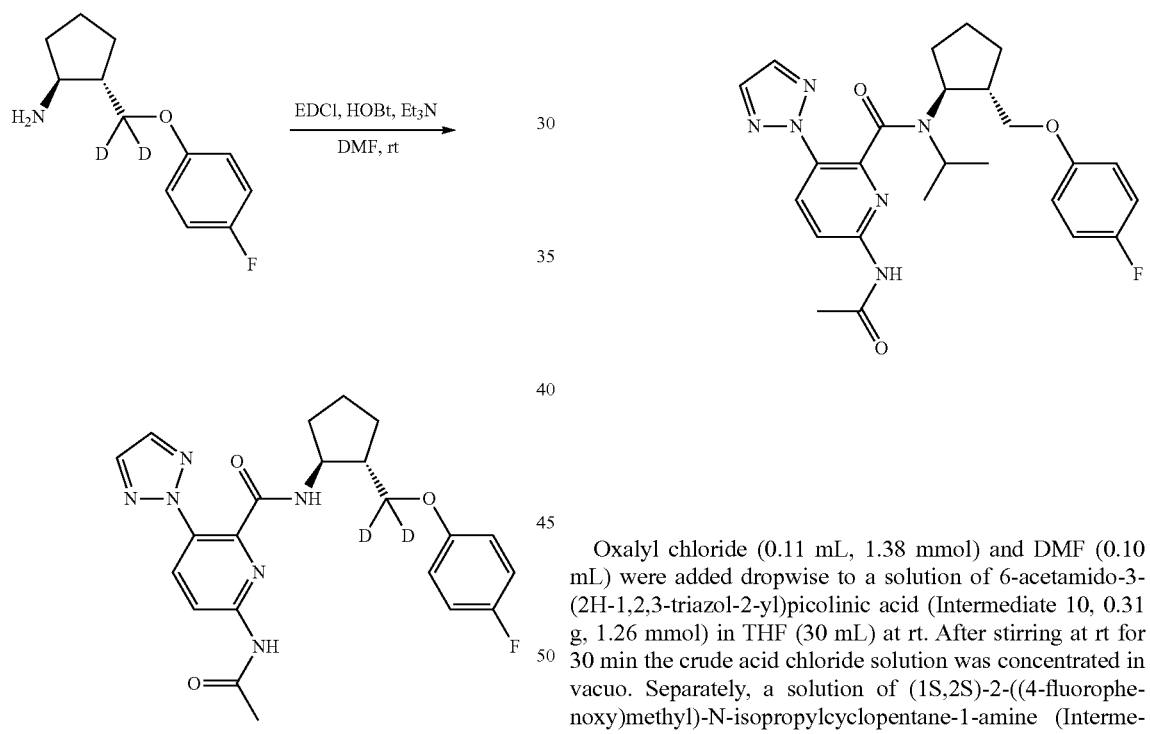

Et₃N (0.09 mL, 0.63 mmol) was added to a suspension of 6-acetamido-3-(2H-1,2,3-triazol-2-yl)picolinic acid (Intermediate 10, 75.0 mg, 0.30 mmol), (1S,2S)-2-((4-fluorophenoxy)methyl-d₂)cyclopentan-1-amine (Intermediate 4, 70.5 mg, 0.33 mmol), EDCI (72.7 mg, 0.38 mmol) and HOBt (58.1 mg, 0.38 mmol) in DCM (2 mL) and the reaction mixture was stirred at rt for 3 d. DCM (2 mL) and aqueous NaOH (1M, 5 mL) were added, the phases were separated and the organic phase was concentrated in vacuo. Purification by gradient flash column chromatography eluting with 0-100% EtOAc in isohexane yielded the title compound (25 mg, 0.057 mmol) as a white solid.
Data in Table 3.

Oxalyl chloride (0.11 mL, 1.38 mmol) and DMF (0.10 mL) were added dropwise to a solution of 6-acetamido-3-(2H-1,2,3-triazol-2-yl)picolinic acid (Intermediate 10, 0.31 g, 1.26 mmol) in THF (30 mL) at rt. After stirring at rt for 30 min the crude acid chloride solution was concentrated in vacuo. Separately, a solution of (1S,2S)-2-((4-fluorophenoxy)methyl)-N-isopropylcyclopentane-1-amine (Intermediate 8, 0.31 g, 1.24 mmol) in THF (20 mL) was added dropwise to a stirred suspension of NaH (60% suspension in mineral oil, 98 mg, 2.47 mmol) in THF (10 mL). After stirring at rt for 30 mins the reaction mixture was cooled to 0° C. and a solution of the crude acid chloride in THF (10 mL) was added dropwise. After stirring at rt for 16 h the reaction mixture was partitioned between saturated aqueous NH₄Cl solution (100 mL) and EtOAc (50 mL), and the aqueous phase was extracted with EtOAc (2×50 mL). The combined organic phases were dried (Na₂SO₄) and concentrated in vacuo. Purification by gradient flash column chromatography eluting with 0-56% EtOAc in hexane yielded the title compound (148 mg, 0.31 mmol) as a yellow solid.
Data in Table 3.

Procedure 4:

Example 11, 6-[(2,2-difluoroacetyl)amino]-N-[(1S, 2S)-2-[(4-fluorophenoxy)methyl]cyclopentyl]-3-(triazol-2-yl)pyridine-2-carboxamide

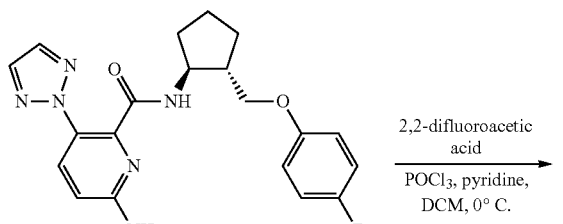

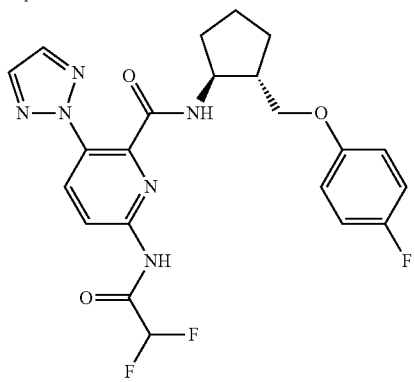

Pyridine (0.21 mL, 2.60 mmol) and POCl₃ (0.17 mL, 1.82 mmol) were added to a solution of 2,2-difluoroacetic acid (0.016 mL, 0.26 mmol) in DCM (3 mL) at 0° C. 6-amino-N-[(1S,2S)-2-[(4-fluorophenoxy)methyl]cyclopentyl]-3-(triazol-2-yl)pyridine-2-carboxamide (Example 4, 50 mg, 0.13 mmol) was added and the reaction mixture was stirred at 0° C. for 1 h before being partitioned between H₂O (20 mL) and EtOAc (15 mL). The phases were separated, and the aqueous phase was extracted with EtOAc (3×10 mL). The combined organic phases were dried (Na₂SO₄) and concentrated in vacuo. Purification by gradient flash column chromatography eluting with 0-50% EtOAc in hexane yielded the title compound (22 mg, 0.05 mmol) as a white solid.
Data in Table 3.

Procedure 5:

Example 16, N-[(1S,2S)-2-[(4-fluorophenoxy)methyl]cyclopentyl]-6-[(2-methoxyacetyl)amino]-3-pyrimidin-2-yl-pyridine-2-carboxamide

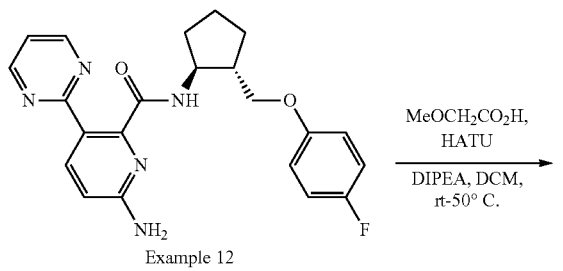

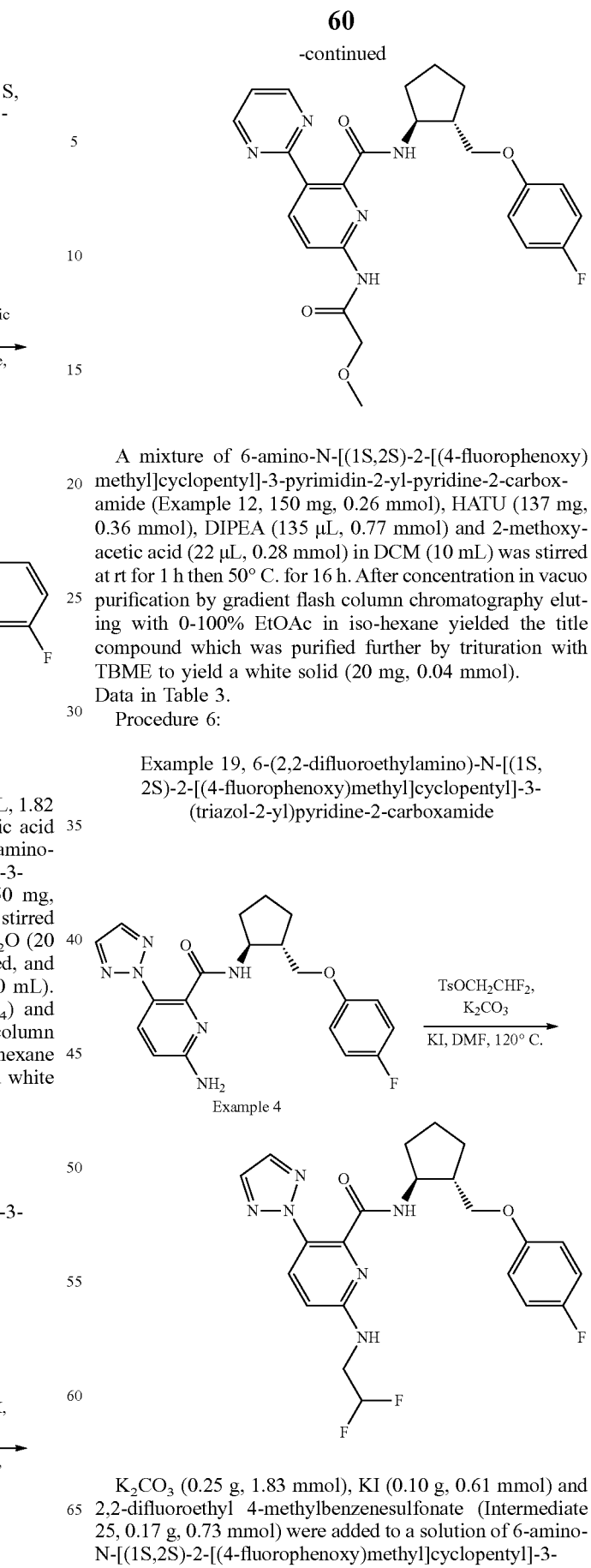

A mixture of 6-amino-N-[(1S,2S)-2-[(4-fluorophenoxy)methyl]cyclopentyl]-3-pyrimidin-2-yl-pyridine-2-carboxamide (Example 12, 150 mg, 0.26 mmol), HATU (137 mg, 0.36 mmol), DIPEA (135 μL, 0.77 mmol) and 2-methoxyacetic acid (22 μL, 0.28 mmol) in DCM (10 mL) was stirred at rt for 1 h then 50° C. for 16 h. After concentration in vacuo purification by gradient flash column chromatography eluting with 0-100% EtOAc in iso-hexane yielded the title compound which was purified further by trituration with TBME to yield a white solid (20 mg, 0.04 mmol).
Data in Table 3.

Procedure 6:

Example 19, 6-(2,2-difluoroethylamino)-N-[(1S, 2S)-2-[(4-fluorophenoxy)methyl]cyclopentyl]-3-(triazol-2-yl)pyridine-2-carboxamide K₂CO₃ (0.25 g, 1.83 mmol), KI (0.10 g, 0.61 mmol) and 2,2-difluoroethyl 4-methylbenzenesulfonate (Intermediate 25, 0.17 g, 0.73 mmol) were added to a solution of 6-amino-N-[(1S,2S)-2-[(4-fluorophenoxy)methyl]cyclopentyl]-3-

(triazol-2-yl)pyridine-2-carboxamide (Example 4, 0.24 g, 0.61 mmol) in DMF (4 mL). After heating at 120° C. for 16 h the reaction mixture was partitioned between H₂O (70 mL) and EtOAc (20 mL). The aqueous phase was extracted with EtOAc (2×20 mL) and the combined organic phases were dried (Na₂SO₄) and concentrated in vacuo. Purification by gradient flash column chromatography eluting with 0-50% EtOAc in hexane yielded the title compound (3.5 mg, 0.01 mmol) as a light yellow solid.
Data in Table 3.
Procedure 7:

Example 20, N-[(1S,2S)-2-[(4-fluorophenoxy)methyl]cyclopentyl]-6-(2-hydroxyethylamino)-3-(triazol-2-yl)pyridine-2-carboxamide

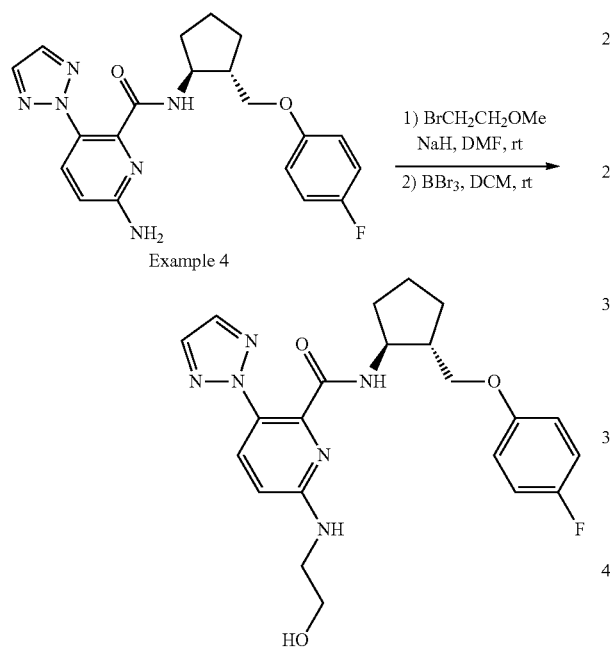

6-Amino-N-[(1S,2S)-2-[(4-fluorophenoxy)methyl]cyclopentyl]-3-(triazol-2-yl)pyridine-2-carboxamide (Example 4, 0.30 g, 0.76 mmol) was added to a suspension of NaH (60% dispersion in mineral oil, 0.15 g, 3.79 mmol) in DMF (3 mL) and allowed to stir for 15 min at rt. 1-Bromo-2-methoxyethane (0.31 g, 2.27 mmol) was added and the reaction mixture was heated at 80° C. for 16 h before partitioning between H₂O (20 mL) and EtOAc (20 mL). The aqueous phase was extracted with EtOAc (3×15 mL), the combined organic phases were dried (Na₂SO₄) and concentrated in vacuo. Purification by gradient flash column chromatography eluting with 0-60% EtOAc in hexane yielded N-((1S,2S)-2-((4-fluorophenoxy)methyl)cyclopentyl)-6-((2-methoxyethyl)amino)-3-(2H-1,2,3-triazol-2-yl)picolinamide (155 mg, approximately 40% purity by LCMS) that was used without further purification.
LCMS (Method 4): m/z 455.2 (ES+), at 2.45 min.
Step 2. BBr₃ in DCM (1M, 0.99 mL, 0.99 mmol) was added to a solution of N-((1S,2S)-2-((4-fluorophenoxy)methyl)cyclopentyl)-6-((2-methoxyethyl)amino)-3-(2H-1,2,3-triazol-2-yl)picolinamide (90 mg, 0.20 mmol) in DCM (5 mL) at −78° C. After stirring at rt for 4 h the reaction mixture was partitioned between saturated aqueous NaHCO₃ solution (30 mL) and EtOAc (30 mL). The aqueous phase was extracted with EtOAc (2×30 mL) and the combined organic phases were dried (Na₂SO₄) and concentrated in vacuo. Purification by preparative HPLC (Waters Sunfire 5 μm C18 column, 250×19 mm, eluting with 35 to 98% MeCN/Solvent A over 19 min at 12 mL/min [where solvent A is 0.2% HCO₂H in H₂O]) yielded the title compound (8 mg, 0.02 mmol).
Data in Table 3.
Procedure 8:

Example 21, 6-acetamido-N-[(1S,2S)-2-[(4-fluorophenoxy)methyl]cyclopentyl]-3-(5-fluoropyrimidin-2-yl)pyridine-2-carboxamide

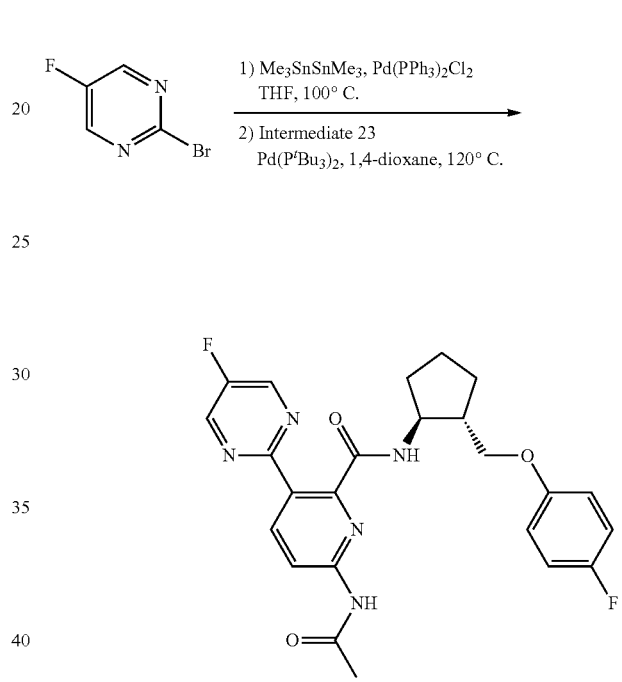

Step 1. Pd(PPh₃)₂Cl₂ (35 mg, 0.042 mmol) was added to a solution of 2-bromo-5-fluoropyrimidine (Intermediate 27, 150 mg, 0.84 mmol) and hexamethylditin (415 mg, 1.27 mmol) in dry THF (3 mL) which had been degassed with Ar. After heating at 100° C. for 16 h in a sealed tube the reaction mixture was filtered through celite and concentrated in vacuo to yield 5-fluoro-2-(trimethylstannyl)pyrimidine as a black gum which was used without analysis or purification in Step 2.
Step 2. A stirred solution of 6-acetamido-3-bromo-N-((1S,2S)-2-((4-fluorophenoxy)methyl)cyclopentyl)picolinamide (Intermediate 23, 100 mg, 0.22 mmol) and 5-fluoro-2-(trimethylstannyl)pyrimidine (270 mg, crude) in 1,4-dioxane (3 mL) was degassed with Ar, then Pd(P'Bu₃)₂ (26 mg, 0.02 mmol) was added and the reaction mixture was heated at 120° C. for 16 h in a sealed tube. After cooling to rt the reaction mixture was partitioned between EtOAc (20 mL) and H₂O (20 mL). The organic phase was separated, washed with brine (10 mL), dried (Na₂SO₄) and concentrated in vacuo. Purification by gradient flash column chromatography eluting with 0-50% EtOAc in petroleum ether yielded the title compound (16 mg, 0.03 mmol) as an off-white solid.
Data in Table 3.

Procedure 9:

Example 22, 6-amino-N-[(1S,2S)-2-[(4-fluorophenoxy)methyl]cyclopentyl]-3-(5-fluoropyrimidin-2-yl)pyridine-2-carboxamide

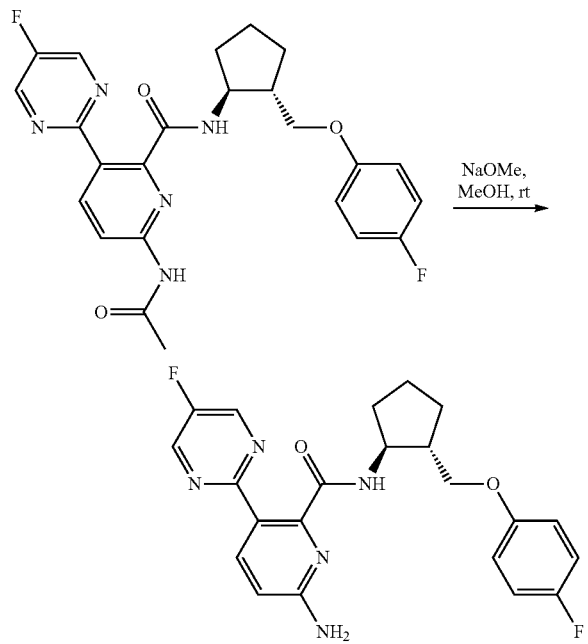

20% NaOMe in MeOH (4 mL) was added to a solution of 6-acetamido-N-[(1S,2S)-2-[(4-fluorophenoxy)methyl]cyclopentyl]-3-(5-fluoropyrimidin-2-yl)pyridine-2-carboxamide (Example 21, 80 mg, 0.17 mmol) in MeOH (2 mL) at rt. After stirring at rt for 48 h the reaction mixture was partitioned between EtOAc (30 mL) and H₂O (25 mL). The organic phase was washed with brine (15 mL), dried (Na₂SO₄) and concentrated in vacuo. Purification by preparative HPLC (Waters XBridge 5 μm C8 column, 150 mm×19 mm, eluting with 10 to 95% MeCN/Solvent A over 18 min [where solvent A is 10 mM NH₄HCO₃ in H₂O]) yielded the title compound (49 mg, 0.12 mmol) as a white solid.

Data in Table 3.

Procedure 10:

Example 26, 6-acetamido-N-[(1S,2S)-2-[(5-fluoro-2-pyridyl)oxymethyl]cyclopentyl]-3-(triazol-2-yl)pyridine-2-carboxamide

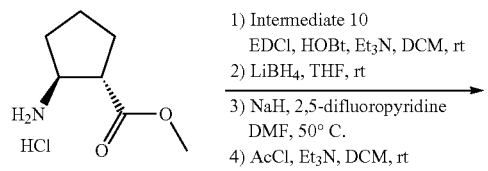

1) Intermediate 10
EDCl, HOBt, Et₃N, DCM, rt
2) LiBH₄, THF, rt
3) NaH, 2,5-difluoropyridine
DMF, 50° C.
4) AcCl, Et₃N, DCM, rt

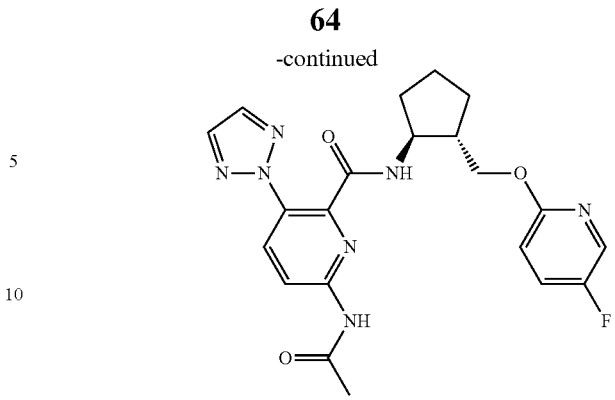

Step 1. Et₃N (0.21 mL, 1.52 mmol) was added to a suspension of methyl (1S,2S)-2-aminocyclopentane-1-carboxylate hydrochloride (Intermediate 28, 120 mg, 0.67 mmol), 6-acetamido-3-(2H-1,2,3-triazol-2-yl)picolinic acid (150 mg, 0.61 mmol), EDCI (145 mg, 0.76 mmol) and HOBt (116 mg, 0.76 mmol) in DCM (3 mL) at rt. The reaction mixture was stirred overnight before the addition of DCM (3 mL) and 1M aqueous HCl (5 mL). The phases were separated and the organic phase was concentrated in vacuo. Purification by gradient flash column chromatography eluting with 0-100% EtOAc in iso-hexane yielded methyl (1S,2S)-2-(6-acetamido-3-(2H-1,2,3-triazol-2-yl)picolinamido)cyclopentane-1-carboxylate (142 mg, 0.38 mmol) as a white solid.

LCMS (Method 5): m/z 373.3 (ES+), at 0.95 min.

¹H NMR: (400 MHz, CDCl₃) δ 8.43 (d, J=8.8 Hz, 1H), 7.97 (dd, J=8.8, 0.5 Hz, 1H), 7.83 (d, J=0.5 Hz, 2H), 7.28 (br. s, 1H), 4.45 (p, J=7.5 Hz, 1H), 3.64 (s, 3H), 2.77 (dt, J=8.9, 7.6 Hz, 1H), 2.24 (s, 3H), 2.16 (dq, J=13.6, 6.8 Hz, 1H), 2.08-1.66 (m, 5H), 1.59 (dq, J=12.6, 7.6 Hz, 1H).

Step 2. LiBH₄ (4M in THF, 0.19 mL, 0.76 mmol) was added slowly to a solution of methyl (1S,2S)-2-(6-acetamido-3-(2H-1,2,3-triazol-2-yl)picolinamido)cyclopentane-1-carboxylate (142 mg, 0.38 mmol) in THF (2 mL) under N₂ at 0° C. The reaction mixture was stirred at 0° C. for 5 min, then rt overnight. Saturated aqueous NH₄Cl solution (3 mL) was added cautiously, followed by EtOAc (10 mL). The phases were separated and the aqueous phase was extracted with EtOAc (2×10 mL). The combined organic phases were concentrated in vacuo and purified by gradient flash column chromatography eluting with 0-10% MeOH in DCM to yield 50 mg of material that ¹H NMR and LCMS analysis indicated was an approximately 1:1 mixture of 6-amino-N-((1S,2S)-2-(hydroxymethyl)cyclopentyl)-3-(2H-1,2,3-triazol-2-yl)picolinamide and 6-acetamido-N-((1S,2S)-2-(hydroxymethyl)cyclopentyl)-3-(2H-1,2,3-triazol-2-yl)picolinamide. The isolated material was used in the subsequent step without further purification.

LCMS (Method 5): m/z 303.4 and 345.4 (ES+), at 0.69 and 0.79 min respectively.

Step 3. Sodium hydride (60% dispersion in mineral oil, 6.4 mg, 0.16 mmol) was added to a solution of an approximately 1:1 mixture of 6-amino-N-((1S,2S)-2-(hydroxymethyl)cyclopentyl)-3-(2H-1,2,3-triazol-2-yl)picolinamide and 6-acetamido-N-((1S,2S)-2-(hydroxymethyl)cyclopentyl)-3-(2H-1,2,3-triazol-2-yl)picolinamide (50 mg) in DMF (2 mL) under N₂. After stirring at rt for 5 min 2,5-difluoropyridine (0.01 mL, 0.15 mmol) was added and the reaction mixture was heated at 50° C. for 24 h. After cooling to rt the reaction mixture was partitioned between EtOAc (10 mL) and H₂O (10 mL) and the aqueous phase was extracted with EtOAc (2×10 mL). The combined organic phases were washed with brine (2×20 mL) and concentrated in vacuo. Purification by gradient flash column chromatography eluting with 0-100% EtOAc in iso-hexane yielded 50 mg of material that ¹H NMR and LCMS analysis indicated was an approximately 1:2 mixture of 6-amino-N-((1S,2S)-2-(((5-fluoropyridin-2-yl)oxy)methyl)cyclopentyl)-3-(2H-1,2,3-triazol-2-yl)picolinamide and 6-acetamido-N-[(1S,2S)-2-[(5-fluoro-2-pyridyl)oxymethyl]cyclopentyl]-3-(triazol-2-yl)pyridine-2-carboxamide as a colourless gum. The isolated material was used in the subsequent step without further purification.

LCMS (Method 5): m/z 398.3 and 440.2 (ES+), at 1.20 and 1.26 min respectively.

Step 4. Acetyl chloride (0.02 mL, 0.23 mmol) was added to a solution of an approximately 1:2 mixture of 6-amino-N-((1S,2S)-2-(((5-fluoropyridin-2-yl)oxy)methyl)cyclopentyl)-3-(2H-1,2,3-triazol-2-yl)picolinamide, 6-acetamido-N-[(1S,2S)-2-[(5-fluoro-2-pyridyl)oxymethyl]cyclopentyl]-3-(triazol-2-yl)pyridine-2-carboxamide (51 mg) and Et₃N (0.03 mL, 0.23 mmol) in DCM (1 mL). After stirring at rt for 15 min DCM (2 mL) and saturated aqueous sodium bicarbonate solution (3 mL) were added, the phases were separated, and the organic phase was concentrated in vacuo. Purification by gradient flash column chromatography eluting with 0-100% EtOAc in iso-hexane yielded the title compound (30 mg, 0.07 mmol) as a white solid.

Data in Table 3.

Further examples prepared by the above procedures are detailed in Table 3.

TABLE 2

Intermediates

| Intermediate | Name | Structure | Data |
|---|---|---|---|
| 1 | (1S,2S)-2-(tert-butoxycarbonylamino)cyclopentane carboxylic acid | 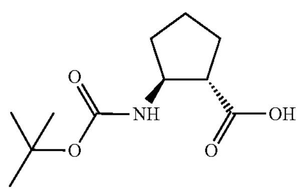 [SMILES: CC(C)(C)OC(=O)N[C@H]1CCC[C@@H]1C(=O)O] | Commercially available, CAS 143679-80-5 |
| 2 | (1S,2S)-2-((4-fluorophenoxy)methyl)cyclopentan-1-amine hydrochloride | 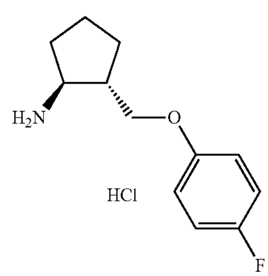 [SMILES: N[C@H]1CCC[C@@H]1COc1ccc(F)cc1 ; Cl] | LCMS (Method 4): m/z 210.2 (ES+), at 1.46 min. ¹H NMR: (400 MHz, DMSO-d₆) δ: 8.03 (br s, 3H), 7.19-7.07 (m, 2H), 7.03-6.92 (m, 2H), 4.07-3.97 (m, 1H), 3.94 (dd, J = 9.4, 6.6 Hz, 1H), 3.34 (d, J = 6.5 Hz, 1H), 2.37-2.27 (m, 1H), 2.08-1.85 (m, 2H), 1.74 (tt, J = 11.7, 4.7 Hz, 1H), 1.64 (ddt, J = 10.0, 8.1, 5.6 Hz, 2H), 1.48 (dq, J = 12.5, 7.4 Hz, 1H). |
| 3 | (1S,2S)-2-((4-chlorophenoxy)methyl)cyclopentan-1-amine hydrochloride | 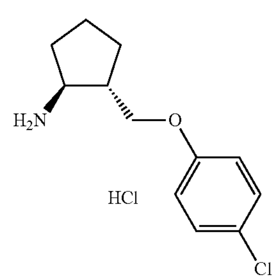 [SMILES: N[C@H]1CCC[C@@H]1COc1ccc(Cl)cc1 ; Cl] | LCMS (Method 3): m/z 226.2 (ES+), at 2.97 min. ¹H NMR: (400 MHz, DMSO-d₆) δ: 8.23 (s, 3H), 7.38-7.29 (m, 2H), 7.05-6.95 (m, 2H), 4.08 (dd, J = 9.5, 5.7 Hz, 1H), 3.96 (dd, J = 9.5, 6.8 Hz, 1H), 3.27-3.41 (m, 1H), 2.36 (h, J = 7.0 Hz, 1H), 2.07-1.85 (m, 2H), 1.81-1.69 (m, 1H), 1.64 (ddd, J = 16.1, 12.8, 6.9 Hz, 2H), 1.47 (dq, J = 12.5, 7.3 Hz, 1H). |
| 4 | (1S,2S)-2-((4-fluorophenoxy)methyl-d₂)cyclopentan-1-amine | 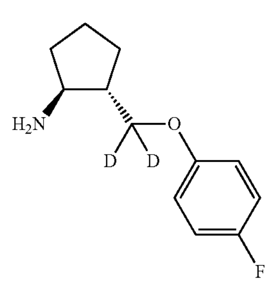 [SMILES: [2H]C([2H])(Oc1ccc(F)cc1)[C@H]1CCC[C@@H]1N] | LCMS (Method 5): m/z 212.4 (ES+), at 1.36 min. ¹H NMR: (400 MHz, DMSO-d₆) δ: 7.09 (ddt, J = 9.0, 6.8, 2.3 Hz, 2H), 6.93 (ddd, J = 9.1, 4.6, 2.3 Hz, 2H), 2.92 (q, J = 7.1 Hz, 1H), 1.83 (tdd, J = 12.4, 8.8, 5.1 Hz, 3H), 1.69-1.44 (m, 2H), 1.42-1.21 (m, 2H). Two exchangeable protons not observed. |

TABLE 2-continued

| Intermediate | Name | Structure | Data |
|---|---|---|---|
| 5 | (1S,2S)-2-((3,4-difluorophenoxy)methyl)cyclopentan-1-amine | 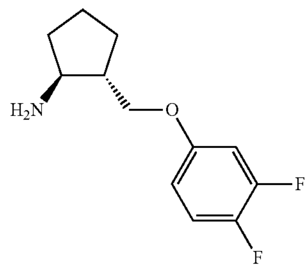 [SMILES: N[C@H]1CCC[C@@H]1COc1ccc(F)c(F)c1] | LCMS (Method 5): m/z 228.4 (ES+), at 1.04 min. $^1$H NMR: (400 MHz, DMSO-$d_6$) δ 7.32 (dt, J = 10.7, 9.3 Hz, 1H), 7.06 (ddd, J = 12.9, 6.8, 3.0 Hz, 1H), 6.76 (dtd, J = 9.3, 3.3, 1.8 Hz, 1H), 4.05-3.92 (m, 1H), 3.83 (dd, J = 9.5, 6.8 Hz, 1H), 2.93 (q, J = 7.0 Hz, 1H), 1.91-1.76 (m, 3H), 1.68-1.58 (m, 1H), 1.58-1.45 (m, 1H), 1.45-1.23 (m, 2H). Two exchangeable protons not observed. |
| 6 | (1S,2S)-2-((2,4-difluorophenoxy)methyl)cyclopentan-1-amine | 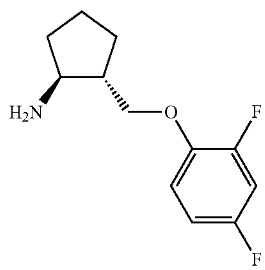 [SMILES: N[C@H]1CCC[C@@H]1COc1ccc(F)cc1F] | LCMS (Method 5): m/z 228.2 (ES+), at 1.41 min. $^1$H NMR: (400 MHz, DMSO-$d_6$) δ 7.28-7.13 (m, 2H), 7.01-6.94 (m, 1H), 4.04 (dd, J = 9.4, 5.2 Hz, 1H), 3.89 (dd, J = 9.5, 6.7 Hz, 1H), 2.91 (q, J = 7.1 Hz, 1H), 1.90-1.73 (m, 4H), 1.69-1.43 (m, 3H), 1.43-1.19 (m, 2H). |
| 7 | (1S,2S)-2-((4-fluorophenoxy)methyl)-N-methylcyclopentan-1-amine hydrochloride | 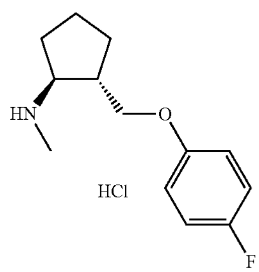 [SMILES: CN[C@H]1CCC[C@@H]1COc1ccc(F)cc1 ; Cl] | LCMS (Method 5): m/z 224.4 (ES+), at 1.69 min. $^1$H NMR: (400 MHz, DMSO-$d_6$) δ 8.79 (s, 2H), 7.13 (t, J = 8.7 Hz, 2H), 6.97 (dd, J = 9.0, 4.5 Hz, 2H), 3.95 (q, J = 9.2, 8.2 Hz, 2H), 2.56 (s, 3H), 2.43 (q, J = 6.5 Hz, 2H), 2.07-1.87 (m, 2H), 1.79-1.60 (m, 3H), 1.55-1.45 (m, 1H). |
| 8 | (1S,2S)-2-((4-fluorophenoxy)methyl)-N-isopropylcyclopentan-1-amine | 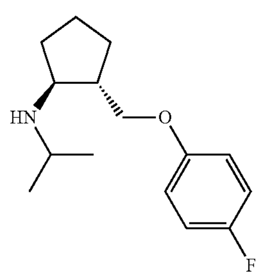 [SMILES: CC(C)N[C@H]1CCC[C@@H]1COc1ccc(F)cc1] | LCMS (Method 2): m/z 252.2 (ES+), at 1.68 min. $^1$H NMR: (400 MHz, DMSO-$d_6$) δ 7.17-7.07 (m, 2H), 6.99-6.90 (m, 2H), 3.89 (qd, J = 9.3, 6.6 Hz, 2H), 3.12 (s, 1H), 3.01 (s, 1H), 2.11 (d, J = 17.2 Hz, 1H), 2.01-1.79 (m 2H), 1.75-1.50 (m, 2H), 1.48-1.34 (m, 2H), 1.07 (dd, J = 10.2, 6.2 Hz, 6H). One exchangeable proton not observed. |
| 9 | 6-acetamido-3-bromopicolinic acid | 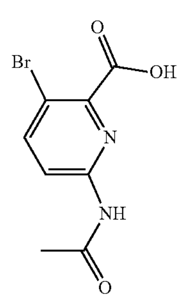 | Commercially available, CAS 882430-69-5 |

TABLE 2-continued

| Intermediate | Name | Structure | Data |
|---|---|---|---|
| 10 | 6-acetamido-3-(2H-1,2,3-triazol-2-yl)picolinic acid | 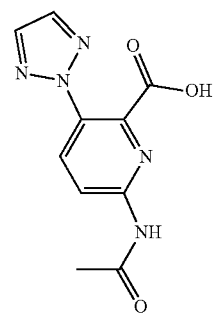 [SMILES: CC(=O)Nc1ccc(-n2nccn2)c(C(=O)O)n1] | LCMS (Method 8): m/z 248.3 (ES+), at 0.51 min. $^1$H NMR: δ 13.59 (s, 1H), 11.05 (s, 1H), 8.36 (d, J = 9.0 Hz, 1H), 8.30 (d, J = 9.0 Hz, 1H), 8.14 (s, 2H), 2.13 (s, 3H). |
| 11 | 6-amino-3-(2H-1,2,3-triazol-2-yl)picolinic acid | 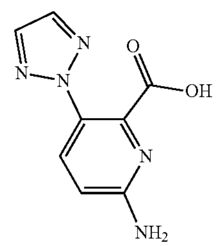 [SMILES: Nc1ccc(-n2nccn2)c(C(=O)O)n1] | LCMS (Method 9): m/z 206.1 (ES+), at 4.77 min. $^1$H NMR: δ 13.10 (s, 1H), 8.00 (s, 2H), 7.77 (d, J = 8.9 Hz, 1H), 6.68 (br. s, 2H), 6.65 (d, J = 8.8 Hz, 1H). |
| 12 | 6-((methoxycarbonyl)amino)-3-(2H-1,2,3-triazol-2-yl)picolinic acid | 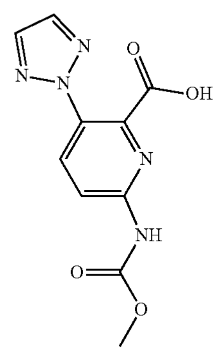 [SMILES: COC(=O)Nc1ccc(-n2nccn2)c(C(=O)O)n1] | LCMS (Method 4): m/z 264.1 (ES+), at 1.01 min. $^1$H NMR: (400 MHz, DMSO-$d_6$) δ 13.59 (s, 1H), 10.79 (s, 1H), 8.30 (d, J = 9.0 Hz, 1H), 8.18-8.10 (m, 3H), 3.71 (s, 3H). |
| 13 | methyl 5-amino-2-bromo-3-fluorobenzoate | 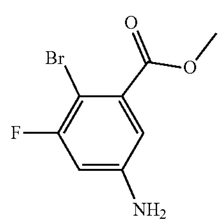 | Commercially available, CAS 1036389-05-5 |
| 14 | 5-acetamido-3-fluoro-2-(2H-1,2,3-triazol-2-yl)benzoic acid | 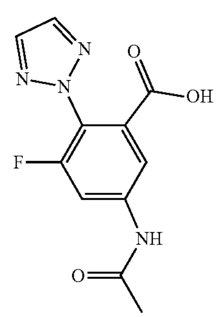 [SMILES: CC(=O)Nc1cc(F)c(-n2nccn2)c(C(=O)O)c1] | LCMS (Method 4): m/z 265.0 (ES+), at 1.40 min. $^1$H NMR: (400 MHz, DMSO-$d_6$ + $D_2O$) δ 7.87 (s, 2H), 7.73 (dd, J = 12.4, 2.3 Hz, 1H), 7.39 (d, J = 2.3 Hz, 1H), 2.06 (s, 3H). |

TABLE 2-continued

Intermediates

| Intermediate | Name | Structure | Data |
|---|---|---|---|
| 15 | 3-amino-6-bromo-2-fluorobenzonitrile | 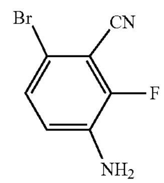 | Commercially available, CAS 1507928-98-4 |
| 16 | 3-acetamido-2-fluoro-6-(pyrimidin-2-yl)benzoic acid | 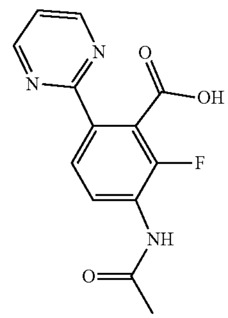 [SMILES: CC(=O)Nc1ccc(-c2ncccn2)c(C(=O)O)c1F] | LCMS (Method 8): m/z 276.2 (ES+), at 0.57 min. $^1$H NMR: (400 MHz, DMSO-$d_6$) δ 9.99 (s, 1H), 8.87 (d, J = 4.9 Hz, 2H), 8.19 (t, J = 8.2 Hz, 1H), 8.02 (d, J = 8.6 Hz, 1H), 7.45 (t, J = 4.9 Hz, 1H), 2.15 (s, 3H). One exchangeable proton not observed. |
| 17 | 2-acetamido-5-bromoisonicotinic acid | 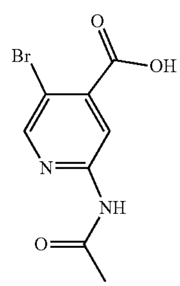 | Commercially available, CAS 871269-03-3 |
| 18 | 2-acetamido-5-(2H-1,2,3-triazol-2-yl)isonicotinic acid | 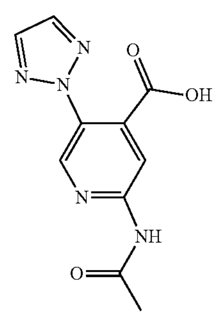 [SMILES: CC(=O)Nc1cc(C(=O)O)c(-n2nccn2)cn1] | LCMS (Method 8): m/z 248.3 (ES+), at 0.34 min. $^1$H NMR: (400 MHz, DMSO-$d_6$) δ 13.82 (br. s, 1H), 11.01 (s, 1H), 8.75 (s, 1H), 8.39 (s, 1H), 8.13 (s, 2H), 2.15 (s, 3H). |
| 19 | methyl 2-acetamido-5-bromoisonicotinate | 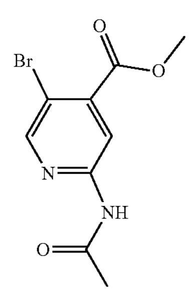 | Commercially available, CAS 1820684-64-7 |

TABLE 2-continued

| Intermediate | Name | Structure | Data |
|---|---|---|---|
| 20 | 2-acetamido-5-(pyrimidin-2-yl)isonicotinic acid | 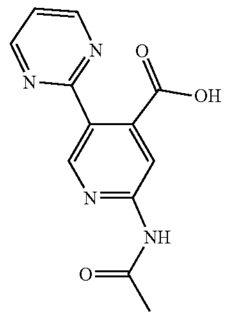 [SMILES: CC(=O)Nc1cc(C(=O)O)c(-c2ncccn2)cn1] | LCMS (Method 4): m/z 259.1 (ES+), at 0.89 min. $^1$H NMR: (400 MHz, DMSO-d$_6$) δ 10.47 (s, 1H), 8.77 (d, J = 4.9 Hz, 2H), 8.53 (d, J = 0.7 Hz, 1H), 8.04 (s, 1H), 7.35 (t, J = 4.9 Hz, 1H), 2.10 (s, 3H). One exchangeable proton not observed. |
| 21 | 2-bromo-5-nitronicotinic acid | 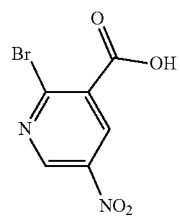 | Commercially available, CAS 914222-92-7 |
| 22 | 5-acetamido-2-(2H-1,2,3-triazol-2-yl)nicotinic acid | 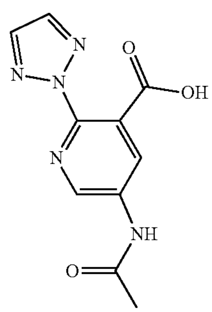 [SMILES: CC(=O)Nc1cnc(-n2nccn2)c(C(=O)O)c1] | LCMS (Method 4): m/z 248 1 (ES+), at 0.81 min $^1$H NMR: (400 MHz, DMSO-d$_6$ + D$_2$O) δ 8.73 (d, J = 2.2Hz, 1H), 8.49 (d, J = 2.3 Hz, 1H), 8.02 (s, 2H), 2.11 (s, 3H). |
| 23 | methyl 6-amino-3-bromopicolinate | 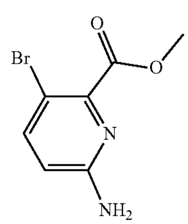 | Commercially available, CAS 178876-83-0 |
| 24 | 6-((tert-butoxycarbonyl)amino)-3-(pyrimidin-2-yl)picolinic acid | 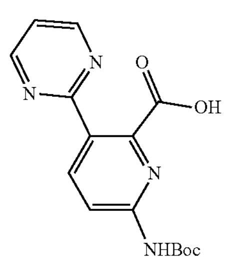 [SMILES: CC(C)(C)OC(=O)Nc1ccc(-c2ncccn2)c(C(=O)O)n1] | LCMS (Method 6): m/z 217 (ES+, M-99), at 1.07 min. $^1$H NMR: (400 MHz, DMSO-d$_6$) δ 10.28 (s, 1H), 8.87 (d, J = 4.9 Hz, 2H), 8.50 (d, J = 8.8 Hz, 1H), 8.02 (d, J = 8.8 Hz, 1H), 7.45 (t, J = 4.9 Hz, 1H), 1.48 (s, 9H). One exchangeable proton not observed. |
| 25 | 2,2-difluoroethyl 4-methylbenzenesulfonate | 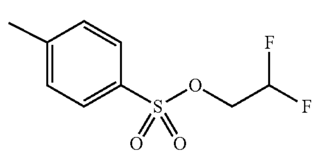 | Commercially available, CAS 135206-84-7 |

TABLE 2-continued

Intermediates

| Intermediate | Name | Structure | Data |
|---|---|---|---|
| 26 | 6-acetamido-3-bromo-N-((1S,2S)-2-((4-fluorophenoxy)methyl)cyclopentyl)picolinamide | 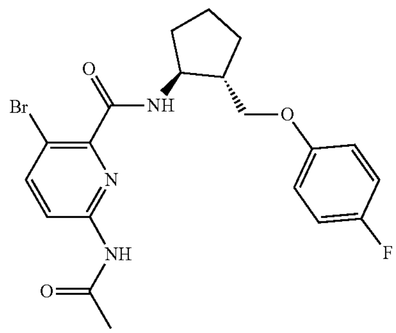 [SMILES: CC(=O)Nc1ccc(Br)c(C(=O)N[C@H]2CCC[C@@H]2COc2ccc(F)cc2)n1] | LCMS (Method 7): m/z 450.2 (ES+), at 2.45 min. $^1$H NMR: (400 MHz, DMSO-$d_6$) δ 10.82 (s, 1H), 8.66 (d, J = 7.0 Hz, 1H), 8.06 (s, 2H), 7.11 (t, J = 6.4 Hz, 2H), 6.96-6.92 (m, 2H), 4.07 (t, J = 7.4 Hz, 2H), 3.89 (t, J = 7.8 Hz, 2H), 2.08 (s, 3H), 1.69-1.49 (m, 6H). |
| 27 | 2-bromo-5-fluoropyrimidine | 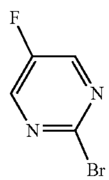 | Commercially available, CAS 947533-45-1 |
| 28 | methyl (1S,2S)-2-aminocyclopentane-1-carboxylate hydrochloride | 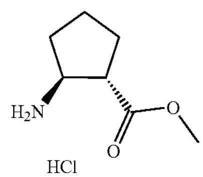 | Commercially available, CAS 1024618-18-5 |

TABLE 3

Example compounds

| Ex. No. | Name | Intermediates/Procedure | $^1$H NMR | LCMS |
|---|---|---|---|---|
| 1 | 5-acetamido-3-fluoro-N-[(1S,2S)-2-[(4-fluorophenoxy)methyl]cyclopentyl]-2-(triazol-2-yl)benzamide | Intermediates 2 and 14 Procedure 1 | (400 MHz, DMSO-$d_6$) δ 10.54 (s, 1H), 8.46 (d, J = 7.9 Hz, 1H), 7.96 (s, 2H), 7.92 (dd, J = 12.7, 2.2 Hz, 1H), 7.43 (dd, J = 2.3, 1.1 Hz, 1H), 7.23-7.01 (m, 2H), 7.01-6.81 (m, 2H), 3.97-3.79 (m, 2H), 3.73 (dd, J = 9.3, 7.7 Hz, 1H), 2.11 (s, 3H), 2.11-2.01 (m, 1H), 1.95-1.72 (m, 2H), 1.73-1.51 (m, 2H), 1.51-1.31 (m, 2H). | m/z 456.2 (M + H) + (ES+), at 2.31 min, 99% (Method 2) |
| 2 | 3-acetamido-2-fluoro-N-[(1S,2S)-2-[(4-fluorophenoxy)methyl]cyclopentyl]-6-pyrimidin-2-yl-benzamide | Intermediates 2 and 16 Procedure 1 | (500 MHz, DMSO-$d_6$) δ 9.95 (s, 1H), 8.77 (d, J = 4.8 Hz, 2H), 8.47 (d, J = 7.8 Hz, 1H), 8.18 (t, J = 7.9 Hz, 1H), 7.97 (d, J = 8.7 Hz, 1H), 7.36 (t, J = 4.8 Hz, 1H), 7.22-7.05 (m, 2H), 7.02-6.88 (m, 2H), 4.14-3.98 (m, 2H), 3.87 (dd, J = 9.3, 8.0 Hz, 1H), 3.32 (s, 3H), 2.24 (td, J = 8.0, 4.3 Hz, 1H), 2.04-1.93 (m, 1H), 1.89 (dq, J = 14.7, 6.8 Hz, 1H), 1.64 (p, J = 7.2, 6.7 Hz, 2H), 1.60-1.52 (m, 1H), 1.47 (dq, J = 12.6, 7.9 Hz, 1H). | m/z 467.1 (M + H) + (ES+), at 4.02 min, 100% (Method 1) |
| 3 | 6-acetamido-N-[(1S,2S)-2-[(4-fluorophenoxy)methyl]cyclopentyl]-3-(triazol-2-yl)pyridine-2-carboxamide | Intermediates 2 and 10 Procedure 1 | (400 MHz, DMSO-$d_6$) δ 10.98 (s, 1H), 8.59 (d, J = 7.9 Hz, 1H), 8.40-8.17 (m, 2H), 7.96 (s, 2H), 7.28-7.05 (m, 2H), 7.05-6.84 (m, 2H), 4.05 (dd, J = 9.3, 4.2 Hz, 1H), 3.98 (q, J = 7.6 Hz, 1H), 3.83 (dd, J = 9.3, 7.9 Hz, 1H), 2.20 (td, J = 7.9, 4.2 Hz, 1H), 2.13 (s, 3H), 1.89 (tq, J = 13.5, 7.3, 6.6 Hz, 2H), 1.72-1.40 (m, 4H). | m/z 439.2 (M + H) + (ES+), at 2.29 min, 100% (Method 2) |
| 4 | 6-amino-N-[(1S,2S)-2-[(4-fluorophenoxy)methyl]cyclopentyl]-3-(triazol-2-yl)pyridine-2-carboxamide | Intermediates 2 and 11 Procedure 1 | (400 MHz, DMSO-$d_6$) δ 8.36 (d, J = 8.1 Hz, 1H), 7.83 (s, 2H), 7.69 (d, J = 8.8 Hz, 1H), 7.19-7.07 (m, 2H), 6.93 (ddd, J = 6.8, 5.4, 3.1 Hz, 2H), 6.70-6.52 (m, 3H), 4.01 (dd, J = 9.3, 4.2 Hz, 1H), 3.93 (p, J = 7.8 Hz, 1H), 3.79 (t, J = 8.6 Hz, 1H), 2.20 (td, J = 8.1, 4.2 Hz, 1H), 1.87 (dh, J = 11.7, 2.8 Hz, 2H), 1.76-1.38 (m, 4H). | m/z 397.2 (M + H) + (ES+), at 2.11 min, 96% (Method 4) |
| 5 | 6-acetamido-N-[(1S,2S)-2-[(4-fluorophenoxy)methyl]cyclopentyl]-N-methyl-3-(triazol-2-yl)pyridine-2- | Intermediates 7 and 10 Procedure 2 | (400 MHz, DMSO-$d_6$) δ 10.92 (s, 0.5H), 10.66 (s, 0.6H), 8.39-8.20 (m, 1.7H), 8.14 (d, J = 9.1 Hz, 0.5H), 7.99 (s, 1.1H), 7.89 (s, 1.0H), 7.08 (t, J = 8.7 Hz, 1.1H), 7.02-6.82 (m, 2.3H), 6.60 (s, 1.1H), 4.80-4.57 (m, 0.5H), 4.02 (d, J = 9.3 Hz, 0.4H), 3.86 (t, J = 8.1 Hz, 1.1H), 3.67 (dd, J = 18.4, 9.6 Hz, 1.2H), 2.83 (s, 1.9H), 2.69 (s, 1.6H), 2.32 (br s, 0.6H), | m/z 453.1 (M + H) + (ES+), at 4.27 and 4.57 min, 97% (Method 1) |

TABLE 3-continued

Example compounds

| Ex. No. | Name | Intermediates/ Procedure | ¹H NMR | LCMS |
|---|---|---|---|---|
| | carboxamide | | 2.07 (s, 1.6H), 2.00 (s, 1.7H), 1.96-1.85 (m, 0.3H), 1.85-1.46 (m, 2.7H), 1.36 (br s, 1.5H). Compound shows atropisomerism. | |
| 6 | 6-acetamido-N-[(1S,2S)-2-[(4-chlorophenoxy)methyl]cyclopentyl]-3-(triazol-2-yl)pyridine-2-carboxamide | Intermediates 3 and 10 Procedure 1 | (400 MHz, DMSO-$d_6$) δ 10.94 (s, 1H), 8.55 (d, J = 7.9 Hz, 1H), 8.28 (d, J = 9.0 Hz, 1H), 8.22 (d, J = 8.9 Hz, 1H), 7.95 (s, 2H), 7.43-7.25 (m, 2H), 7.05-6.85 (m, 2H), 4.05 (dd, J = 9.3, 4.3 Hz, 1H), 3.98 (t, J = 7.6 Hz, 1H), 3.89-3.76 (m, 1H), 2.20 (td, J = 8.0, 4.3 Hz, 1H), 2.11 (s, 3H), 1.88 (dq, J = 13.9, 6.4 Hz, 2H), 1.73-1.40 (m, 4H). | m/z 455.1, 457.1 (M + H) + (ES+), at 4.64 min, 97% (Method 1) |
| 7 | 6-acetamido-N-[(1S,2S)-2-[(4-fluorophenoxy)methyl]cyclopentyl]-N-isopropyl-3-(triazol-2-yl)pyridine-2-carboxamide | Intermediates 8 and 10 Procedure 3 | (400 MHz, DMSO-$d_6$) δ 10.88 (s, 1.1H), 10.62 (s, 0.3H), 8.30 (d, J = 3.1 Hz, 2.6H), 8.28-7.92 (m, 3.4H), 7.24-7.10 (m, 1.3H), 7.08-6.91 (m, 1.7H), 6.72 (s, 0.8H), 4.00 (d, J = 11.3 Hz, 1.4H), 3.88 (dd, J = 9.3, 6.7 Hz, 0.7H), 3.72 (dd, J = 9.2, 5.7 Hz, 0.5H), 3.61 (s, 2.4H), 3.54 (q, J = 8.5 Hz, 0.6H), 2.31-2.18 (m, 0.1H), 2.13 (s, 2.1H), 2.06-1.88 (m, 1.2H), 1.82 (d, J = 10.4 Hz, 1.0H), 1.60 (dd, J = 13.0, 6.5 Hz, 0.2H), 1.46 (t, J = 7.0 Hz, 3.1H), 1.33 (s, 0.3H), 1.21-0.99 (m, 3.1H), 0.81 (s, 1.1H). Compound shows atropisomerism. | m/z 481.3 (M + H) + (ES+), at 2.60 and 2.70 min, 97% (Method 2) |
| 8 | 6-acetamido-N-[(1S,2S)-2-[dideuterio-(4-fluorophenoxy)methyl]cyclopentyl]-3-(triazol-2-yl)pyridine-2-carboxamide | Intermediates 4 and 10 Procedure 2 | (400 MHz, DMSO-$d_6$) δ 10.94 (s, 1H), 8.54 (d, J = 7.8 Hz, 1H), 8.28 (d, J = 8.9 Hz, 1H), 8.22 (d, J = 9.0 Hz, 1H), 7.94 (s, 2H), 7.25-7.04 (m, 2H), 7.02-6.80 (m, 2H), 4.10-3.89 (m, 1H), 2.18 (q, J = 7.9 Hz, 1H), 2.11 (s, 3H), 1.87 (tt, J = 14.4, 6.7 Hz, 2H), 1.73-1.25 (m, 4H). | m/z 441.1 (M + H) + (ES+), at 4.05 min, 97% (Method 1) |
| 9 | 6-acetamido-N-[(1S,2S)-2-[(3,4-difluorophenoxy)methyl]cyclopentyl]-3-(triazol-2-yl)pyridine-2-carboxamide | Intermediates 5 and 10 Procedure 2 | (400 MHz, DMSO-$d_6$) δ 10.93 (s, 1H), 8.55 (d, J = 7.8 Hz, 1H), 8.28 (d, J = 8.9 Hz, 1H), 8.22 (d, J = 8.9 Hz, 1H), 7.95 (s, 2H), 7.41-7.22 (m, 1H), 7.02 (ddd, J = 12.7, 6.8, 3.0 Hz, 1H), 6.86-6.66 (m, 1H), 4.04 (dd, J = 9.5, 4.2 Hz, 1H), 4.01-3.93 (m, 1H), 3.92-3.77 (m, 1H), 2.20 (td, J = 7.9, 4.3 Hz, 1H), 2.11 (s, 3H), 1.99-1.78 (m, 2H), 1.72-1.33 (m, 4H). | m/z 457.1 (M + H) + (ES+), at 4.26 min, 97% (Method 1) |
| 10 | methyl N-[6-[[(1S,2S)-2-[(4-fluorophenoxy)methyl]cyclopentyl]carbamoyl]-5-(triazol-2-yl)-2-pyridyl]carbamate | Intermediates 2 and 12 Procedure 1 | (400 MHz, DMSO-$d_6$) δ 10.73 (s, 1H), 8.55 (d, J = 7.8 Hz, 1H), 8.24 (d, J = 9.0 Hz, 1H), 8.08 (d, J = 9.0 Hz, 1H), 7.96 (s, 2H), 7.22-7.04 (m, 2H), 7.01-6.82 (m, 2H), 4.02 (d, J = 4.3 Hz, 1H), 3.97 (s, 1H), 3.81 (dd, J = 9.3, 7.9 Hz, 1H), 3.70 (s, 3H), 2.19 (td, J = 7.9, 4.2 Hz, 1H), 1.89 (tq, J = 13.2, 7.0, 6.5 Hz, 2H), 1.61 (dq, J = 12.5, 6.3, 5.7 Hz, 2H), 1.57-1.39 (m, 2H). | m/z 455.2 (M + H) + (ES+), at 2.03 min, 100% (Method 4) |
| 11 | 6-[(2,2-difluoroacetyl)amino]-N-[(1S,2S)-2-[(4-fluorophenoxy)methyl]cyclopentyl]-3-(triazol-2-yl)pyridine-2-carboxamide | Synthesized from Example 4 and 2,2-difluoroacetic acid Procedure 4 | (400 MHz, DMSO-$d_6$) δ 11.90 (s, 1H), 8.66 (d, J = 7.9 Hz, 1H), 8.38 (d, J = 8.9 Hz, 1H), 8.28 (d, J = 8.9 Hz, 1H), 8.00 (s, 2H) 7.23-7.03 (m, 2H), 7.02-6.86 (m, 2H), 6.42 (t, J = 53.5 Hz, 1H), 4.18-3.94 (m, 2H), 3.84 (dd, J = 9.3, 7.8 Hz, 1H), 2.21 (td, J = 7.9, 4.2 Hz, 1H), 2.00-1.80 (m, 2H), 1.71-1.60 (m, 2H), 1.60-1.41 (m, 2H). | m/z 475.2 (M + H) + (ES+), at 2.46 min, 98% (Method 2) |
| 12 | 6-amino-N-[(1S,2S)-2-[(4-fluorophenoxy)methyl]cyclopentyl]-3-pyrimidin-2-yl-pyridine-2-carboxamide | Intermediates 2 and 24 Procedure 1, then TFA, DCM, rt | (500 MHz, DMSO-$d_6$) δ 8.69 (d, J = 4.8 Hz, 2H), 8.32 (d, J = 7.9 Hz, 1H), 8.26 (d, J = 8.9 Hz, 1H), 7.28 (t, J = 4.9 Hz, 1H), 7.22-7.07 (m, 2H), 7.03-6.88 (m, 2H), 6.72 (d, J = 9.0 Hz, 1H), 4.09 (dd, J = 9.3, 4.3 Hz, 1H), 4.02 (p, J = 7.5 Hz, 1H), 3.86 (dd, J = 9.3, 8.0 Hz, 1H), 2.32-2.15 (m, 1H), 2.03-1.79 (m, 2H), 1.72-1.53 (m, 3H), 1.48 (dt, J = 12.7, 7.6 Hz, 1H). Two exchangeable protons not observed. | m/z 408.1 (M + H) + (ES+), at 3.70 min, 98% (Method 1) |
| 13 | 6-(cyclopropanecarbonylamino)-N-[(1S,2S)-2-[(4-fluorophenoxy)methyl]cyclopentyl]-3-(triazol-2-yl)pyridine-2-carboxamide | Synthesized from Example 4 and cyclopropane carboxylic acid Procedure 4 | (400 MHz, DMSO-$d_6$) δ 11.28 (s, 1H), 8.60 (d, J = 7.9 Hz, 1H), 8.29 (d, J = 9.0 Hz, 1H), 8.23 (d, J = 9.0 Hz, 1H), 7.96 (s, 2H), 7.20-7.07 (m, 2H), 7.00-6.86 (m, 2H), 4.05 (dd, J = 9.2, 4.1 Hz, 1H), 3.99 (q, J = 7.7 Hz, 1H), 3.83 (dd, J = 9.3, 7.8 Hz, 1H), 2.21 (td, J = 8.0, 4.2 Hz, 1H), 2.10-2.00 (m, 1H), 1.89 (tt, J = 14.2, 6.7 Hz, 2H), 1.71-1.59 (m, 2H), 1.59-1.40 (m, 2H), 0.94-0.76 (m, 4H). | m/z 465.3 (M + H) + (ES+), at 2.46 min, 100% (Method 2) |
| 14 | 6-acetamido-N-[(1S,2S)-2-[(4-fluorophenoxy)methyl]cyclopentyl]-3-pyrimidin-2-yl-pyridine-2-carboxamide | Intermediates 2 and 9 Procedure 1, then Stille coupling | (400 MHz, DMSO-$d_6$) δ 10.86 (s, 1H), 8.73 (dd, J = 4.9, 0.8 Hz, 2H), 8.44 (d, J = 8.7 Hz, 1H), 8.35 (d, J = 7.7 Hz, 1H), 8.21 (d, J = 8.7 Hz, 1H), 7.34 (td, J = 4.9, 0.8 Hz, 1H), 7.16-7.03 (m, 2H), 6.99-6.84 (m, 2H), 4.05 (dd, J = 8.4, 4.2 Hz, 1H), 3.99 (t, J = 7.4 Hz, 1H), 3.83 (t, J = 8.6 Hz, 1H), 2.25 (td, J = 7.9, 4.3 Hz, 1H), 2.10 (s, 3H), 2.01-1.80 (m, 2H), 1.58 (tq, J = 15.7, 7.9 Hz, 3H), 1.52-1.35 (m, 1H). | m/z 450.1 (M + H) + (ES+), at 3.81 min, 100% (Method 1) |
| 15 | 6-acetamido-N-[(1S,2S)-2-[(4-chlorophenoxy)methyl]cyclopentyl]-3-pyrimidin-2-yl-pyridine-2-carboxamide | Intermediates 3 and 9 Procedure 1 then Stille coupling | (400 MHz, DMSO-$d_6$) δ 10.92 (s, 1H), 8.75 (d, J = 4.8 Hz, 2H), 8.46 (d, J = 8.8 Hz, 1H), 8.41 (d, J = 7.7 Hz, 1H), 8.24 (d, J = 8.7 Hz, 1H), 7.48-7.23 (m, 3H), 7.05-6.78 (m, 2H), 4.10 (dd, J = 9.4, 4.3 Hz, 1H), 4.01 (t, J = 7.5 Hz, 1H), 3.87 (t, J = 8.7 Hz, 1H), 2.27 (td, J = 8.0, 4.3 Hz, 1H), 2.12 (s, 3H), 2.05-1.83 (m, 2H), 1.75-1.52 (m, 3H), 1.46 (dq, J = 14.9, 7.4 Hz, 1H). | m/z 466.2 (M + H) + ES+), at 2.33 min, 100% (Method 2) |
| 16 | N-[(1S,2S)-2-[(4-fluorophenoxy)methyl]cyclopentyl]-6- | Synthesized from Example 12 and 2-meth- | (500 MHz, DMSO-$d_6$) δ 10.50 (s, 1H), 8.77 (d, J = 4.9 Hz, 2H), 8.48 (d, J = 7.4 Hz, 1H), 8.42 (d, J = 7.7 Hz, 1H), 8.25 (d, J = 8.6 Hz, 1H), 7.38 (t, J = 4.9 Hz, 1H), 7.23-7.04 (m, | m/z 480.1 (M + H) + (ES+), at 4.19 min, 100% |

TABLE 3-continued

Example compounds

| Ex. No. | Name | Intermediates/ Procedure | ¹H NMR | LCMS |
|---|---|---|---|---|
|  | [(2-methoxy-acetyl)amino]-3-pyrimidin-2-yl-pyridine-2-carboxamide | oxyacetic acid Procedure 5 | 2H), 7.04-6.84 (m, 2H), 4.12 (s, 2H), 4.07 (dd, J = 9.6, 4.3 Hz, 1H), 4.01 (q, J = 7.5 Hz, 1H), 3.86 (dd, J = 9.3, 7.9 Hz, 1H), 3.38 (s, 3H), 2.28 (td, J = 8.0, 4.4 Hz, 1H), 1.92 (ddt, J = 27.6, 14.1, 7.1 Hz, 2H), 1.62 (dd, J = 17.3, 14.7, 7.7 Hz, 3H), 1.55-1.37 (m, 1H). | (Method 1) |
| 17 | 6-acetamido-N-[(1S,2S)-2-[(2,4-difluorophenoxy)methyl]cyclopentyl]-3-(triazol-2-yl)pyridine-2-carboxamide | Intermediates 6 (free base) and 10 Procedure 2 | (400 MHz, DMSO-d₆) δ 10.94 (s, 1H), 8.56 (d, J = 7.8 Hz, 1H), 8.28 (d, J = 9.0 Hz, 1H), 8.22 (d, J = 9.0 Hz, 1H), 7.95 (s, 2H), 7.26 (ddd, J = 11.7, 8.8, 3.1 Hz, 1H), 7.15 (td, J = 9.4, 5.5 Hz, 1H), 7.08-6.88 (m, 1H), 4.11 (dd, J = 9.4, 4.2 Hz, 1H), 3.98 (p, J = 7.5 Hz, 1H), 3.91 (dd, J = 9.4, 7.8 Hz, 1H), 2.21 (td, J = 7.9, 4.1 Hz, 1H), 2.15-2.08 (m, 3H), 1.98-1.81 (m, 2H), 1.71-1.39 (m, 4H). | m/z 457.1 (M + H) + (ES+), at 4.14 min, 100% (Method 1) |
| 18 | 6-acetamido-N-[(1S,2S)-2-[(4-fluorophenoxy)methyl]cyclopentyl]-N-methyl-3-pyrimidin-2-yl-pyridine-2-carboxamide | Intermediates 7 and 9 Procedure 1, then Stille coupling | (400 MHz, DMSO-d₆) δ 10.95 (s, 0.6H), 10.73 (s, 0.6H), 8.80 (s, 1.4H), 8.74 (d, J = 4.9 Hz, 1.1H), 8.60 (dd, J = 12.7, 8.8 Hz, 1.1H), 8.25 (d, J = 8.8 Hz, 0.5H), 8.14 (d, J = 8.7 Hz, 0.5H), 7.36 (s, 0.8H), 7.31 (t, J = 4.9 Hz, 0.5H), 7.12 (t, J = 8.8 Hz, 1.2H), 7.03-6.85 (m, 2.4H), 6.61 (s, 1.2H), 4.74 (t, J = 8.5 Hz, 0.5H), 4.11 (d, J = 8.7 Hz, 0.5H), 3.93 (t, J = 8.4 Hz, 1.2H), 3.74 (dd, J = 16.8, 8.2 Hz, 1.3H), 2.91 (s, 1.6H), 2.74 (s, 1.5H), 2.36 (d, J = 18.1 Hz, 0.7H), 2.09 (d, J = 27.1 Hz, 3H), 1.99 (dd, J = 13.0, 7.2 Hz, 0.2H), 1.93-1.66 (m, 1.5H), 1.66-1.49 (m, 0.6H), 1.49-1.28 (m, 1.5H). Compound shows atropisomerism. | m/z 464.2 (M + H) + (ES+), at 2.03 and 2.18 min, 100% (Method 2) |
| 19 | 6-(2,2-difluoro-ethylamino)-N-[(1S,2S)-2-[(4-fluoro-phenoxy)methyl]cyclopentyl]-3-(triazol-2-yl)pyridine-2-carboxamide | Synthesized from Example 4 and intermediate 25 Procedure 6 | (400 MHz, Chloroform-d) δ 7.80 (s, 2H), 7.65 (d, J = 8.7 Hz, 1H), 7.36 (d, J = 8.2 Hz, 1H), 6.98-6.87 (m, 2H), 6.79 (ddd, J = 6.7, 5.3, 3.1 Hz, 2H), 6.69 (d, J = 8.8 Hz, 1H), 5.96 (tt, J = 56.1, 4.0 Hz, 1H), 4.10 (q, J = 7.9 Hz, 1H), 4.02 (dd, J = 9.1, 5.1 Hz, 1H), 3.93-3.73 (m, 3H), 2.32-2.10 (m, 2H), 2.10-1.96 (m, 1H), 1.73 (dq, J = 12.8, 8.0 Hz, 2H), 1.52 (ddd, J = 13.9, 8.3, 5.9 Hz, 2H). One exchangeable proton not observed. | m/z 461.2 (M + H) + (ES+), at 2.51 min, 100% (Method 2) |
| 20 | N-[(1S,2S)-2-[(4-fluorophenoxy)methyl]cyclopentyl]-6-(2-hydroxyethylamino)-3-(triazol-2-yl)pyridine-2-carboxamide | Synthesized from Example 4 and 1-bromo-2-methoxyethane Procedure 7 | (400 MHz, Methanol-d₄) δ 7.77 (s, 2H), 7.70 (d, J = 8.9 Hz, 1H), 7.07-6.96 (m, 2H), 6.96-6.86 (m, 2H), 6.74 (d, J = 8.9 Hz, 1H), 4.08 (dd, J = 8.9, 4.6 Hz, 2H), 3.87 (dd, J = 9.3, 7.5 Hz, 1H), 3.74 (t, J = 5.7 Hz, 2H), 3.56 (t, J = 5.7 Hz, 2H), 2.28 (pd, J = 8.1, 4.7 Hz, 1H), 2.14-1.94 (m, 2H), 1.84-1.69 (m, 2H), 1.69-1.48 (m, 2H). Three exchangeable protons not observed. | m/z 441.2 (M + H ) + (ES+), at 1.87 min, 98% (Method 4) |
| 21 | 6-acetamido-N-[(1S,2S)-2-[(4-fluorophenoxy)methyl]cyclopentyl]-3-(5-fluoropyrimidin-2-yl)pyridine-2-carboxamide | Intermediate 26 and 5-fluoro-2-(trimethyl-stannyl)pyrimidine Procedure 8 | (400 MHz, DMSO-d₆) δ 10.90 (s, 1H), 8.81 (s, 2H), 8.41 (dd, J = 8.3, 5.8 Hz, 2H), 8.24(d, J = 8.8 Hz, 1H), 7.11 (t, J = 8.8 Hz, 2H), 7.01-6.85 (m, 2H), 4.12-3.96 (m, 2H), 3.87 (t, J = 8.6 Hz, 1H), 2.31-2.19 (m, 1H), 2.13 (s, 3H), 2.04-1.81 (m, 2H), 1.76-1.39 (m, 4H). | m/z 468.1 (M + H) + (ES+), at 2.30 min, 97% (Method 7) |
| 22 | 6-amino-N-[(1S,2S)-2-[(4-fluorophenoxy)methyl]cyclopentyl]-3-(5-fluoropyrimidin-2-yl)pyridine-2-carboxamide | Synthesized from Example 21 Procedure 9 | (400 MHz, DMSO-d₆) δ 8.68 (s, 2H), 8.17 (d, J = 7.8 Hz, 1H), 8.03 (d, J = 8.7 Hz, 1H), 7.11 (t, J = 8.8 Hz, 2H), 7.05-6.87 (m, 2H), 6.72-6.45 (m, 3H), 4.07 (dd, J = 9.3, 4.2 Hz, 1H), 3.99 (t, J = 7.6 Hz, 1H), 3.85 (dd, J = 16.1, 7.7 Hz, 1H), 2.30-2.18 (m, 1H), 2.05-1.82 (m, 2H), 1.74-1.40 (m, 4H). | m/z 425.9 (M + H) + (ES+), at 2.16 min, 95% (Method 7) |
| 23 | 2-acetamido-N-[(1S,2S)-2-[(4-fluorophenoxy)methyl]cyclopentyl]-5-(triazol-2-yl)pyridine-4-carboxamide | Intermediates 2 and 18 Procedure 1 | (400 MHz, DMSO-d₆) δ 10.93 (s, 1H), 8.75 (s, 1H), 8.61 (d, J = 7.8 Hz, 1H), 8.20 (s, 1H), 7.99 (s, 2H), 7.24-7.05 (m, 2H), 7.02-6.87 (m, 2H), 4.06-3.94 (m, 2H), 3.84 (dd, J = 9.4, 7.6 Hz, 1H), 2.22-2.16 (m, 1H), 2.14 (s, 3H), 2.00-1.79 (m, 2H), 1.61 (p, J = 7.1, 6.7 Hz, 2H), 1.56-1.38 (m, 2H). | m/z 439.2 (M + H) + (ES+), at 2.26 min, 100% (Method 2) |
| 24 | 2-acetamido-N-[(1S,2S)-2-[(4-fluorophenoxy)methyl]cyclopentyl]-5-pyrimidin-2-yl-pyridine-4-carboxamide | Intermediates 2 and 20 Procedure 1 | (400 MHz, DMSO-d₆) δ 10.89 (s, 1H), 9.00 (s, 1H), 8.78 (d, J = 4.9 Hz, 2H), 8.44 (d, J = 7.7 Hz, 1H), 8.14 (s, 1H), 7.39 (t, J = 4.9 Hz, 1H), 7.21-7.06 (m, 2H), 7.06-6.88 (m, 2H), 4.16-3.97 (m, 2H), 3.88 (dd, J = 9.4, 7.8 Hz, 1H), 2.31-2.19 (m, 1H), 2.16 (s, 3H), 1.96 (dt, J = 13.2, 7.0 Hz, 1H), 1.87 (p, J = 6.7 Hz, 1H), 1.76-1.36 (m, 4H). | m/z 450.2 (M + H) + (ES+), at 1.84 min, 99% (Method 4) |
| 25 | 5-acetamido-N-[(1S,2S)-2-[(4-fluorophenoxy)methyl]cyclopentyl]-2-(triazol-2-yl)pyridine-3-carboxamide | Intermediates 2 and 22 Procedure 1 | (400 MHz, DMSO-d₆) δ 10.55 (s, 1H), 8.75 (d, J = 2.5 Hz, 1H), 8.53 (d, J = 7.8 Hz, 1H), 8.24 (d, J = 2.5 Hz, 1H), 7.96 (s, 2H), 7.23-7.06 (m, 2H), 7.02-6.85 (m, 2H), 4.04-3.89 (m, 2H), 3.81 (dd, J = 9.4, 7.6 Hz, 1H), 2.19-2.06 (m, 4H), 1.87 (dp, J = 21.6, 7.0 Hz, 1H), 1.60 (p, J = 7.1 Hz, 2H), 1.53-1.36 (m, 2H). | m/z 439.2 (M + H) + (ES+), at 2.13 min, 100% (Method 2) |
| 26 | 6-acetamido-N-[(1S,2S)-2-[(5-fluoro-2-pyridyl)oxy-methyl]cyclopentyl]- | Intermediates 10 and 28 Procedure 10 | (400 MHz DMSO-d₆) δ 10.94 (s, 1H), 8.52 (d, J = 8.0 Hz, 1H), 8.28 (d, J = 9.0 Hz, 1H), 8.22 (d, J = 8.9 Hz, 1H), 8.14 (d, J = 3.1 Hz, 1H), 7.96 (s, 2H), 7.66 (ddd, J = 9.1, 8.1, 3.2 Hz, 1H), 6.95-6.74 (m, 1H), 4.34 (dd, J = 10.4, 4.5 Hz, 1H), | m/z 440.1 (M + H) + (ES+), at 3.53 min, 97% (Method 1) |

TABLE 3-continued

Example compounds

| Ex. No. | Name | Intermediates/ Procedure | $^1$H NMR | LCMS |
|---|---|---|---|---|
| | 3-(triazol-2-yl)py-ridine-2-carboxamide | | 4.05 (dd, J = 10.4, 8.0 Hz, 1H), 3.98 (t, J = 7.7 Hz, 1H), 2.25-2.14 (m, 1H), 2.11 (s, 3H), 1.97-1.81 (m, 2H), 1.61 (h, J = 6.8 Hz, 2H), 1.56-1.35 (m, 2H). | |

Biological Activity

Cloning, Baculovirus generation, large-scale infection of SF21 cells and membrane preparation. Human $OX_1$ or $OX_2$ receptor were cloned into Invitrogen's (ThermoFisher Scientific, UK) Bac-to-Bac Baculovirus Expression System. P0 baculovirus was generated by transfecting SF9 cells with bacmid DNA using Cellfectin® II transfection reagent (ThermoFisher Scientific, UK, Catalog number 10362-100). Following P0 generation P1 virus was then generated ready for large scale infection and membrane preparation. SF21 cells were grown in expression medium ESF921 (Expression Systems, USA, catalog number 96-001-01) supplemented with 10% heat-inactivated FBS and 1% Pen/Strep and were infected at a cell density of $2.5 \times 10^6$ cells/mL and a multiplicity of infection of 1.0 for both human $OX_1R$ and $OX_2R$. Incubation was carried out at over 48 h in a shaking incubator set at 27° C. The cell culture was then centrifuged at 2,500 rcf for 10 min at 4° C. The pellets were resuspended in cold PBS supplemented with Roche's Complete EDTA-free protease inhibitor cocktail tablets (Roche Applied Sciences, catalog number 05056489001), 1 mM PMSF and 1 mM EDTA. The resuspended cell paste was then centrifuged at 3,273 rcf for 12 min at 4° C. The supernatant was discarded and the pellet frozen at −80° C. The cell pellet from a 4 L culture was resuspended in buffer containing 50 mM HEPES pH 7.5, 150 mM NaCl, 8 Roche EDTA-Free protease inhibitor cocktail tablets and 1 mM PMSF. The suspension was left stirring at rt for 1 h and then homogenised for 90 s at 9,500 rpm using a VDI 25 (VWR, USA) homogeniser. The cells were then lysed using a Microfluidiser processor M-110L Pneumatic (Microfluidics, USA) at 60 PSI and membranes collected by ultracentrifugation at 204.7 k×g for 1 h. The supernatant was discarded and the pellet was resuspended and homogenised in 90 s at 9,500 rpm in 50 mL (25 mL for each 2 L culture) of buffer containing 50 mM Hepes pH 7.5, 150 mM NaCl, 3 Roche EDTA-free protease inhibitor cocktail tablets and 1 mM PMSF. The resulting membranes were then stored at −80° C.

Example A

[$^3$H]-radioligand binding assay. After thawing, membrane homogenates were resuspended in the binding buffer (8.5 mM HEPES, pH 7.4, 1.3 mM $CaCl_2$, 1.2 mM $MgSO_4$, 118 mM NaCl, 4.7 mM KCl, 4 mM $NaHCO_3$, 1.2 mM $KH_2PO_4$, 11 mM glucose) to a final assay concentration of 6.4 µg ($OX_1$) or 1.4 µg ($OX_2$) protein per well. Saturation isotherms were determined by the addition of various concentrations (0-30 nM) of [$^3$H]-4-(2,6-difluoro-4-methoxybenzyl)-2-(5,6-dimethoxypyridin-3-yl)-2H-1,2,4-benzothiadiazin-3(4H)-one 1,1-dioxide (Christopher et al, MedChemComm., 2015, 6, 947-955) in a total reaction volume of 250 µL for 90 min at rt. At the end of the incubation, membranes were filtered onto a 96-well GF/B filter pre-incubated with 0.5% polyethylenimine, with a Tomtec cell harvester and washed 5 times with 0.5 mL distilled water. Non-specific binding (NSB) was measured in the presence of 3.33 µM [4-(5-chloro-1,3-benzoxazol-2-yl)-7-methyl-1,4-diazepan-1-yl][5-methyl-2-(2H-1,2,3-triazol-2-yl)phenyl]methanone (Wertz et al, Angew. Chem. Int. Ed., 2011, 50, 11511-11515). Radioactivity on the filter was counted (1 min) on a Microbeta radiometric plate counter (Perkin Elmer) after addition of 50 µL of scintillation fluid (LabLogic: Part #SG-BXX-14). For competition binding experiments, membranes were incubated with [$^3$H]-4-(2,6-difluoro-4-methoxybenzyl)-2-(5,6-dimethoxypyridin-3-yl)-2H-1,2,4-benzothiadiazin-3(4H)-one 1,1-dioxide at a concentration equal to the $K_D$ value of the radioligand (1.5 nM for $OX_1$ and 0.75 nM for $OX_2$ receptors respectively) and 10 concentrations of the inhibitory compound (between the ranges of 10 µM-0.94 pmol). $IC_{50}$ values were derived from the inhibition curve and the equilibrium dissociation constant ($K_i$) values were calculated using the Cheng-Prusoff equation. The $pK_i$ values (where $pK_i = -\log_{10} K_i$) of compounds of the invention are shown in Table 4.

Generation of CHO stable cell lines expressing the human $OX_1R$ and $OX_2R$. Stable cell lines for the human $OX_1R$ and $OX_2R$ receptors were generated through the transfection of CHO cells using the transfection reagent Genejuice (Novagen number 70967) and cDNA coding for either the human $OX_1R$ or $OX_2R$. Cells were cultured in Sigma Nutrient Mixture F-12 Ham media (catalog number N6658) supplemented with 10% heat-inactivated FBS. Forty-eight hours after transfection, cells were harvested and placed under geneticin selection by culturing in Sigma Nutrient Mixture F-12 Ham media supplemented with 10% heat-inactivated FBS and geneticin (ThermoFisher Catalog number: 10131035). Selection of the final stable clone for each receptor was made on the basis of receptor expression, assay signal to noise and robustness though increasing passage. Selected clones for the human $OX_1R$ and $OX_2R$ were then frozen down into liquid nitrogen using Cell Freezing Medium-DMSO (Sigma-Aldrich catalog number: C6164).

Example B

IPone accumulation assay. A CHO cell line stably expressing either human $OX_1$ or $OX_2$ receptor was used with the IPone HTRF assay kit (CisBio: Part #62IPAPEJ) to measure receptor activation. The assay was optimised to measure the ability (potency; fpKb) of antagonists to reduce agonist (orexin A)-induced inositol phosphate turnover. Briefly, cells were plated onto half area 96-well white walled plates at a density of 12,500 cells/well. Sixteen hours post-plating cell growth media was replaced with antagonist concentration-response curve diluted in stimulation buffer (supplied with the kit). Cells were incubated in a humidified incubator (37° C.) for 30 min before an $EC_{80}$ challenge concentration (~20 nM ($OX_1$) and 40 nM ($OX_2$)) of orexin A (Tocris catalogue number 1455). After 30 min stimulation in a humidified incubator (37° C.) the assay was terminated by the addition of detection mixture as per manufacturer's instructions. The concentration of compound which reduced orexin-A stimulated turnover of inositol phosphates by 50% ($IC_{50}$) was calculated by fitting to a four parameter sigmoidal dose response curve. The $IC_{50}$ values were converted to $fpK_B$ values using the orexin A $pEC_{50}$ value estimated on each plate as well as the challenge concentration interpolated from the orexin A control curve. The $fpK_B$ values of compounds of the invention are shown in Table 4.

TABLE 4

$pK_i$ and $fpK_b$ Data

| Ex. No. | $pK_i$ average | | $fpK_b$ average | |
|---|---|---|---|---|
| | $OX_1$ | $OX_2$ | $OX_1$ | $OX_2$ |
| 1 | 9.0 | 7.3 | 9.1 | <7.2 |
| 2 | 7.7 | 5.6 | 7.3 | <5.6 |
| 3 | 8.3 | 5.4 | 7.7 | 5.9 |
| 4 | 8.0 | 5.9 | 8.0 | <5.9 |
| 5 | 8.5 | 6.0 | 8.5 | <6.0 |
| 6 | 8.1 | <5.2 | 8.1 | <6.2 |
| 7 | 8.1 | <5.3 | 7.6 | <6.1 |
| 8 | 8.4 | 5.8 | 7.8 | <6.1 |
| 9 | 8.2 | 5.9 | 7.6 | <6.7 |
| 10 | 8.1 | <5.9 | 7.1 | <6.1 |
| 11 | 7.9 | <5.8 | 7.5 | <6.0 |
| 12 | 8.2 | 6.4 | 8.3 | <6.4 |
| 13 | 7.8 | <6.0 | nd | <6.0 |
| 14 | 8.3 | 6.0 | 8.4 | <6.4 |
| 15 | 8.7 | 6.2 | 8.4 | <6.2 |
| 16 | 7.7 | <5.1 | 6.7 | <6.0 |
| 17 | 9.1 | 5.4 | 7.3 | <7.2 |
| 18 | 8.6 | 6.8 | 9.2 | <6.3 |
| 19 | 8.8 | 6.6 | 7.8 | <6.3 |
| 20 | 8.4 | 5.8 | 8.1 | <6.3 |
| 21 | 8.2 | 5.6 | 7.7 | <6.1 |
| 22 | 8.5 | 6.3 | 8.1 | <6.0 |
| 23 | 8.9 | 6.5 | 8.5 | <7.2 |
| 24 | 8.3 | 6.6 | 8.9 | <6.4 |
| 25 | 8.5 | 5.5 | 8.4 | <6.2 |
| 26 | 7.9 | <5.1 | 6.5 | <6.0 | nd = not determined.

The invention claimed is:

1. A compound of formula (1):

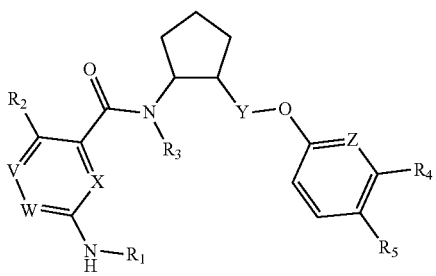

(1)

or a salt thereof, wherein
V is N, CH or CF;
W is N, CH or CF;
X is N, CH or CF;
Y is $CH_2$;
Z is N, CH or CF;
$R_1$ is selected from the group consisting of H, $C(O)R_6$, and $C_{1-6}$ alkyl, wherein the $C_{1-6}$ alkyl is optionally substituted with one or more halogens or hydroxy groups;
$R_2$ is a 5 or 6-membered heteroaryl ring containing two or three nitrogen atoms, and is optionally substituted with one or more fluorine atoms;

$R_3$ is H or $C_{1-3}$ alkyl;
$R_4$ is H or a halogen;
$R_5$ is H or a halogen;
$R_6$ is selected from the group consisting of $C_{1-6}$ alkyl, $C_{1-6}$ alkoxy and $C_{3-6}$ cycloalkyl, each of which is optionally substituted with —OMe or one or more fluorine atoms.

2. The compound according to claim 1, wherein the compound is of formula (2):

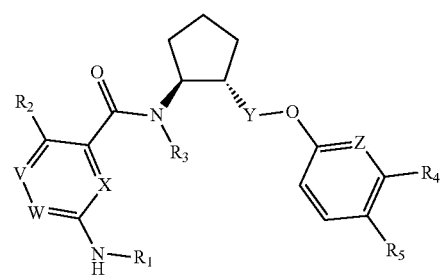

(2)

or a salt thereof, wherein $R_1$, $R_2$, $R_3$, $R_4$, $R_5$, V, W, X, Y, and Z are as defined in claim 1.

3. The compound according to claim 1, wherein V is CH.
4. The compound according to claim 1, wherein W is CH.
5. The compound according to claim 1, wherein X is N.
6. The compound according to claim 1, wherein Z is CH.
7. The compound according to claim 1, wherein $R_1$ is selected from H; C(O)OMe; $C(O)CH_3$; $C(O)CHF_2$; C(O)cyclopropyl; $C(O)CH_2OMe$; $CH_2CHF_2$ or $CH_2CH_2OH$.
8. The compound according to claim 7, wherein $R_1$ is C(O)OMe or $C(O)CH_3$.
9. The compound according to claim 1, wherein $R_2$ is selected from the group consisting of:

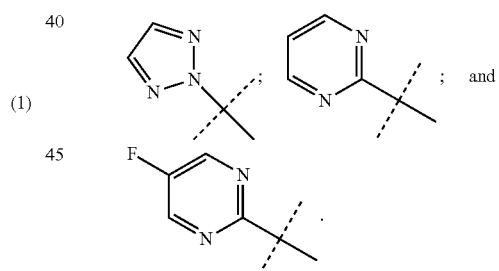

; and

10. The compound according to claim 9, wherein $R_2$ is

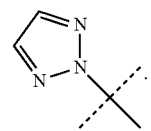

.

11. The compound according to claim 1, wherein $R_3$ is H.
12. The compound according to claim 1, wherein $R_4$ is H.
13. The compound according to claim 1, wherein $R_5$ is F.
14. The compound according to claim 1, wherein the compound is selected from the group consisting of:
5-acetamido-3-fluoro-N-[(1S,2S)-2-[(4-fluorophenoxy)methyl]cyclopentyl]-2-(triazol-2-yl)benzamide;

3-acetamido-2-fluoro-N-[(1S,2S)-2-[(4-fluorophenoxy)methyl]cyclopentyl]-6-pyrimidin-2-yl-benzamide;
6-acetamido-N-[(1S,2S)-2-[(4-fluorophenoxy)methyl]cyclopentyl]-3-(triazol-2-yl)pyridine-2-carboxamide;
6-amino-N-[(1S,2S)-2-[(4-fluorophenoxy)methyl]cyclopentyl]-3-(triazol-2-yl)pyridine-2-carboxamide;
6-acetamido-N-[(1S,2S)-2-[(4-fluorophenoxy)methyl]cyclopentyl]-N-methyl-3-(triazol-2-yl)pyridine-2-carboxamide;
6-acetamido-N-[(1S,2S)-2-[(4-chlorophenoxy)methyl]cyclopentyl]-3-(triazol-2-yl)pyridine-2-carboxamide;
6-acetamido-N-[(1S,2S)-2-[(4-fluorophenoxy)methyl]cyclopentyl]-N-isopropyl-3-(triazol-2-yl)pyridine-2-carboxamide;
6-acetamido-N-[(1S,2S)-2-[dideuterio-(4-fluorophenoxy)methyl]cyclopentyl]-3-(triazol-2-yl)pyridine-2-carboxamide;
6-acetamido-N-[(1S,2S)-2-[(3,4-difluorophenoxy)methyl]cyclopentyl]-3-(triazol-2-yl)pyridine-2-carboxamide;
methyl N-[6-[[(1S,2S)-2-[(4-fluorophenoxy)methyl]cyclopentyl]carbamoyl]-5-(triazol-2-yl)-2-pyridyl]carbamate;
6-[(2,2-difluoroacetyl)amino]-N-[(1S,2S)-2-[(4-fluorophenoxy)methyl]cyclopentyl]-3-(triazol-2-yl)pyridine-2-carboxamide;
6-amino-N-[(1S,2S)-2-[(4-fluorophenoxy)methyl]cyclopentyl]-3-pyrimidin-2-yl-pyridine-2-carboxamide;
6-(cyclopropanecarbonylamino)-N-[(1S,2S)-2-[(4-fluorophenoxy)methyl]cyclopentyl]-3-(triazol-2-yl)pyridine-2-carboxamide;
6-acetamido-N-[(1S,2S)-2-[(4-fluorophenoxy)methyl]cyclopentyl]-3-pyrimidin-2-yl-pyridine-2-carboxamide;
6-acetamido-N-[(1S,2S)-2-[(4-chlorophenoxy)methyl]cyclopentyl]-3-pyrimidin-2-yl-pyridine-2-carboxamide;
N-[(1S,2S)-2-[(4-fluorophenoxy)methyl]cyclopentyl]-6-[(2-methoxyacetyl)amino]-3-pyrimidin-2-yl-pyridine-2-carboxamide;
6-acetamido-N-[(1S,2S)-2-[(2,4-difluorophenoxy)methyl]cyclopentyl]-3-(triazol-2-yl)pyridine-2-carboxamide;
6-acetamido-N-[(1S,2S)-2-[(4-fluorophenoxy)methyl]cyclopentyl]-N-methyl-3-pyrimidin-2-yl-pyridine-2-carboxamide;
6-(2,2-difluoroethylamino)-N-[(1S,2S)-2-[(4-fluorophenoxy)methyl]cyclopentyl]-3-(triazol-2-yl)pyridine-2-carboxamide;
N-[(1S,2S)-2-[(4-fluorophenoxy)methyl]cyclopentyl]-6-(2-hydroxyethylamino)-3-(triazol-2-yl)pyridine-2-carboxamide;
6-acetamido-N-[(1S,2S)-2-[(4-fluorophenoxy)methyl]cyclopentyl]-3-(5-fluoropyrimidin-2-yl)pyridine-2-carboxamide;
6-amino-N-[(1S,2S)-2-[(4-fluorophenoxy)methyl]cyclopentyl]-3-(5-fluoropyrimidin-2-yl)pyridine-2-carboxamide;
2-acetamido-N-[(1S,2S)-2-[(4-fluorophenoxy)methyl]cyclopentyl]-5-(triazol-2-yl)pyridine-4-carboxamide;
2-acetamido-N-[(1S,2S)-2-[(4-fluorophenoxy)methyl]cyclopentyl]-5-pyrimidin-2-yl-pyridine-4-carboxamide;
5-acetamido-N-[(1S,2S)-2-[(4-fluorophenoxy)methyl]cyclopentyl]-2-(triazol-2-yl)pyridine-3-carboxamide;
6-acetamido-N-[(1S,2S)-2-[(5-fluoro-2-pyridyl)oxymethyl]cyclopentyl]-3-(triazol-2-yl)pyridine-2-carboxamide,
or a pharmaceutically acceptable salt thereof.

15. A pharmaceutically acceptable salt of a compound according to claim 1.

16. A pharmaceutical composition comprising the compound according to claim 1, and a pharmaceutically acceptable excipient.

17. The compound according to claim 1, wherein the compound is an antagonist of the orexin $OX_1$ receptor.

18. A method for treating neurological or psychiatric disorders in a subject having the disorders, comprising administering an effective amount of the compound of claim 1 to the subject.

19. A method of treating a disorder in a subject having the disorder, comprising administering an effective amount of the compound of claim 1 to the subject, wherein the disorder is selected from the group consisting of:

substance related disorders, addictive disorders, opioid use disorder, opioid intoxication, opioid withdrawal, opioid induced disorder, unspecified opioid related disorder, stimulant use disorder, stimulant intoxication, stimulant withdrawal, stimulant induced disorders, unspecified stimulant related disorder, caffeine related disorders, caffeine intoxication, caffeine withdrawal, unspecified caffeine related disorders, tobacco related disorders, tobacco use disorder, tobacco withdrawal, other tobacco induced disorders, unspecified tobacco related disorder, alcohol use disorder, alcohol intoxication, alcohol withdrawal, unspecified alcohol related disorder, *cannabis* related disorders, *cannabis* use disorder, *cannabis* intoxication, *cannabis* withdrawal, unspecified *cannabis* related disorders, hallucinogen related disorders, phencyclidine use disorder, phencyclidine intoxication, hallucinogen use disorder, hallucinogen persisting perception disorder, unspecified hallucinogen related disorder, inhalant related disorders, inhalant use disorder, inhalant intoxication, inhalant induced disorders, unspecified inhalant related disorder, sedative, hypnotic or anxiolytic related disorders, use disorder, intoxication, or withdrawal), gambling disorder, internet gaming disorder, addiction to sex or internet use), anxiety disorders, separation anxiety disorder, specific phobia disorder, social anxiety disorder (social phobia), panic disorder, agoraphobia, generalized anxiety disorder, substance/medication induced anxiety disorder, anxiety disorder due to another medical condition, disruptive mood dysregulation disorder, major depressive disorder (MDD), MDD with one or more of anxious distress, mixed features, atypical features, peripartum onset or seasonal pattern), persistent depressive disorder (dysthymia), optionally with anxious distress, mixed features, atypical features, peripartum onset, or seasonal pattern), premenstrual dysphoric disorder, substance/medication-induced depressive disorder, unspecified depressive disorder, bipolar disorders, bipolar I disorder, bipolar II disorder, cyclothymic disorder, substance/medication-induced bipolar disorder, bipolar disorder due to medical condition schizophrenia, spectrum disorders, schizotypal personality, delusional disorder, schizophreniform disorder, schizophrenia, schizoaffective disorder, substance/medication-induced psychotic disorder, post traumatic stress disorder, acute stress disorder, adjustment disorders, body dysmorphia, trichlotillomania, excoriation, obsessive-compulsive disorder, feeding and eating disorders, binge eating disorder, anorexia nervosa, bulimia nervosa, cachexia, obesity, Prader Willi syndrome, sleep-wake disorders, neurodegenerative disorders, dementia, behavioural symptoms of neurodegenerative disorders, movement disorders, diabetes, impaired glucose tolerance, cardiovascular disease, hypertension, hypothalamic/pituitary disorders, neuropathic pain, restless leg syndrome, migraine, cluster headache, tension-type headache, trigeminal autonomic cephalalgias, hemicrania continua, trigeminal neuralgia, headache disorders, hyperalgesia, pain, hyperalgesia, causalgia, allodynia, acute pain, burn pain, atypical facial pain, back pain, complex regional pain syndrome I and II, arthritic pain, sports injury pain, pain related to infection, irritable bowel syndrome, angina pain, inflammatory disorders, renal/urinary disorders, respiratory disorders, cancer, prostate cancer, liver cancer, colon cancer, endometrial cancer, pancreatic cancer, cancers of the central nervous system, and cancers of the peripheral nervous system.

20. A method of treating a disorder in a subject having the disorder, comprising administering an effective amount of the compound of claim 1 to the subject, wherein the disorder is selected from the group consisting of substance related and addictive disorders, post traumatic stress disorder, panic disorder, major depressive disorder with anxious distress, diseases related to modulation of sympathetic outflow, hypertension, pain, headache, and cancer.

* * * * *